US008548569B2

(12) United States Patent
Piferi et al.

(10) Patent No.: US 8,548,569 B2
(45) Date of Patent: Oct. 1, 2013

(54) HEAD FIXATION ASSEMBLIES FOR MEDICAL PROCEDURES

(75) Inventors: Peter Piferi, Orange, CA (US); Christopher Keidl, Hartland, WI (US)

(73) Assignee: MRI Interventions, Inc., Memphis, TN (US)

( * ) Notice: Subject to any disclaimer, the term of this patent is extended or adjusted under 35 U.S.C. 154(b) by 748 days.

(21) Appl. No.: 12/685,849

(22) Filed: Jan. 12, 2010

(65) Prior Publication Data

US 2010/0185198 A1    Jul. 22, 2010

Related U.S. Application Data

(63) Continuation-in-part of application No. 12/237,091, filed on Sep. 24, 2008, now Pat. No. 8,099,150, which is a continuation-in-part of application No. 12/134,412, filed on Jun. 6, 2008, now Pat. No. 8,175,677.

(60) Provisional application No. 60/974,821, filed on Sep. 24, 2007.

(51) Int. Cl.
    *A61B 5/00*    (2006.01)
(52) U.S. Cl.
    USPC ........... 600/429; 600/407; 600/410; 600/415; 600/417; 600/425
(58) Field of Classification Search
    USPC ................. 600/407, 410, 415, 417, 425, 429
    See application file for complete search history.

(56) References Cited

U.S. PATENT DOCUMENTS

| 4,612,930 A | 9/1986 | Bremer |
| 5,125,888 A | 6/1992 | Howard et al. |

(Continued)

FOREIGN PATENT DOCUMENTS

| DE | 100 15 670 A1 | 10/2001 |
| DE | 100 29 736 A1 | 1/2002 |

(Continued)

OTHER PUBLICATIONS

Notification of Transmittal of the International Search Report and the Written Opinion of the International Searching Authority, or the Declaration; Date of Mailing: Sep. 15, 2010, Corresponding to International Application No. PCT/US2010/020719, 8 pages.

(Continued)

*Primary Examiner* — Peter Luong
(74) *Attorney, Agent, or Firm* — Myers Bigel Sibley & Sajovec, PA

(57) ABSTRACT

A head fixation assembly includes a head fixation frame, a plurality of upper head fixation members, a plurality of lower head fixation members, and at least one drive mechanism. The head fixation frame includes a pair of upwardly extending spaced-apart arms defining a free space therebetween. At least one upper head fixation member extends from each of the respective arms of the head fixation frame, with each upper head fixation member adjustable relative to the head fixation frame and adapted to engage a patient's head within the free space of the head fixation frame. The lower head fixation members extend from the head fixation frame between the pair of arms, with each member adjustable relative to the head fixation frame and adapted to engage an underside of the patient's head within the free space of the head fixation frame. The at least one drive mechanism is in communication with the lower head fixation members, and is externally accessible so as to allow a user to be able to directly or indirectly advance and/or retract the lower head fixation members while the patient's head resides in the free space of the head fixation frame.

31 Claims, 37 Drawing Sheets

(56) References Cited

U.S. PATENT DOCUMENTS

| | | | |
|---|---|---|---|
| 5,276,927 | A | 1/1994 | Day |
| 5,388,580 | A | 2/1995 | Sullivan et al. |
| 5,638,819 | A | 6/1997 | Manwaring et al. |
| 5,695,501 | A | 12/1997 | Carol et al. |
| 5,699,801 | A | 12/1997 | Atalar et al. |
| 5,707,335 | A | 1/1998 | Howard et al. |
| 5,779,694 | A | 7/1998 | Howard et al. |
| 5,928,145 | A | 7/1999 | Ocali et al. |
| 5,961,528 | A | 10/1999 | Birk et al. |
| 5,971,997 | A | 10/1999 | Guthrie et al. |
| 6,006,126 | A | 12/1999 | Cosman |
| 6,045,553 | A | 4/2000 | Iversen et al. |
| 6,050,992 | A | 4/2000 | Nichols |
| 6,167,311 | A | 12/2000 | Rezai |
| 6,195,577 | B1 | 2/2001 | Truwit et al. |
| 6,198,961 | B1 | 3/2001 | Stern et al. |
| 6,216,030 | B1 | 4/2001 | Howard et al. |
| 6,263,229 | B1 | 7/2001 | Atalar et al. |
| 6,284,971 | B1 | 9/2001 | Atalar et al. |
| 6,298,262 | B1 | 10/2001 | Franck et al. |
| 6,315,783 | B1 | 11/2001 | Katz et al. |
| 6,356,786 | B1 | 3/2002 | Rezai et al. |
| 6,368,330 | B1 * | 4/2002 | Hynes et al. .................. 606/130 |
| 6,405,079 | B1 | 6/2002 | Ansarinia |
| 6,438,423 | B1 | 8/2002 | Rezai et al. |
| 6,526,318 | B1 | 2/2003 | Ansarinia |
| 6,529,765 | B1 | 3/2003 | Franck et al. |
| 6,539,263 | B1 | 3/2003 | Schiff et al. |
| 6,606,513 | B2 | 8/2003 | Lardo et al. |
| 6,609,030 | B1 | 8/2003 | Rezai et al. |
| 6,628,980 | B2 | 9/2003 | Atalar et al. |
| 6,675,033 | B1 | 1/2004 | Lardo et al. |
| 6,701,176 | B1 | 3/2004 | Halperin et al. |
| 6,708,064 | B2 | 3/2004 | Rezai |
| 6,752,812 | B1 | 6/2004 | Truwit |
| 6,782,288 | B2 | 8/2004 | Truwit et al. |
| 6,896,678 | B2 | 5/2005 | Tweardy |
| 6,904,307 | B2 | 6/2005 | Karmarkar et al. |
| 7,139,601 | B2 | 11/2006 | Bucholz et al. |
| 7,155,316 | B2 | 12/2006 | Sutherland et al. |
| 7,167,760 | B2 | 1/2007 | Dawant et al. |
| 7,217,276 | B2 | 5/2007 | Henderson et al. |
| 7,706,858 | B1 | 4/2010 | Green et al. |
| 2002/0049451 | A1 | 4/2002 | Parmer et al. |
| 2002/0052610 | A1 | 5/2002 | Skakoon et al. |
| 2003/0028095 | A1 | 2/2003 | Tulley et al. |
| 2003/0050557 | A1 | 3/2003 | Susil et al. |
| 2004/0046557 | A1 | 3/2004 | Karmarkar et al. |
| 2004/0215279 | A1 | 10/2004 | Houben et al. |
| 2004/0228796 | A1 | 11/2004 | Talpade |
| 2005/0054910 | A1 | 3/2005 | Tremblay et al. |
| 2005/0070781 | A1 | 3/2005 | Dawant et al. |
| 2005/0075650 | A1 | 4/2005 | Dinkler |
| 2007/0191706 | A1 | 8/2007 | Calderon et al. |
| 2007/0270683 | A1 | 11/2007 | Meloy |
| 2009/0088627 | A1 | 4/2009 | Piferi et al. |

FOREIGN PATENT DOCUMENTS

| | | |
|---|---|---|
| WO | WO 96/02204 | 2/1996 |
| WO | WO 98/52064 A1 | 11/1998 |
| WO | WO 03/102614 A1 | 12/2003 |
| WO | WO 2004/029782 A3 | 4/2004 |
| WO | WO 2006/081409 A2 | 8/2006 |
| WO | WO 2007/064739 A3 | 6/2007 |

OTHER PUBLICATIONS

Jorgensen, E., "Brain Image Analysis Team Joins SCI Institute," http://www.sci.utah.edu/stories/2007/Gerig_NeuroimageAnalysis.html, (2007), 3 Pages.

Martin, A.J., et al., "Placement of Deep Brain Stimulator Electrodes Using Real-Time High-Field Interventional Magnetic Resonance Imaging," *Magnetic Resonance in Medicine*, 2005, pp. 1107-1114, vol. 54.

Sauser, B.,"A 3-D View of the Brain," http://www.technologyreview.com/Biotech/19140, Aug. 6, 2007, 3 Pages.

International Search Report, mailed Jan. 26, 2009, for corresponding PCT Application No. PCT/US/2008/011043.

International Preliminary Report on Patentability for PCT/US2010/020719, mailed Jul. 26, 2012.

Fa-Hsuan Li, et al; *A Wavelet-Based Approximation of Surface Coil Sensitivity Profiles for Correction of Image Intensity Inhomogeneity and Parallel Imaging Reconstruction*; (Human Brain Mapping 19:96-111 ((2003 Wiley-Liss, Inc.)).

* cited by examiner

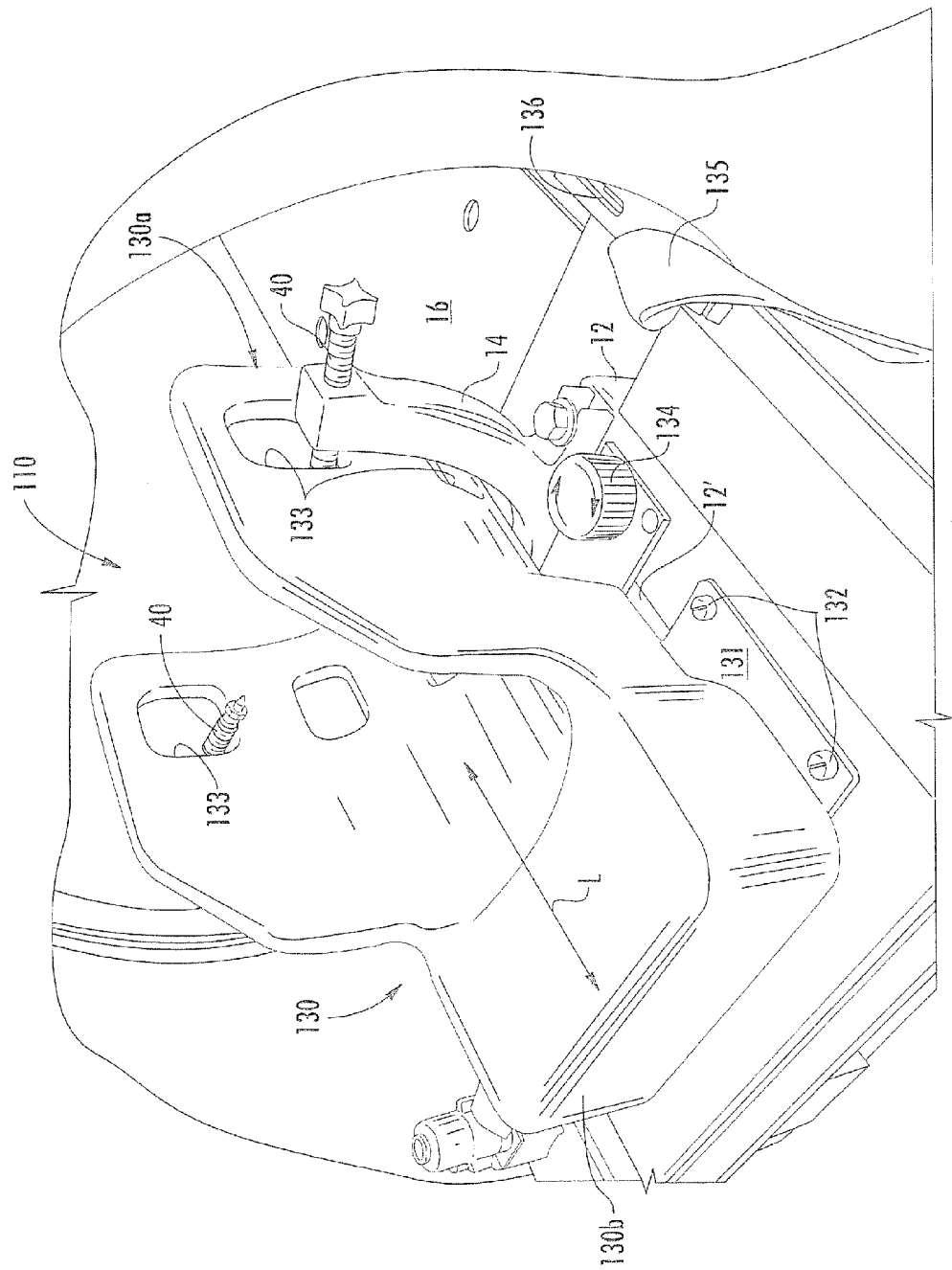

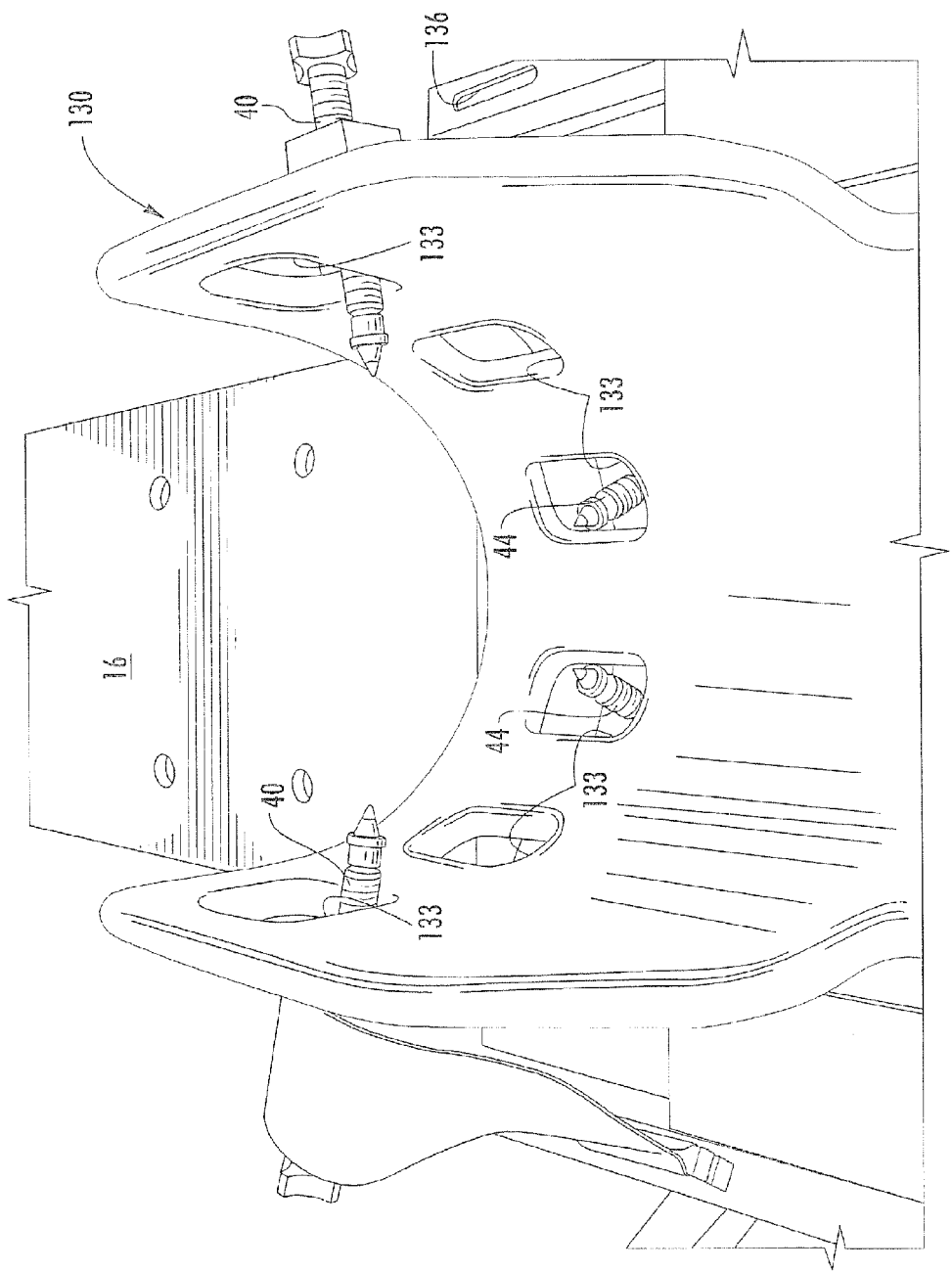

HEAD FIXATION ASSEMBLIES FOR MEDICAL PROCEDURES

RELATED APPLICATIONS

This application is a continuation-in-part application of U.S. patent application Ser. No. 12/237,091, filed Sep. 24, 2008 now U.S. Pat. No. 8,099,150, which claims the benefit of and priority to U.S. Provisional Patent Application No. 60/974,821, filed Sep. 24, 2007, and which is a continuation-in-part application of U.S. patent application Ser. No. 12/134,412, filed Jun. 6, 2008 now U.S. Pat. No. 8,175,677, the disclosures of which are incorporated herein by reference as if set forth in their entireties.

FIELD OF THE INVENTION

The present invention relates generally to medical systems and apparatus and, more particularly, to MRI-interventional systems and apparatus.

BACKGROUND

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc. One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum.

Real-time MRI-guided tools and procedures for DBS, as well as for other interventional medical procedures, are being developed. However, the quality of an MRI image depends on the strength of the received signal. As such radio frequency (RF) receiving coils typically are placed in close proximity to the area of a patient being imaged. These coils are often referred to as surface or head coils. One type of head coil used for imaging of the brain is a "bird cage" coil, as described in U.S. Pat. No. 6,396,271. Typically, a birdcage coil has a pair of circular end rings which are bridged by a plurality of equally-spaced straight segments or legs about the periphery of a cylindrical volume. A patient's head fits through one of the end rings and into the enclosed volume and a patient is typically unrestrained and able to move.

SUMMARY

In view of the above, improved head fixation assemblies for holding the head of a patient during medical procedures are provided. According to some embodiments of the present invention, a head fixation assembly includes a head fixation frame, a plurality of upper head fixation members, a plurality of lower head fixation members, and at least one drive mechanism in communication with the lower head fixation members. The head fixation frame includes a pair of upwardly extending spaced-apart arms defining a free space therebetween.

At least one of the upper head fixation members extends from each of the respective arms of the head fixation frame. The upper head fixation members are adjustable relative to the head fixation frame and adapted to engage a patient's head within the free space of the head fixation frame. Each lower head fixation member extends from the head fixation frame between the pair of arms, and each lower head fixation member is adjustable relative to the head fixation frame and adapted to engage an underside of the patient's head within the free space of the head fixation frame. The at least one drive mechanism is externally accessible so as to allow a user to be able to directly or indirectly advance and/or retract the lower head fixation members while the patient's head resides in the free space of the head fixation frame.

In some embodiments of the present invention, the head fixation assembly is a modular head fixation assembly adapted to be releasably locked to a gantry. The modular head fixation assembly includes: a base having a bottom surface, first and second opposite end portions, and transversely spaced-apart sides, wherein the head fixation frame is releasably attached to the base at the first end portion; and either a first locking mechanism having a first configuration or a second locking mechanism having a second, different configuration, wherein the first and second locking mechanisms are each adapted to releasably lock the head fixation assembly to the gantry. The modular head fixation assembly may include the first locking mechanism, wherein the first locking mechanism includes a pair of side mounting assemblies, each one releasably attached to a respective arm of the head fixation frame and including a downwardly extending portion adapted to engage the gantry and thereby releasably lock the sides of the head fixation assembly to the gantry. The modular head fixation assembly may include the second locking mechanism, wherein the second mechanism includes at least one downwardly extending portion on the bottom surface of the base adjacent each of the sides of the base, the downwardly extending portions adapted to engage the gantry and thereby releasably lock the sides of the head fixation assembly to the gantry.

In some embodiments, the modular head fixation assembly is an MRI-compatible assembly, and includes a head coil apparatus secured to the base, at least a portion of the head coil apparatus extending inside the free space of the head fixation frame, the head coil apparatus including at least one RF coil and configured to surround at least a portion of a patient's head, the head coil apparatus further including a plurality of spaced-apart access windows, wherein the upper and lower head fixation members each extend through a respective access window. The head coil apparatus may be adjustably secured to the base along a longitudinal direction relative to the head fixation frame. The base may include at least one lock configured to inhibit longitudinal movement of the head coil apparatus. At least one camera holder may be attached to the base, wherein the camera holder is configured to hold an MRI-compatible camera therewithin. The head coil apparatus may include a pair of upwardly-extending leg portions that reside at least partially within the head fixation frame, and a face plate may be removably attached to the head coil apparatus at the leg portions.

Each upper head fixation member may extend inwardly and downwardly at an angle of between about zero and fifteen degrees (0°-15°) relative to horizontal. Each lower head fixation member may extend upwardly at an angle of between about ten and sixty degrees (10°-60°) relative to vertical.

In some embodiments, the head fixation frame includes: an upper passageway in each arm; a plurality of upper anti-rotation blocks, one each configured to snugly reside within a respective upper arm passageway, wherein each upper anti-rotation block includes a channel, and wherein one upper head fixation member extends through a respective one of the upper anti-rotation block channels; a pair of lower passageways residing in the head fixation frame between the pair of arms; and a plurality of lower anti-rotation blocks, one each configured to snugly reside within a respective lower passageway, wherein each lower anti-rotation block includes a channel, and wherein one lower head fixation member extends through a respective one of the lower anti-rotation block channels. The head fixation members may be threaded, and the upper head fixation members may threadingly engage the upper anti-rotation block channels and the lower head fixation members may threadingly engage the lower anti-rotation block channels.

Each upper head fixation member may include: an elongated outer member having opposite proximal and distal ends, the elongated member having a channel open at the distal end; a rod residing within the channel; and a tip member residing within the channel at the distal end of the elongated member and extending outwardly therefrom, the tip member having a sharp point. The elongated outer member may be polymeric and the rod may be ceramic.

Each lower head fixation member may include: an elongated outer member having opposite proximal and distal ends, the elongated member having a channel open at the distal end; a rod residing within the channel; and a tip member residing within the channel at the distal end of the elongated member and extending outwardly therefrom, the tip member having a sharp point; wherein the at least one drive mechanism is configured to receive the proximal end of the elongated member. The elongated outer member may be polymeric and the rod may be ceramic.

In some embodiments, the head fixation frame includes a pair of spaced-apart slots extending therethrough and residing between the pair of arms above a bottom surface of the head fixation frame. The at least one drive mechanism includes a pair drive mechanisms, wherein each drive mechanism includes a substantially disk-shaped rotatable drive positioned in a respective slot of the head fixation frame. Each drive includes a substantially centered aperture configured to receive a portion of a respective lower head fixation member, and each drive mechanism is configured to directly advance and/or retract the respective lower head fixation member relative to the head fixation frame responsive to rotation of the rotatable drive. A respective lower head fixation member may define an axis, and a respective drive mechanism may be configured to directly advance and/or retract the lower head fixation member responsive to rotation of the drive about the lower head fixation member axis. Each lower head fixation member may have opposite proximal and distal ends, and each lower head fixation member may be threaded and have a substantially circular cross section along a segment extending inward from the distal end and each lower head fixation member may be non-threaded and have a substantially square cross section along a segment extending outward from the proximal end, and the drive apertures may be substantially square-shaped and may be configured to receive the proximal ends of the lower fixation members.

In some embodiments, the at least one drive mechanism includes a pair of drive mechanisms, and each drive mechanism includes a rotatable drive that is accessible by a user at a location remote from a respective lower head fixation member. The drive mechanism further includes a gear assembly that communicates with the lower head fixation member and the remote drive, and each drive mechanism is configured to indirectly advance and/or retract the respective lower head fixation member relative to the head fixation frame responsive to rotation of the drive. A respective lower head fixation member may define an axis, and a respective drive mechanism is may be configured to indirectly advance and/or retract the lower head fixation member responsive to rotation of the drive about an axis that is different than the axis defined by the lower head fixation member. Each rotatable drive may have opposite proximal and distal ends with a worm located at the distal end, and the rotatable drive may be configured to be rotated at the proximal end, and the worm may engage with a worm gear associated with the lower head fixation member such that axial rotation of the rotatable drive causes axial rotation of the lower head fixation member. In some embodiments, the rotatable drives are positioned on a rear side of the head fixation frame.

A method for positioning a patient in a head fixation assembly includes: positioning a patient's head in a head coil apparatus held in a head fixation frame, wherein the head fixation frame includes a pair of upwardly extending spaced-apart arms, an upper pair of head fixation members extending from respective arms of the head fixation frame, and a lower pair of head fixation members extending from the head fixation frame between the arms; directing the lower pair of head fixation members relative to the head fixation frame to move the patient's head upward or downward to a desired position in relation to the head coil apparatus; then directing the upper pair of head fixation members inward and downward relative to the head fixation frame to secure the patient's head in the head fixation frame; and then adjusting the lower pair of head fixation members relative to the head fixation frame to tightly contact and secure the patient's head in the head fixation frame.

In some embodiments, each lower head fixation member defines a respective axis, and the head fixation frame includes a pair of rotatable drives, each one at a location remote from a respective lower head fixation member and configured to advance and retract the lower head fixation member responsive to rotation of the drive about an axis that is different than the axis defined by the lower head fixation member. The steps of directing and adjusting the lower pair of head fixation members may include rotating the pair of rotatable drives.

In some embodiments, each lower head fixation member defines a respective axis, wherein the head fixation frame includes a pair of substantially disk-shaped rotatable drives, each one configured to receive at least a portion of a respective lower head fixation member and configured to advance and retract the lower head fixation member responsive to rotation of the drive about the same axis defined by the lower head fixation member. The steps of directing and adjusting the lower pair of head fixation members may include rotating the pair of substantially disk-shaped drives.

The head coil apparatus may be adjustably secured to the base, and the method may further include the step of slidably translating the head coil apparatus to a desired longitudinal position in relation to the patient's head after the step of adjusting the lower pair of head fixation members.

Head fixation assemblies according to embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, MRI-guided ablation procedures, etc.

Head fixation assemblies according to embodiments of the present invention can be advantageous over conventional systems because they can be easily adjustable for various patient head sizes and shapes, and can support large forces exerted in any direction without movement, thereby providing stability to the head of a patient during various interventional procedures. In addition, head fixation assemblies according to embodiments of the present invention do not allow a patient's head to move in any direction, including pivotal movement. Moreover, head fixation assemblies according to embodiments of the present invention do not interfere with other components or a physician's access to the patient. Head fixation assemblies, according to embodiments of the present invention can be sterilized within an autoclave, and can be wiped down with disinfectant and cleaners. Head fixation assemblies, according to embodiments of the present invention can be installed and used many times without degradation, or may be single-use and disposable.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 19 is a side perspective view of a head fixation assembly including an alternate design of an open-face head coil apparatus, according to other embodiments of the present invention.

FIG. 20 is a top perspective view of the head fixation assembly of FIG. 19.

DETAILED DESCRIPTION

Figure 1:
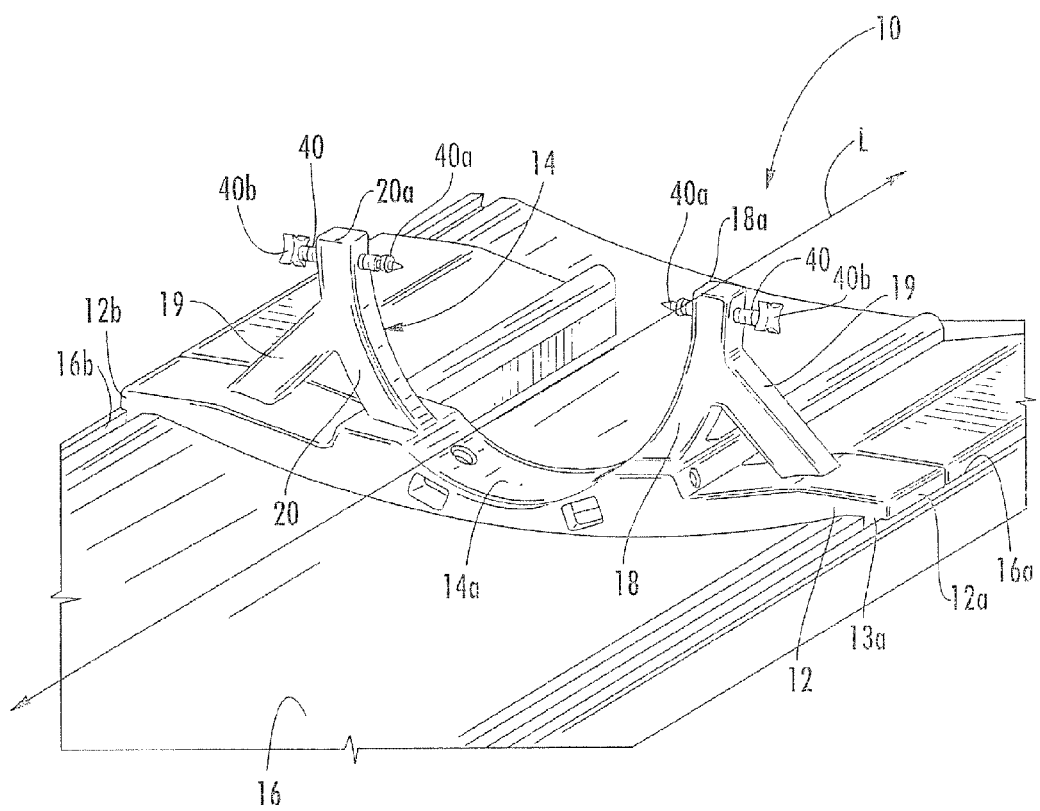
FIG. 1 is a perspective view of the head fixation frame of a head fixation assembly, according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly" "vertical", "horizontal" and the like are used herein for the purpose of explanation only unless specifically indicated otherwise.

The term "MRI compatible" means that a device is safe for use in an MRI environment and/or can operate as intended in an MRI environment, and, as such, if residing within the high-field strength region of the magnetic field, is typically made of a non-ferromagnetic MRI compatible material(s) suitable to reside and/or operate in a high magnetic field environment.

The term "gantry" refers to a patient support of an MRI scanner and may include the patient table or other structure.

The term "rod" refers to an elongate member with rigidity, such as a bolt, pin, screw, etc.

The term "head fixation member" refers to an elongate member with sufficient structural rigidity to secure and/or move the head of a patient and may take the form of a bolt, pin, screw, etc. Head fixation members according to various embodiments of the present invention may be threaded skull pins.

The term "head fixation assembly" refers to an assembly including at least a head fixation frame, as described in more detail below. Head fixation assemblies according to various embodiments of the present invention may further include a base and/or a head coil apparatus and/or associated components, as further described in more detail below.

Head fixation assemblies according to embodiments of the present invention facilitate guiding and/or placing diagnostic or interventional devices and/or therapies to any desired internal region of the brain. For example, head fixation assemblies according to embodiments of the present invention facilitate the placement of implantable DBS leads for brain stimulation, typically deep brain stimulation, and facilitate delivering tools or therapies that stimulate a desired region of the sympathetic nerve chain. Embodiments of the present invention can be used with any MRI scanner system, including open and closed bore designs and any field strength, typically between about 1.0 T-1.0 T. As such, head coils used to obtain MRI signals are optional.

While various embodiments are described for use in MRI scanners, certain components may also be useful for other medical systems.

Embodiments of the present invention have other uses inside or outside the brain include stem cell placement, gene therapy or drug delivery for treating physiological conditions. Some embodiments can be used to treat tumors. Some embodiments can be used for diagnosing or delivering any desired therapy such as, for example, RF stimulation or ablation, laser stimulation or ablation, cryogenic stimulation or ablation, etc.

Embodiments of the present invention will now be described in detail below with reference to the figures. Referring initially to FIG. 1, a head fixation assembly 10 is illustrated without a head coil apparatus (FIG. 2) attached thereto. The illustrated head fixation assembly 10 includes a base 12 and a head fixation frame 14. The base 12 and head fixation frame 14 may be an integral unit, or may be separate components. In the illustrated embodiment, the head fixation frame 14 and base 12 are an integral unit. The base 12 is configured to be removably secured to the gantry 16 associated with an MRI scanner. In the illustrated embodiment, the base 12 includes opposite first and second end portions 12a, 12b. A downwardly extending portion 13a, 13b of each end portion 12a, 12b is configured to engage a respective groove 16a, 16b formed within and extending along the gantry 16 in substantially parallel, spaced-apart relationship, as illustrated. The cross sectional shape of each respective downwardly extending portion 13a, 13b is configured to matingly engage a respective groove 16a, 16b. For example, the downwardly extending portions 13a, 13b may have a trapezoidal or dovetail configuration (FIG. 3). Each groove 16a, 16b has a corresponding trapezoidal or dovetail shape.

To install the illustrated base 12, downwardly extending portions 13a, 13b engage the respective grooves 16a, 16b at a free end of the gantry 16 and the base 12 and the frame 14 are moved along the gantry 16 to a selected position. One or more set screws or other locking mechanisms (not shown) may be utilized to maintain the base 12 at a selected location on the gantry 16.

Embodiments of the present invention, however, are not limited to the illustrated base 12 or to the illustrated engagement of base 12 and gantry 16. Furthermore, it is anticipated that a base for a head fixation assembly of the present invention can be customized to fit and be secured to any type of gantry. That is, the base may be a universal base usable with several different MRI scanners from different manufacturers, or may be MRI scanner type specific.

The illustrated head fixation frame 14 includes a pair of elongated arms 18, 20 that extend outwardly from the base 12 in adjacent, spaced-apart relationship to form a space for receiving the head of a patient. The illustrated arms 18, 20 lie in substantially the same plane (i.e., are substantially coplanar) and have an arcuate configuration. The surface 14a of the head fixation frame 14 between the pair of arms 18, 20 has a concave configuration. As such, the concave surface 14a and arcuate arms 18, 20 give the head fixation frame 14 a substantially U-shaped configuration. In the illustrated embodiment, a bracing member 19 is attached to each respective arcuate arm 18, 20 to provide rigidity and stability. However, head fixation frames according to embodiments of the present invention do not require bracing members. Moreover, head fixation frames according to embodiments of the present invention may have various structural configurations, without limitation.

The illustrated head fixation assembly 10 includes a longitudinally extending head coil apparatus 30 (FIG. 2) secured to the head fixation frame 14. The head coil apparatus 30 has an open-face, substantially U-shaped configuration with spaced-apart leg portions 30a, 30b having free ends. The head coil apparatus 30 is secured to the head fixation frame 14 between the head fixation frame arms 18, 20 such that the free ends of the leg portions 30a, 30b extend upwardly, as illustrated. Also, the head coil apparatus 30 can be adjustable along a longitudinal direction L (FIG. 1) relative to the head fixation frame 14, as will be described below.

The illustrated open-face head coil apparatus 30 includes a pair of longitudinally spaced-apart, U-shaped supports 32, 34 and a plurality of spaced apart connecting members 36 that extend longitudinally between the supports 32, 34. RF coils are contained within at least some of the connecting members 36, along with the circuitry for controlling RF excitation of the RF coils. An exemplary supplier of RE coils that may be utilized is Midwest RF, LLC., Hartland, Wis. The head coil apparatus 30 is configured to surround at least a portion of a patient's head supported by the head fixation frame 14. As such, RF coils can be positioned as desired relative to a patient's head. Embodiments of the present invention are not limited to the configuration of the illustrated open-face head coil apparatus 30 of FIG. 2. Head coil apparatus 30 may have various shapes and configurations, but includes an open-face configuration.

Figure 2:
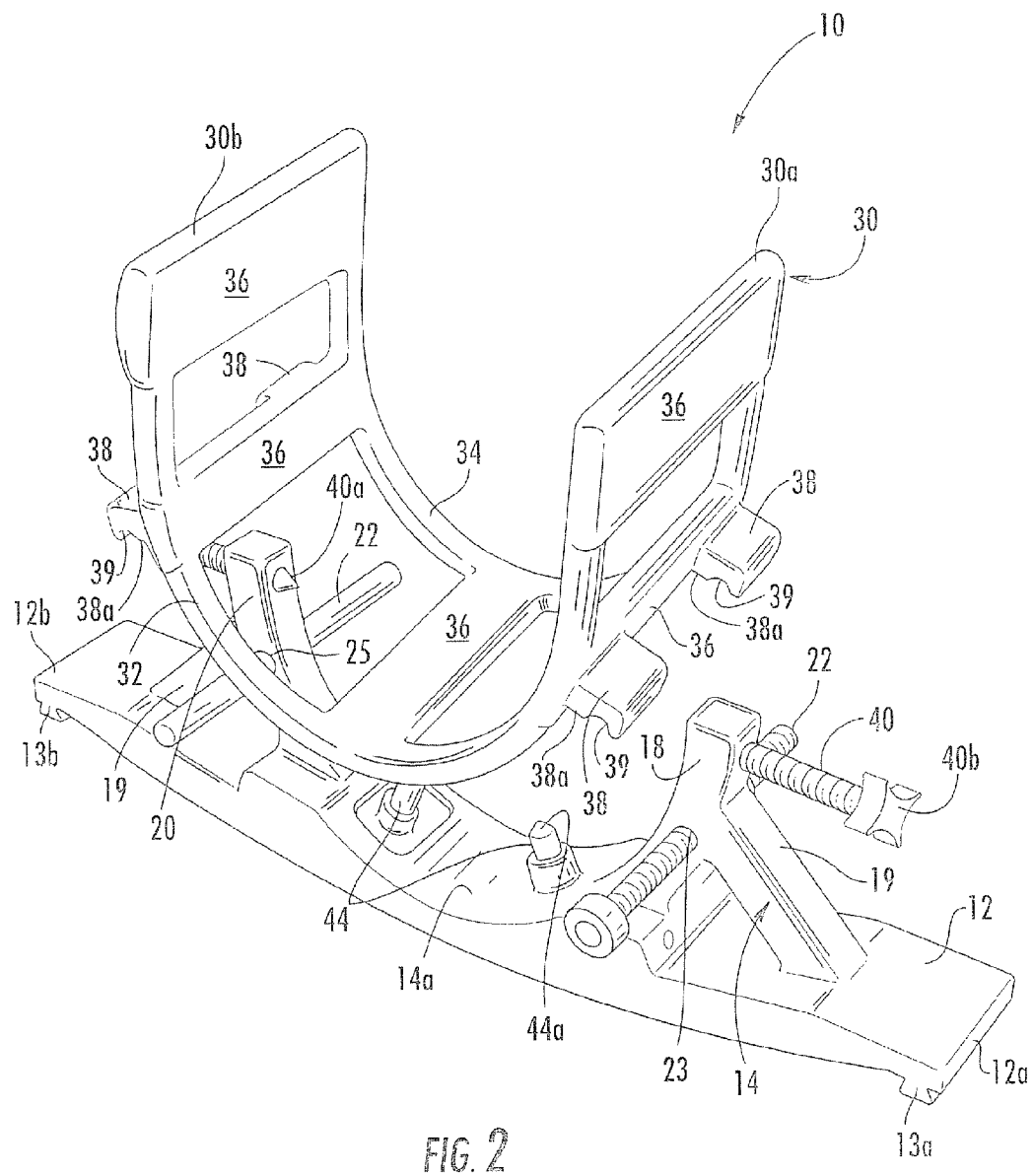
FIG. 2 illustrates the attachment of an open-face head coil apparatus that can cooperate with a head fixation frame, such as that shown in FIG. 1, according to some embodiments of the present invention.
Figure 3:
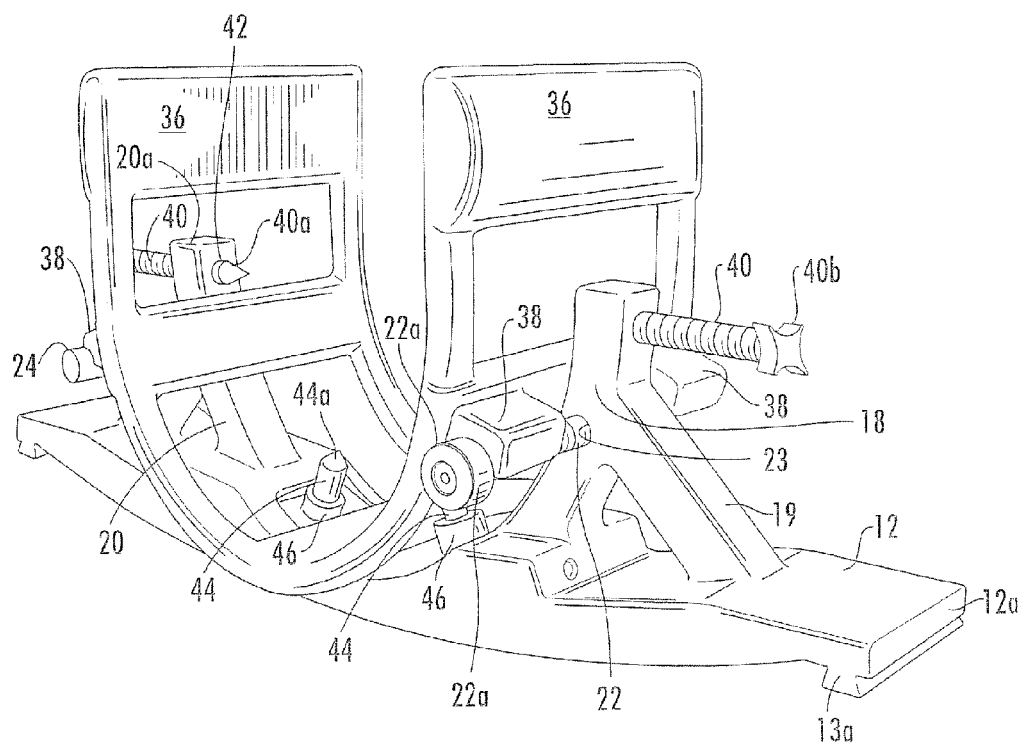
FIG. 3 is a perspective view of the open-face head coil apparatus of FIG. 2 removably and adjustably secured to the head fixation frame of FIG. 1, according to some embodiments of the present invention.

In some embodiments, the head coil apparatus 30 can include two pair of spaced apart shoulders 38 that extend outwardly from respective, opposing connecting members 36, as illustrated in FIGS. 2-3. The shoulders 38 are configured to support the head coil apparatus 30 on the frame 14 and to allow the head coil apparatus 30 to be adjustable along a longitudinal direction L (FIG. 1) relative to the head fixation frame 14. Each shoulder 38 includes a lower surface 38a with a longitudinally extending groove 39 formed therein that is configured to rest upon a longitudinally extending support rod associated with the head fixation frame 14. At least one of the support rods may be threaded so as to threadingly engage a respective threaded passageway formed within the head fixation frame 14.

In the illustrated embodiment, a threaded passageway 23 is formed through arcuate arm 18 and extends along a direction that is substantially parallel with the longitudinal direction L (although it need not be). Threaded head coil apparatus support rod 22 extends outwardly from both ends of the passageway 23 such that a pair of shoulders 38 on one side of the head coil apparatus 30 rests on the support rod 22. A passageway 25 is formed through arcuate arm 20 and extends along a direction that is substantially parallel with the longitudinal direction L (although it need not be). A head coil apparatus support rod 24 extends outwardly from both ends of the passageway 25 such that the other pair of shoulders 38 on the opposite side of the head coil apparatus 30 rests on the support rod 24.

Threaded support rod 22 includes an enlarged head portion 22a (FIG. 3) at one end thereof that facilitates rotation of the support rod 22 by a clinician. The enlarged head portion 22a may have a knurled circumference to facilitate gripping and rotation by a user, as would be understood by those skilled in the art. The head coil apparatus 30 is supported on threaded support rod 22 such that shoulder 38 abuts the head portion 22a. As such, clockwise rotation of the support rod 22 causes the head coil apparatus 30 to be moved one way along the longitudinal direction L. Counterclockwise rotation of the threaded support rod 22 will create a space between shoulder 38 and the enlarged head portion 22a, allowing the head coil apparatus to be moved by a clinician in the opposite way along the longitudinal direction L.

Embodiments of the present invention are not limited to the illustrated shoulders 38 and support rods 22, 24. Other ways of adjustably supporting the head coil apparatus 30 on the head fixation frame 14 may be utilized, without limitation.

Each arm 18, 20 of the head fixation frame 14 includes a respective free end 18a, 20a (FIG. 1). A head fixation member 40 is adjustably associated near each respective arm free end 18a, 20a. The head fixation members 40 are configured to engage a patient's head within the head fixation frame 14.

In the illustrated embodiment of FIG. 3, a threaded passageway 42 extends through each arcuate arm 18, 20 adjacent each respective free end 18a, 20a, as illustrated. A head fixation member 40 is threaded and is configured to threadingly engage a respective threaded passageway 42. In the illustrated embodiment, each head fixation member 40 includes opposite first and second end portions 40a, 40b. The first end portion 40a of each head fixation member has a conical shape that is configured to engage the skull of a patient's head and make sufficient contact with the skull to maintain the patient's head in a desired orientation. The second end portion 40b of each head fixation member 40 has an enlarged configuration that facilitates rotation of the head fixation member 40 by a clinician. The enlarged second end portion 40b may have a knurled circumference to facilitate gripping and rotation by a clinician, as would be understood by those skilled in the art. The head fixation members 40 may be formed from various materials (e.g., titanium, etc.) and may be disposable. Alternatively, the first end portion 40a of each head fixation member 40 may be removable (and disposable) from the remainder of the head fixation member 40. The first end portion 40a of each head fixation member 40 may be formed from various materials (e.g., titanium, etc.).

The threaded passageway 42 formed in each of the arcuate arms 18, 20 may extend along respective directions that are orthogonal to the longitudinal direction L (FIG. 1). Alternatively, the threaded passageway 42 formed in each of the arcuate arms 18, 20 may extend along a direction that is non-orthogonal to the longitudinal direction L. As such, head fixation members 40 associated with the elongated arm free ends 18a, 20a may extend along respective directions that are orthogonal to the longitudinal direction L, or may extend along respective directions that are non-orthogonal to the longitudinal direction L. For example, in some embodiments, head fixation members 40 may be angled downwardly, upwardly, forwardly, or rearwardly relative to the head fixation frame 14.

In the illustrated embodiment, a pair of additional head fixation members 44 extend outwardly from the head fixation frame surface 14a between the pair of arms 18, 20. These additional head fixation members 44 are adjustably associated with the head fixation frame 14 and are configured to engage and support a patient's head within the head fixation frame. The illustrated head fixation members 44 have a conically-shaped end portion 44a that is configured to engage the skull of a patient's head and make sufficient contact with the skull to maintain the patient's head in a desired orientation. The head fixation members 44 may be formed from various materials (e.g., titanium, etc.) and may be disposable. Alternatively, the end portion 44a of each head fixation member 44 may be removable (and disposable) from the remainder of the head fixation member 44. The end portion 44a of each head fixation member 44 may be formed from various materials (e.g., titanium, etc.).

One or more of the head fixation members 40, 44 may be particularly effective in preventing a patient's head from pivoting during fixation within the head fixation frame 14. As such, the head of a patient is secured within the head fixation frame 14 by the head fixation members 40 associated with the head fixation frame arms 18, 20 and by head fixation members 44 associated with the head fixation frame 14 between the arms 18, 20.

In some embodiments, the head fixation members 44 are threadingly engaged with the head fixation frame 14. For example, in the illustrated embodiment, a pair of threaded bosses 46 extend from the portion of the head fixation frame 14 between the arcuate arms 18, 20. A respective head fixation member 44 is threadingly engaged with each respective threaded boss 46.

The threaded bosses 46 may each have an axial direction that is orthogonal to the longitudinal direction L. Alternatively, the threaded bosses 46 may each have an axial direction that is non-orthogonal to the longitudinal direction L. As such, head fixation members 44 associated may extend along respective directions that are orthogonal to the longitudinal direction L, or may extend along respective directions that are non-orthogonal to the longitudinal direction L. For example, in some embodiments, head fixation members 44 may be angled forwardly or rearwardly relative to the head fixation frame 14.

Figure 24:
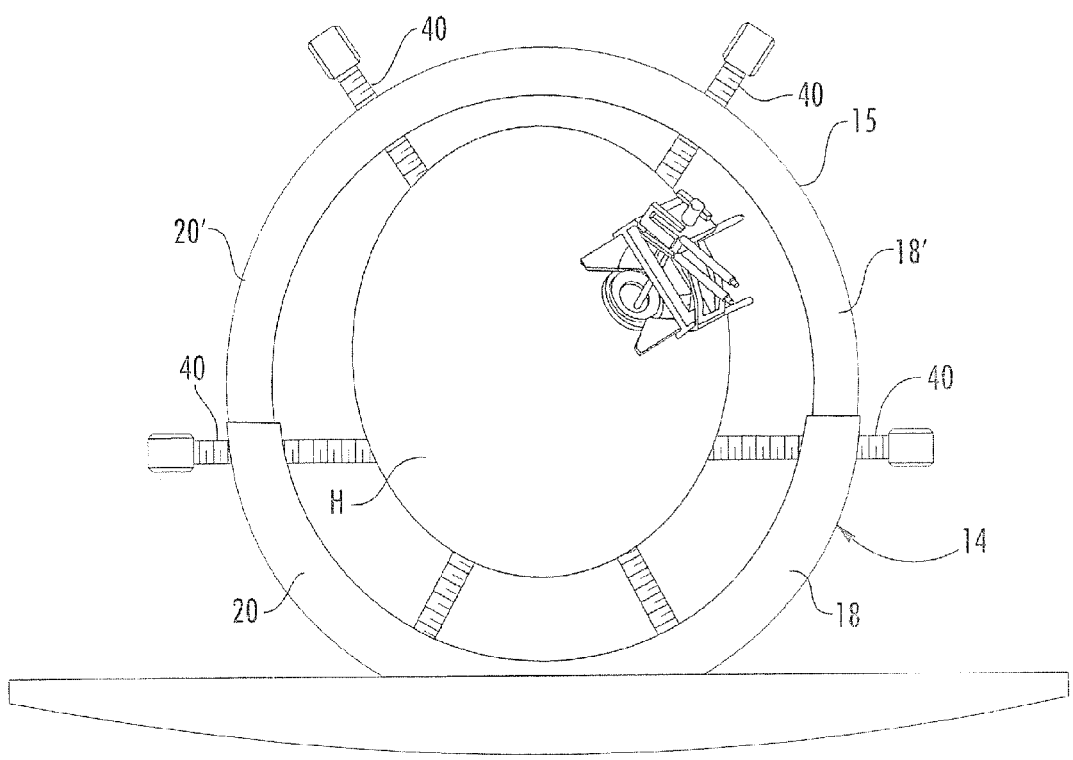
FIG. 24 is an end view of a head fixation frame of a head fixation assembly, according to other embodiments of the present invention.

Referring to FIG. 24, in some embodiments, a head fixation frame 14 can include a top portion 15 secured to arms 18, 20. The illustrated top portion 15 includes corresponding arms 18', 20' having an arcuate configuration that overlie the forehead of a patient. Thus, the illustrated head fixation frame of FIG. 24 completely surrounds the head H of a patient. A pair head fixation members 40 are adjustably associated with the top portion 15 and are configured to engage a patient's head, as illustrated.

Figure 4:
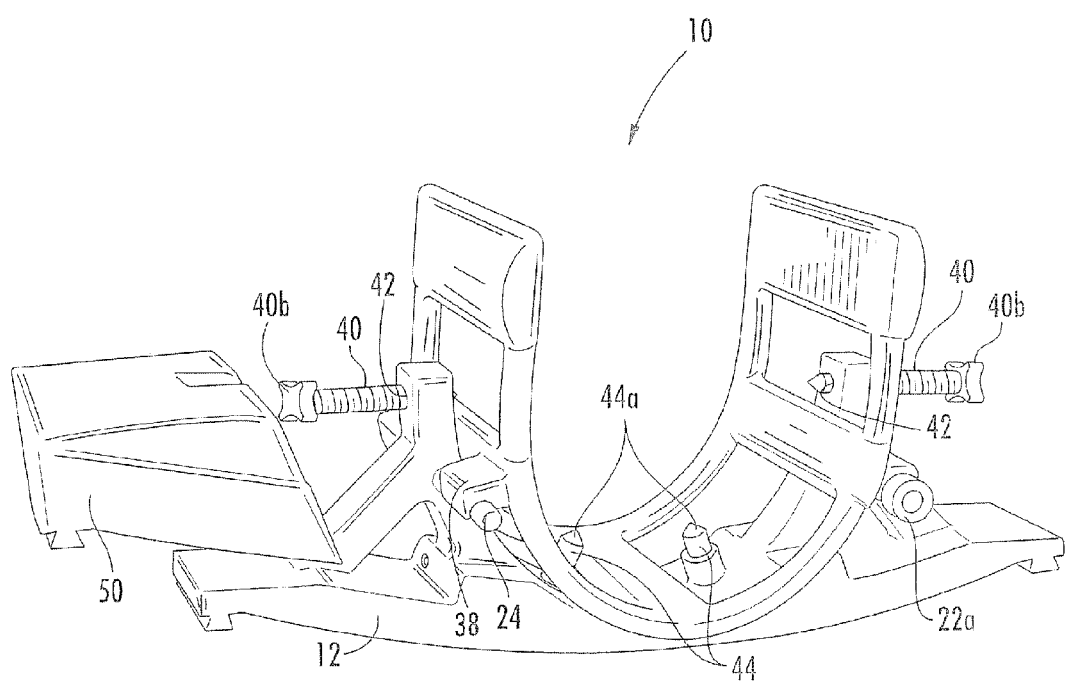
FIG. 4 illustrates a shield being removably secured to the head fixation frame of FIG. 1.
Figure 5:
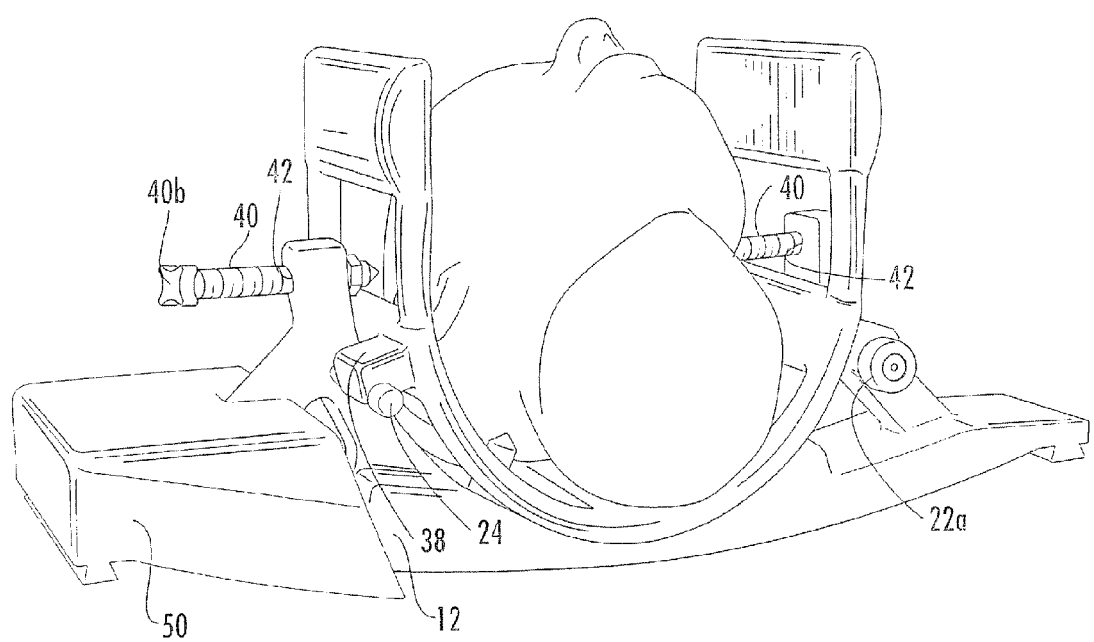
FIG. 5 illustrates the head of a patient being secured to the head fixation assembly of FIG. 3.
Figure 6:
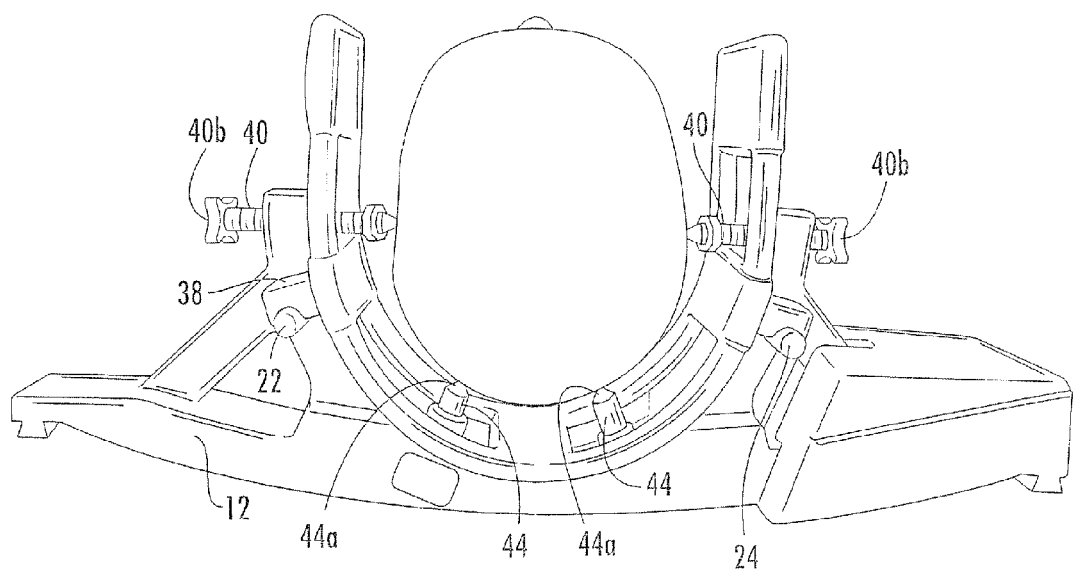
FIG. 6 is an end view of the head fixation assembly of FIG. 5 with the patient's head secured thereto.

Referring now to FIG. 4, the head fixation assembly 10 may also include a cover or shield 50 that is configured to cover electrical components, cables, and the like. In some embodiments, the shield 50 is configured to shield non-MRI compatible objects used in conjunction with the head fixation assembly 10 during an MRI-guided procedure. For example, cables and other conductive materials and devices utilized in a medical procedure can be shielded from RF excitation via the shield 50. The shield may be removably secured to the head fixation frame to facilitate access to cables and other devices used for various MRI guided procedures. In some embodiments, the shield 50 may be configured to protect against foreign material, including liquids, etc.

All of the components of the head fixation assembly 10 described above (i.e., the base 12, the head fixation frame 14, the head fixation members 40, 44, the open-face head coil apparatus 30, and the shield 50) are formed from or include MRI-compatible material. Exemplary MRI-compatible materials include, but are not limited to, various polymeric materials (e.g., plastics), carbon fiber materials, glass-filled epoxies, and metals such as nickel-titanium alloys (e.g., Nitinol). As known to those skilled in the art of MRI, Nitinol is non-ferromagnetic with a lower magnetic susceptibility than conventional stainless steel.

Figure 7:
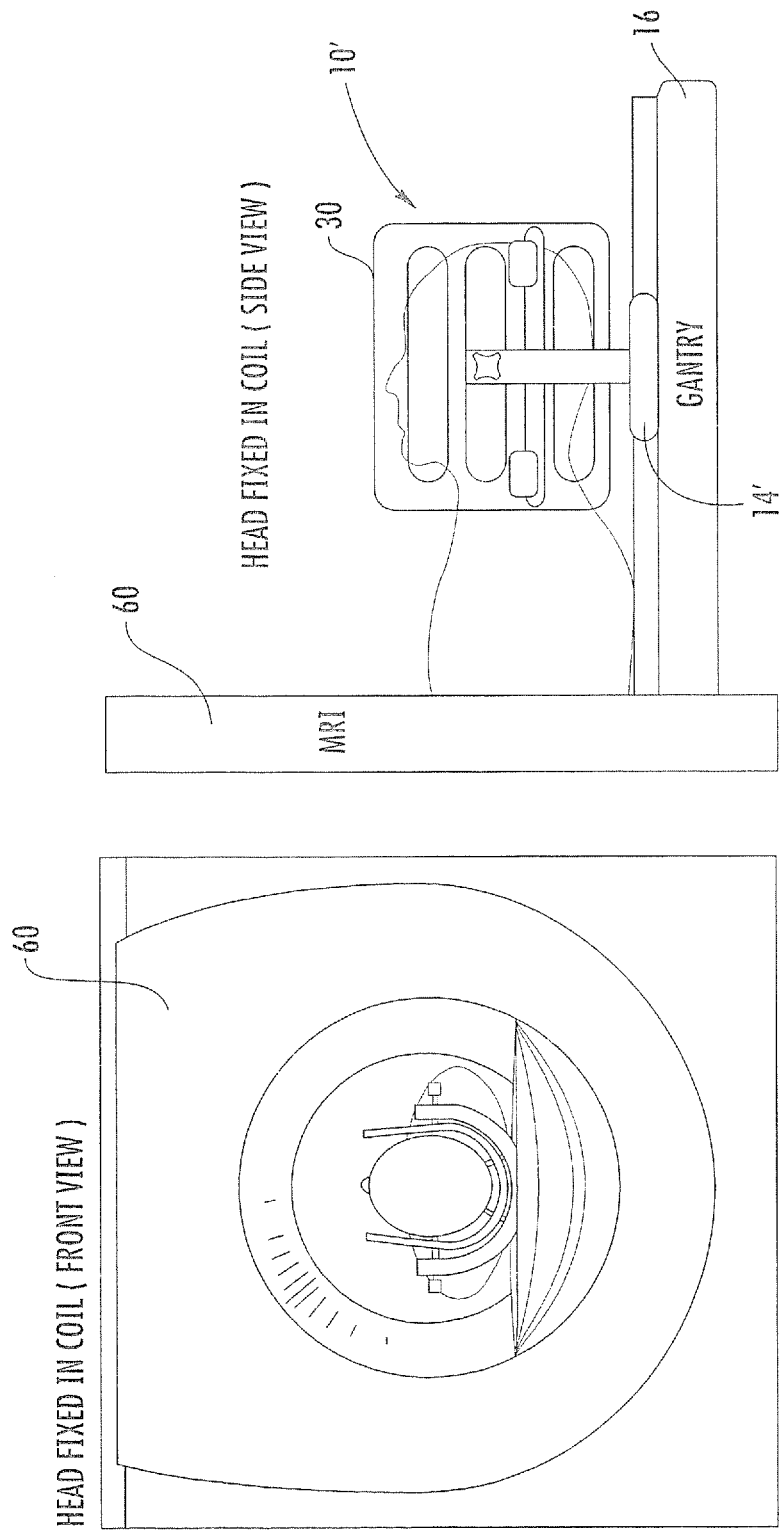
FIGS. 7A-7B are schematic illustrations of a patient on a gantry associated with the bore of an MRI scanner and wherein the head of the patient is secured to a head fixation assembly, according to some embodiments of the present invention.

FIGS. 7A-7B are schematic illustrations of a patient on a gantry associated with the bore of an MRI scanner and wherein the head of the patient is secured to a head fixation assembly 10, according to some embodiments of the present invention. The illustrated head fixation assembly 10 includes a neurosurgical head fixation frame 14' secured to the gantry 16 of an MRI scanner 60. An open-face head coil apparatus 30 is adjustably secured to the head fixation frame 14' and is positioned around the head of a patient secured to the head fixation frame 14'. The head coil apparatus 30 has an open-face U-shaped configuration as described above with respect to FIGS. 2-6.

Figure 8:
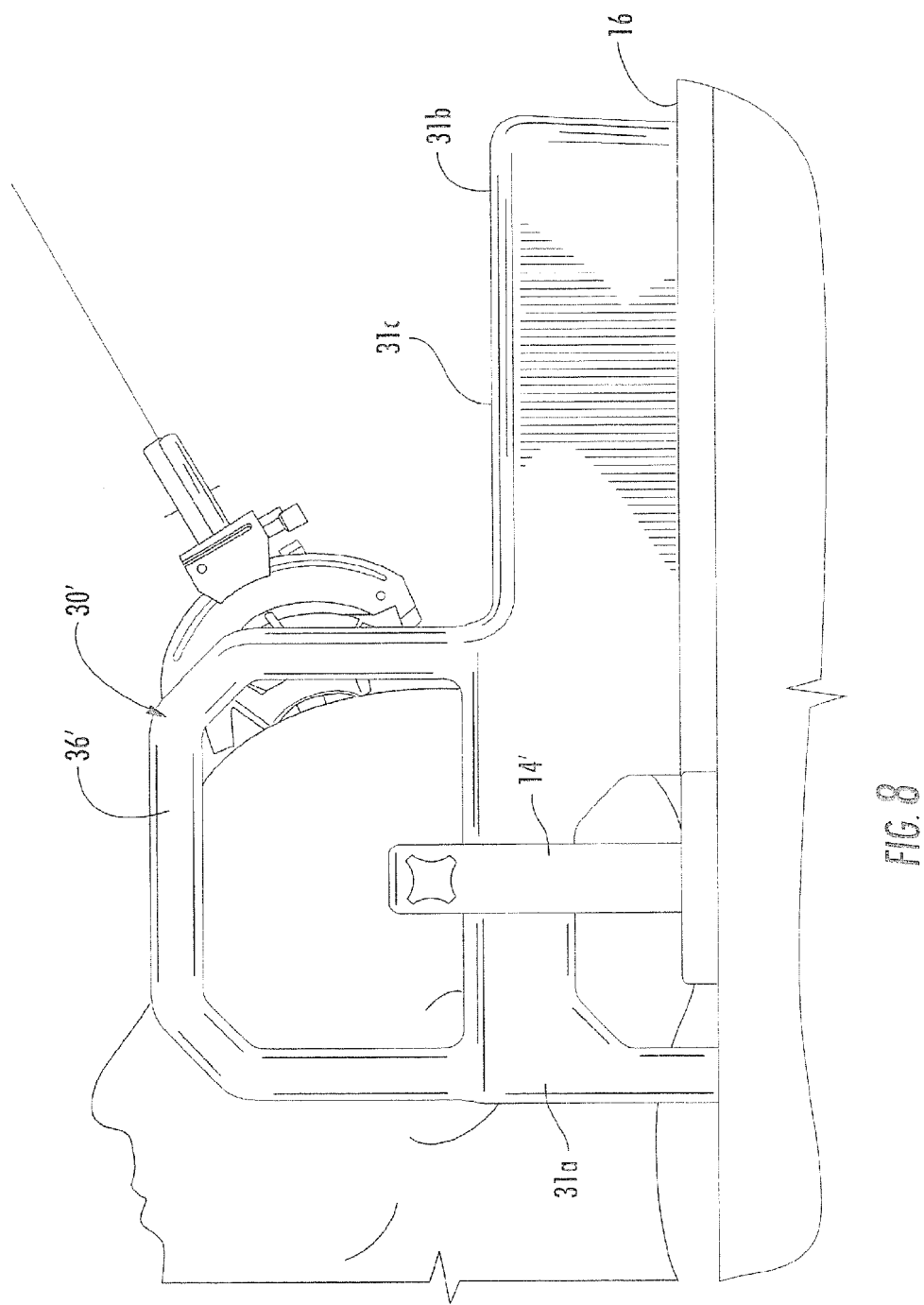
FIGS. 8-9 illustrate that open-face head coil apparatus, according to embodiments of the present invention, can accommodate targeting cannulas and other interventional devices.
Figure 9:
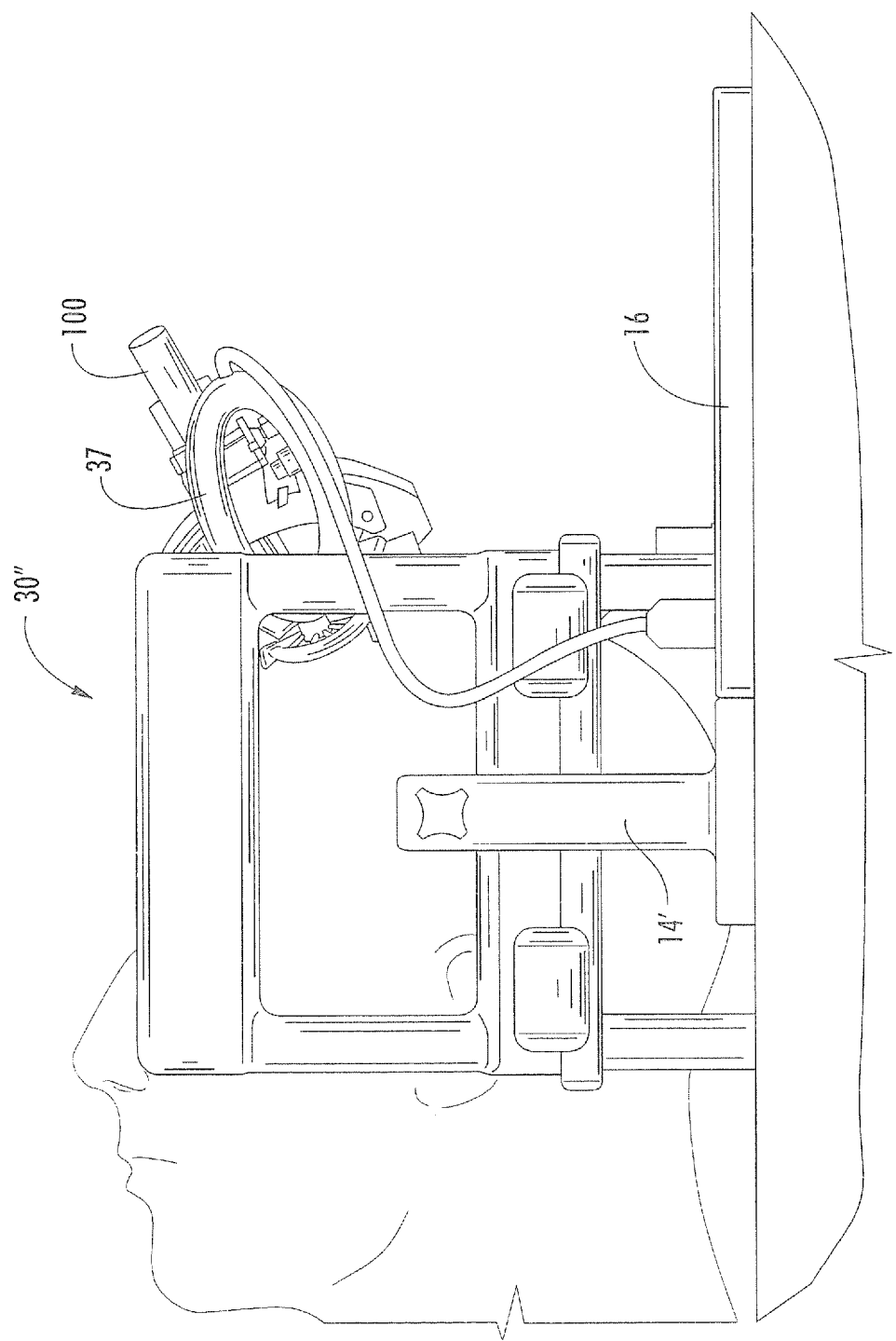
Figure 10:
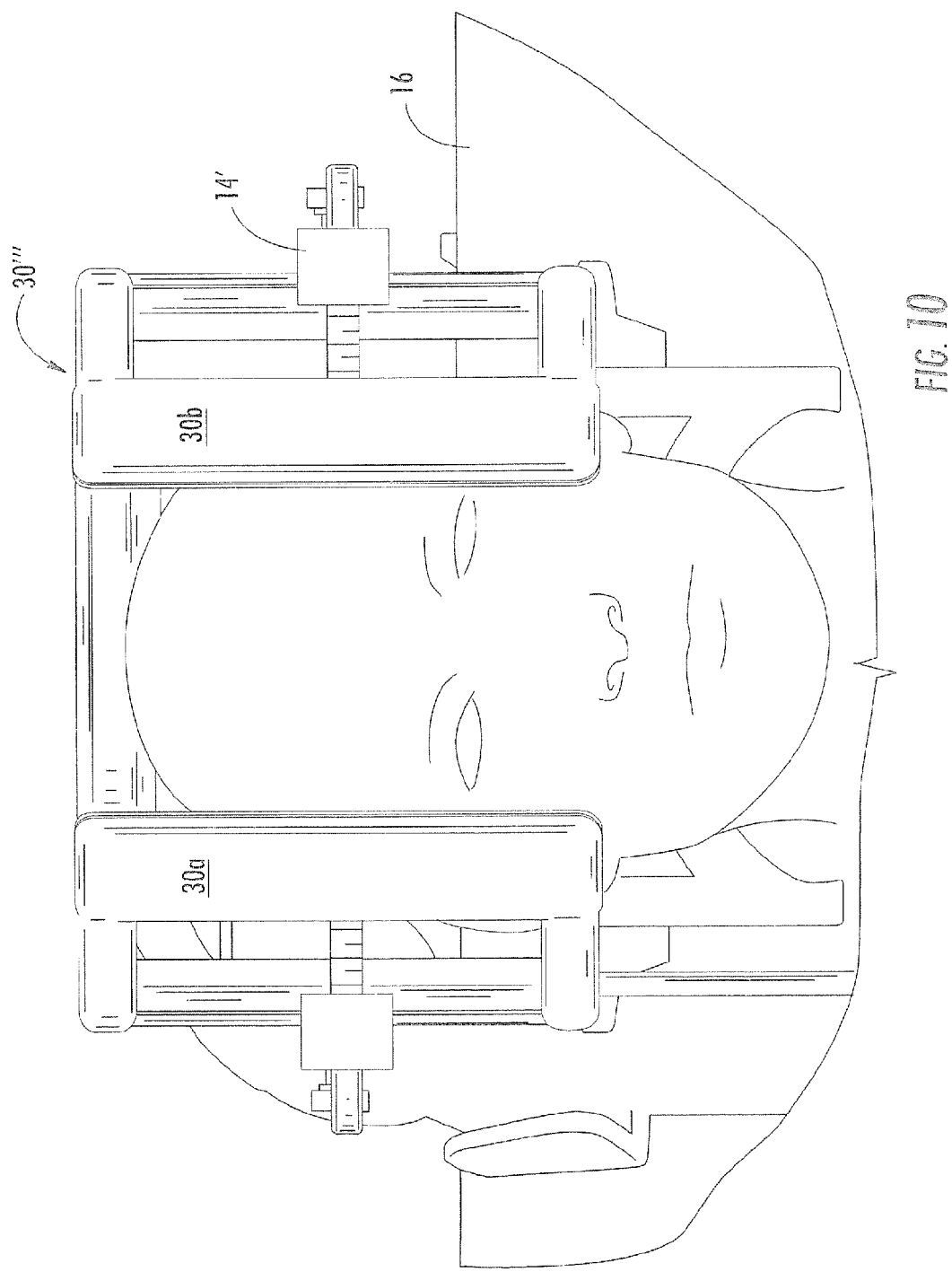
FIG. 10 illustrates an open-face head coil apparatus, according to some embodiments of the present invention.

FIGS. 8-10 illustrate open-face head coil apparatus according to various embodiments of the present invention. In FIG. 8, an open-face head coil apparatus 30' includes opposite first and second end portions 31a, 31b. The head coil apparatus first end portion 31a is positioned within the head fixation frame 14'. The head coil apparatus second end portion 31b is secured to the gantry 16 of an MRI scanner. In other embodiments, head coil apparatus second end portion 31b can be secured to a movable base configured to allow adjustment of the position of the head coil apparatus 30. The illustrated head coil apparatus 30' includes spaced-apart, upwardly extending members 36' with open side windows and having an inverted, substantially U shape. RF coils, and associated circuitry for the RF coils are contained within the upwardly extending members 36' and/or second end portion 31b. In some embodiments, the illustrated head coil apparatus 30' includes an intermediate portion 31c between the first and second end portions 31a, 31b. Intermediate portion 31c may contain additional RF coils and associated circuitry. RF coils located in intermediate portion 31c can be positioned proximate to a targeting frame and/or other interventional device. In some embodiments, electronic components, cables, and circuitry for the head coil apparatus 30' can be stored within intermediate portion 31c.

In FIG. 9, an open-face head coil apparatus 30'', similar to the head coil apparatus 30 of FIGS. 2-6, is positioned within a head fixation frame 14' and secured to the gantry 16 of an MRI scanner. A secondary RF coil 37 is provided and is positioned adjacent to a targeting frame 100 that is secured to the head of a patient. The secondary coil 37 can obtain local MRI signals and facilitates identifying the location of the targeting frame 100 during an MRI-guided procedure.

In FIG. 10, an open-face head coil apparatus 30''', similar to the head coil apparatus 30 of FIGS. 2-6, is positioned within a head fixation frame 14' and secured to the gantry 16 of an MRI scanner. The leg portions 30a, 30b of the head coil apparatus 30''' have an arcuate configuration such that each partially overlies the head of a patient.

Figure 11:
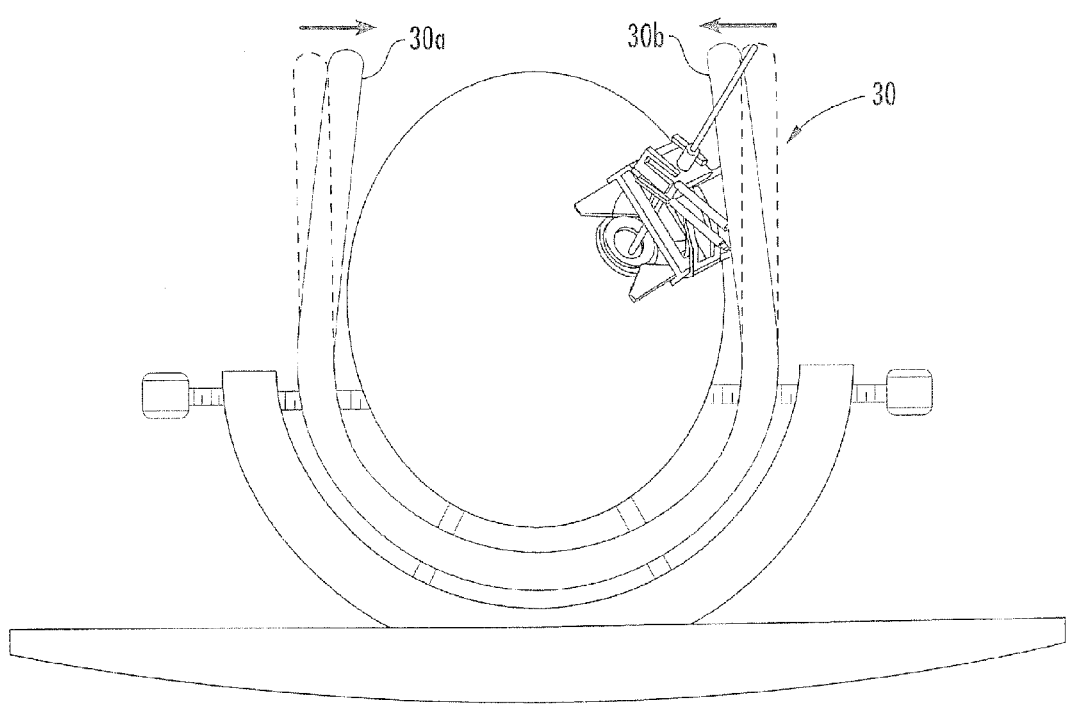
FIGS. 11-12 are schematic illustrations of a head fixation assembly wherein the legs of the open-face head coil apparatus are movable towards the head of a patient.
Figure 12:
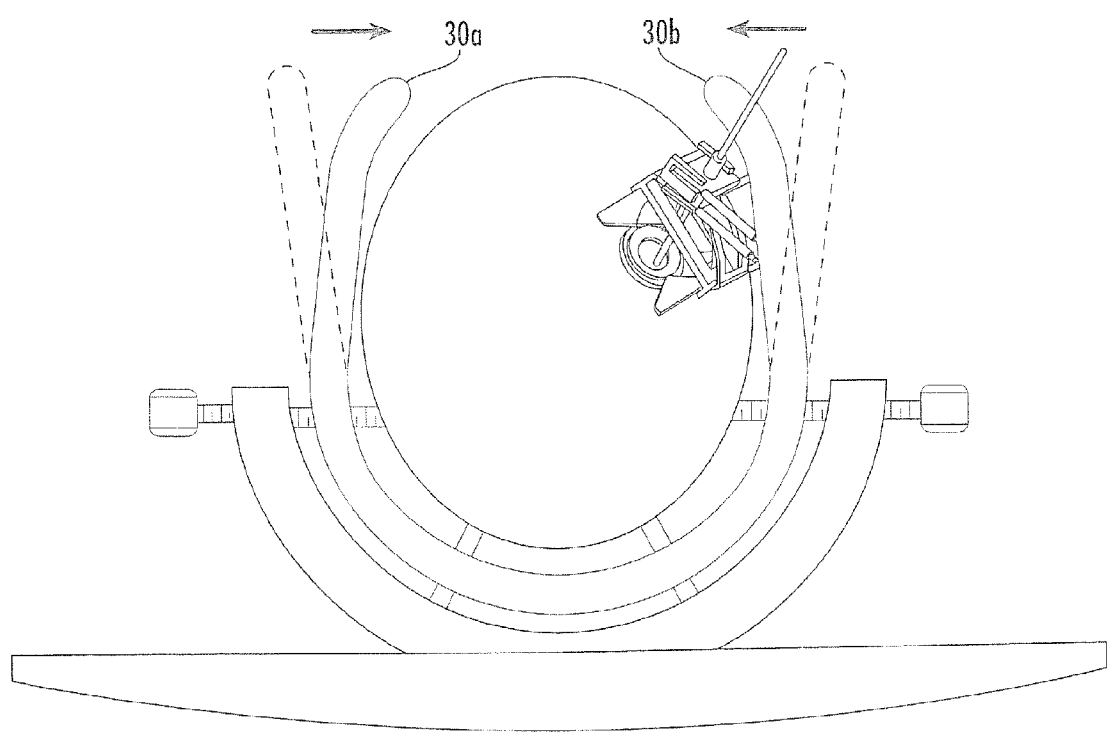

In some embodiments of the present invention, the leg portions of an open-face head coil apparatus are movable (e.g., bendable, deformable, pivotable, etc.) to permit user adjustment of the spaced-apart relationship of the leg portions 30a, 30b. For example, the leg portions 30a, 30b of head coil apparatus 30 may be configured to pivot relative to each other, as illustrated in FIG. 11. The leg portions 30a, 30b of head coil apparatus 30 may be configured to bend relative to each other, as illustrated in FIG. 12.

Figure 13:
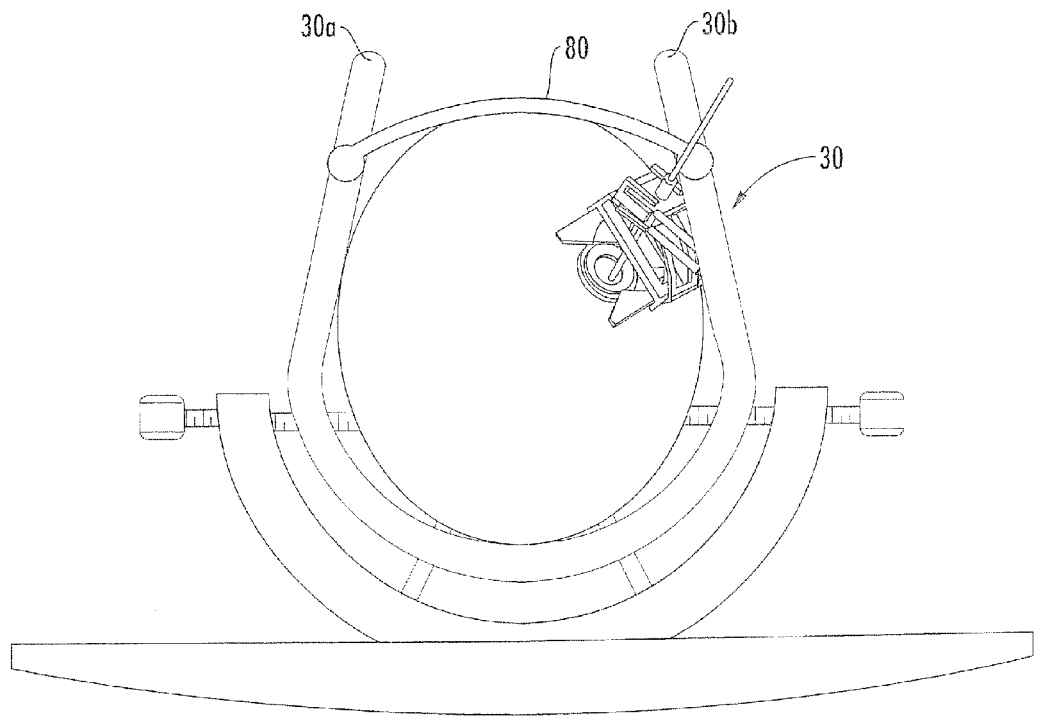
FIGS. 13-17 illustrate various embodiments of a restraint device for altering and/or maintaining the upper end portions of the legs of an open-face head coil apparatus in a particular configuration.
Figure 14:
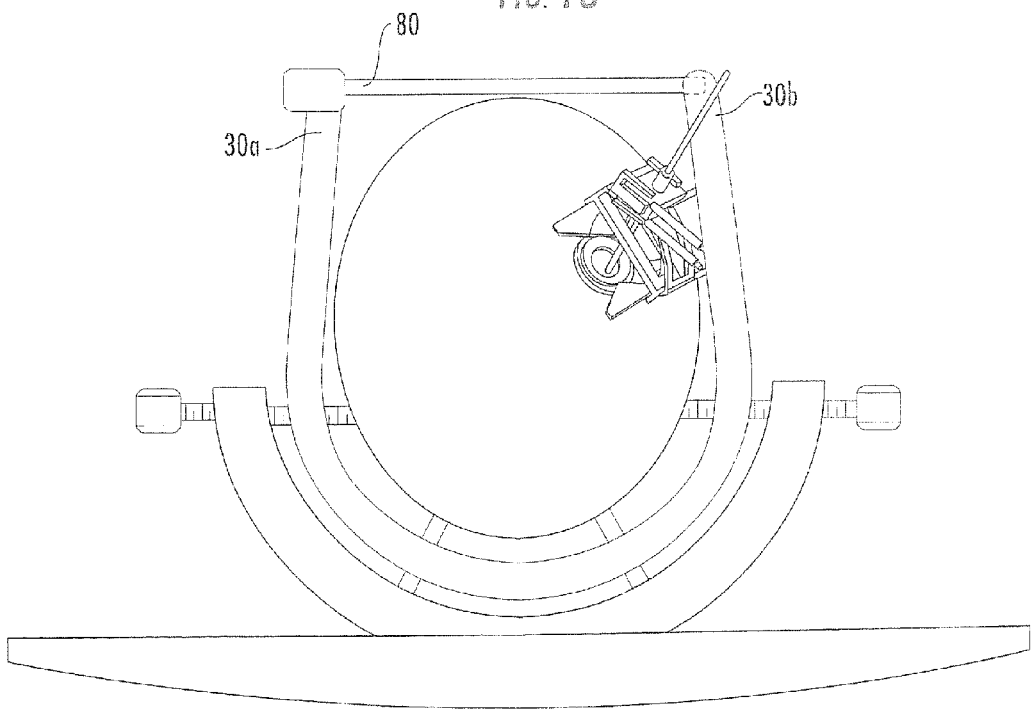
Figure 15:
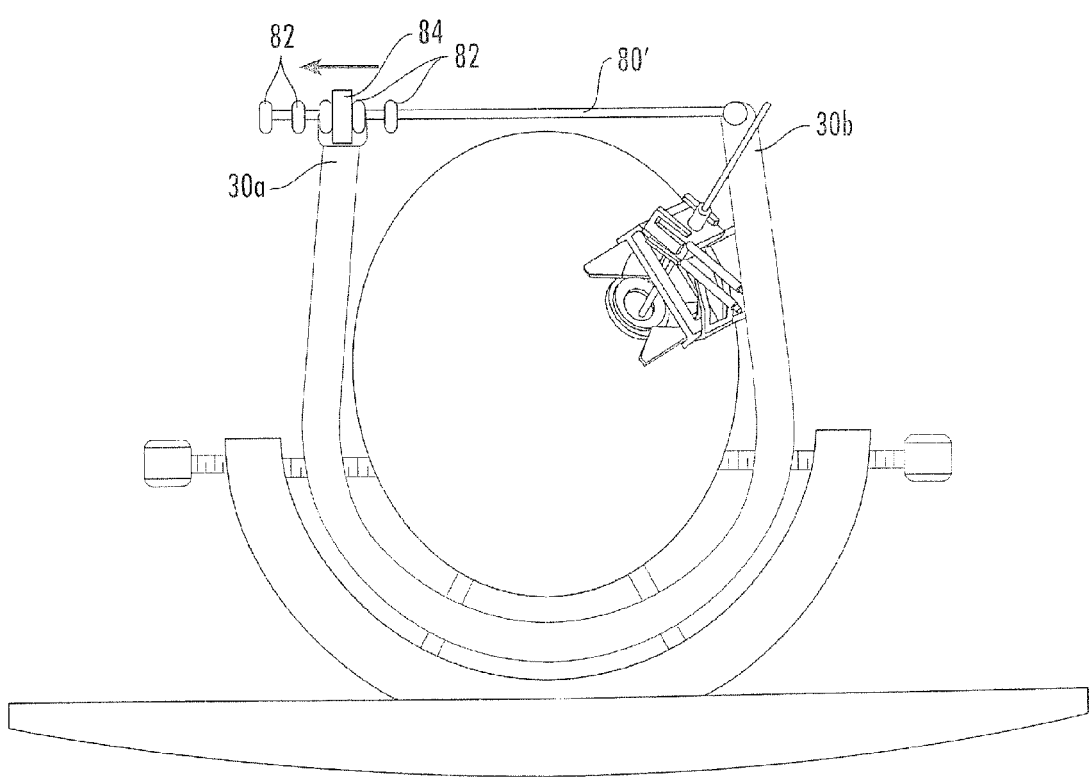

Referring now to FIGS. 13-17, a user adjustable restraining device 80 may also be attached to the respective leg portions 30a, 30b of a head coil apparatus 30 to obtain and/or maintain a user-selected spaced-apart relationship of the leg portions 30a, 30b. In some embodiments, the restraining device 80 is configured to contact a patient's head supported within the head fixation frame (FIG. 13). In other embodiments, the restraining device does not contact a patient's head. Various types of restraining devices may be utilized, without limitation. An exemplary restraining device is a flexible strap 80' configured to adjustably position leg portions 30a, 30b relative to each other, as illustrated in FIG. 15. The illustrated flexible strap 80' has one end secured to leg portion 30b. The opposite end of the flexible strap 80' includes a plurality of spaced apart notches 82 that are configured to engage with member 84 associated with leg portion 30a to maintain the flexible strap 80' at a length selected to maintain the leg portions 30a, 30b a desired distance from each other.

Figure 16:
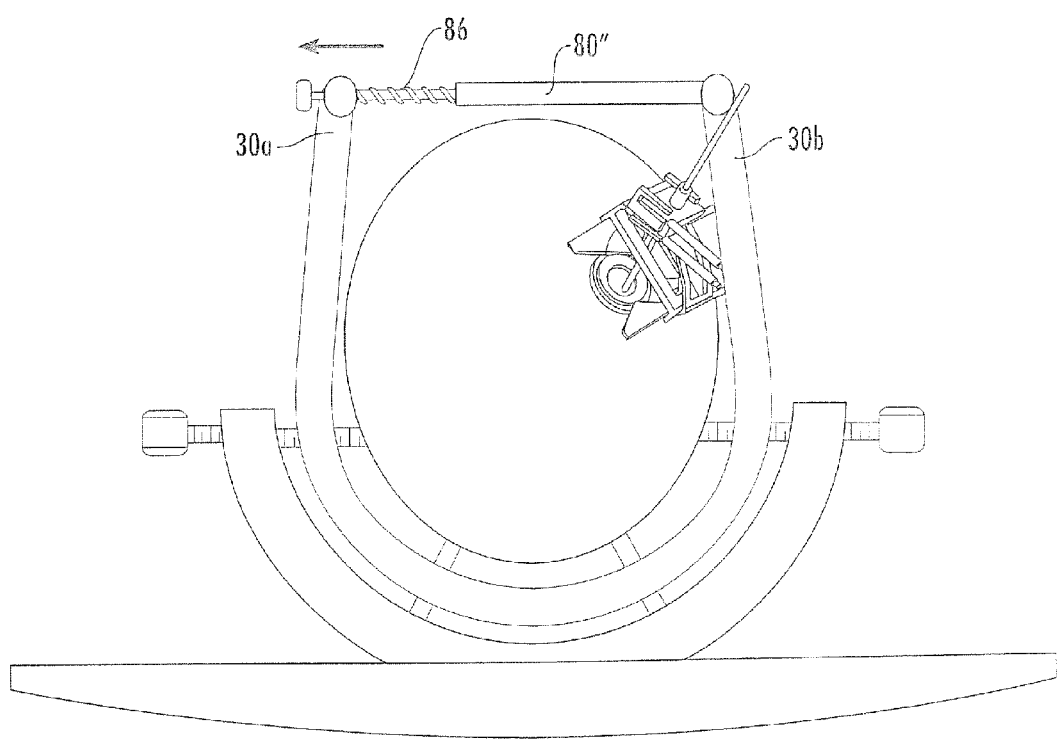

Another exemplary restraining device is a threaded member 80'' configured to adjustably position leg portions 30a, 30b relative to each other, as illustrated in FIG. 16. The illustrated threaded member 80'' has one end secured to leg portion 30b. The opposite end of the threaded member 80'' is configured to threadingly engage a threaded rod 86 that is associated with leg portion 30a. Rotation of threaded rod 86 and threaded member 80'' relative to each other is configured to move leg portions 30a, 30b relative to each other and to maintain the leg portions 30a, 30b a desired distance from each other, as would be understood by those skilled in the art.

Figure 17:
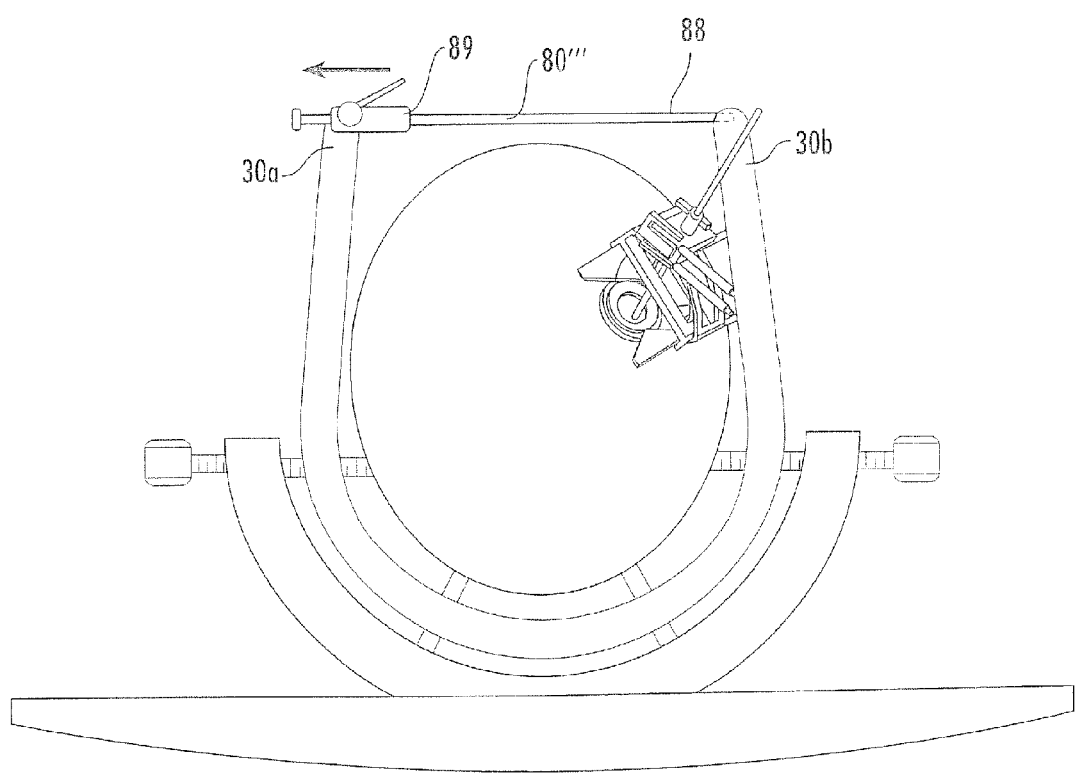

Another exemplary restraining device 80''' configured to adjustably position leg portions 30a, 30b relative to each other is illustrated in FIG. 17. The illustrated device 80''' includes an elongated member 88 having one end secured to leg portion 30b. The opposite end of the elongated member 88 is configured to be slidably received within a clamping device 89 associated with leg portion 30a. As the elongated member is pulled through the clamping device, the leg portions 30a, 30b are forced closer toward each other. Clamping device 89 is configured to maintain the leg portions 30a, 30b a desired distance from each other, as would be understood by those skilled in the art.

Figure 18:
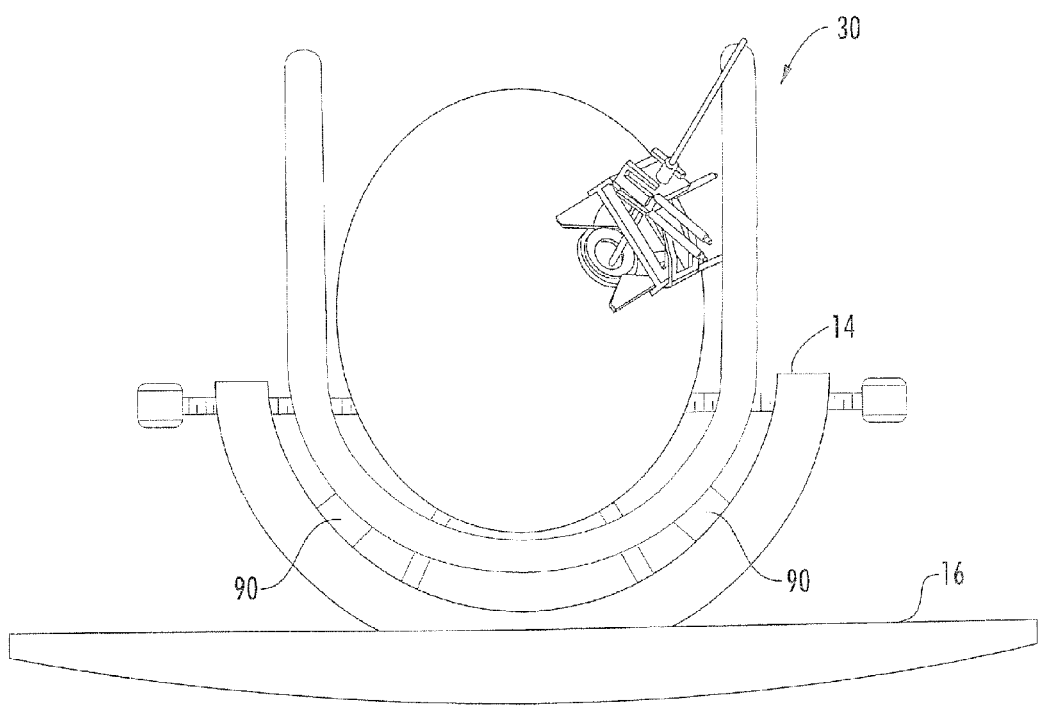
FIG. 18 is a schematic illustration of a head fixation assembly according to embodiments of the present invention and wherein shims are utilized to adjust the position of an open-face head coil apparatus relative to a head fixation frame.
Figure 21A:
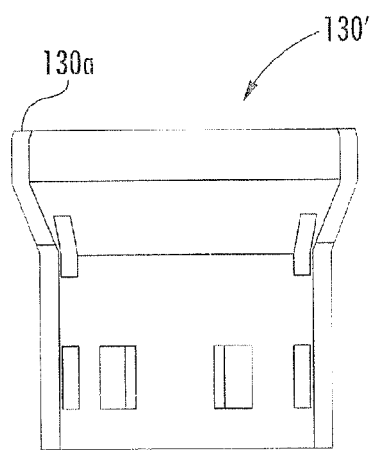
FIGS. 21A-21D are various views of an open-face head coil apparatus, according to other embodiments of the present invention.
Figure 21B:
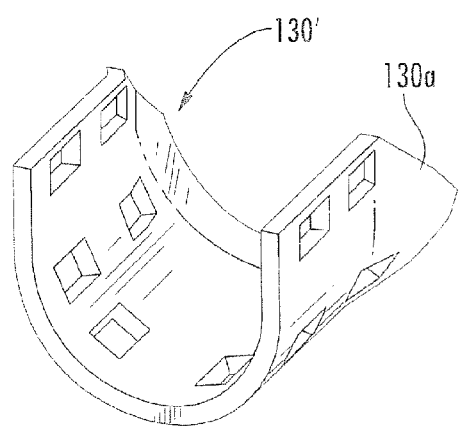
Figure 21C:
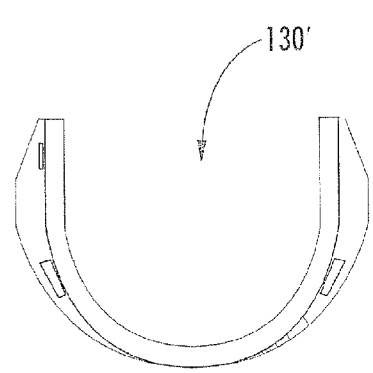
Figure 21D:
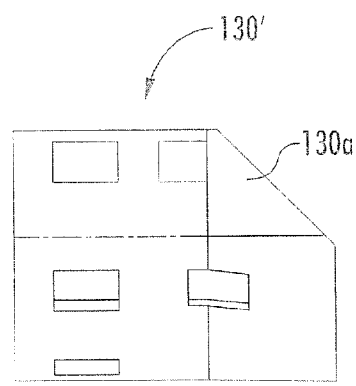
Figure 22A:
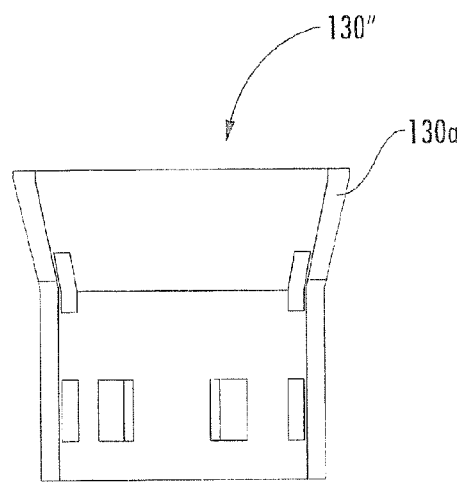
FIGS. 22A-22D are various views of an open-face head coil apparatus, according to other embodiments of the present invention.
Figure 22B:
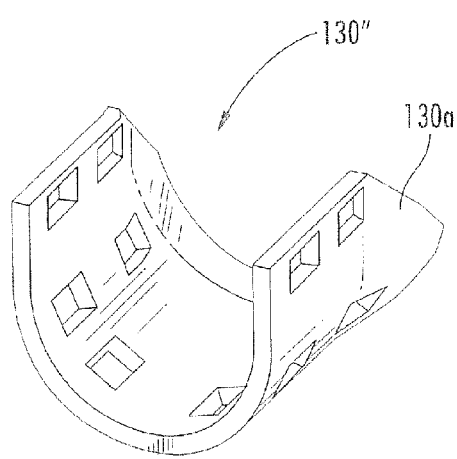
Figure 22C:
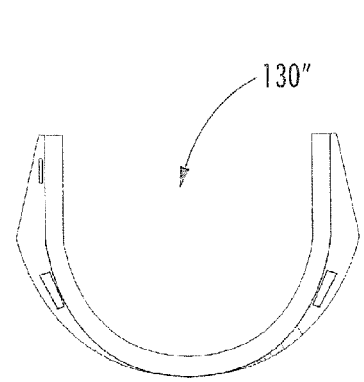
Figure 22D:
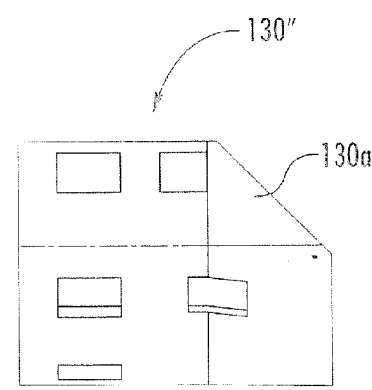

Referring now to FIG. 18, an open-face head coil apparatus 30 may be adjustable in elevation relative to a head fixation frame 14 via spacers or shims 90 positioned between the head coil apparatus 30 and head fixation frame 14. These shims 90 allow a desired space to be maintained between the head fixation frame 14 and the head coil apparatus 30 and may allow a more customizable patient-specific fit of the open-face head coil apparatus.

Referring now to FIGS. 19-20, a head fixation assembly 110 for immobilizing the head of a patient during an MRI-guided procedure, according to other embodiments of the present invention, is illustrated. The illustrated head fixation assembly 110 includes a base 12 that is configured to be removably secured to an MRI scanner gantry 16. A head fixation frame 14 is attached to the base 12. A longitudinally extending, open-face head coil apparatus 130 is also secured to the base, and is configured to surround at least a portion of a patient's head secured to the head fixation frame 14. The head coil apparatus 130 includes opposite first and second end portions 130a, 130b, with the first end portion 130a positioned within the head fixation frame 14. The head coil apparatus 130 includes a plurality of spaced-apart access windows 133 formed therein and at least one internal RF coil. The head coil apparatus 130 can include various numbers of RF coils, and the RF coils can be positioned in various locations. For example, there may be one (1) RF coil, two (2) RF coils, three (3) RF coils, five (5) Rh coils, eight (8) RF coils, etc. In some embodiments, the head coil apparatus 130 includes twelve (12) RF coils, and may be multi-channel, e.g., eight (8) channels.

The head coil apparatus 130 includes a pair of flanges (one illustrated) 131 that are used to secure the head coil apparatus to a movable portion 12' of the base 12. Threaded fasteners 132 (e.g., bolts, screws, etc.) are utilized to secure the flanges 131, and thus the head coil apparatus 130, to the base 12 as would be understood by those skilled in the art. The movable portion 12' of the base 12 is configured to move forward and backward along longitudinal direction L. Actuator 134 is configured to cause movement along the longitudinal direction L in response to rotation thereof by a user. For example, clockwise rotation of actuator 134 can cause movement of the head coil apparatus 130 along direction L (e.g., forward or backward movement), and counterclockwise rotation of actuator 134 can cause movement of the head coil apparatus 130 along direction L (e.g., forward or backward movement).

A plurality of head fixation members 40, 44 are adjustably associated with the head fixation frame 14, as described above, and are configured to engage and support a patient's head within the head fixation frame 14. Each rod 40, 44 extends through a respective access window 133 of the head coil apparatus 130. The head coil apparatus second end portion 130b is configured to shield electronics, cables, etc. associated with the head coil apparatus 130 and extends in a direction away from the patient's head and torso.

A patient tie-down strap 135 is also illustrated in FIG. 19. This strap 135 is configured to extend over the head of a patient and over the head coil apparatus 130, and can be used to help secure the head of a patient and/or the head coil apparatus 130 and prevent movement thereof. A slot 136 in the MRI gantry 16 is also illustrated and may be utilized to receive straps for securing the head coil apparatus 130 to the MRI gantry 16, as will be described below.

FIGS. 21A-21D and 22A-22D are various views of open-face head coil apparatus 130', 130", according to other embodiments of the present invention. Each of the illustrated head coil apparatus 130', 130" is similar in structure to the head coil apparatus 130 of FIGS. 19-20, and each head coil apparatus 130', 130" is configured to be positioned within a head fixation frame, as described above. However, head coil apparatus 130', 130" each have a respective tapered or flared end portion 130a, as illustrated. The tapered or flared end portion 130a facilitates access to a patient by a physician/clinician.

Figure 23:
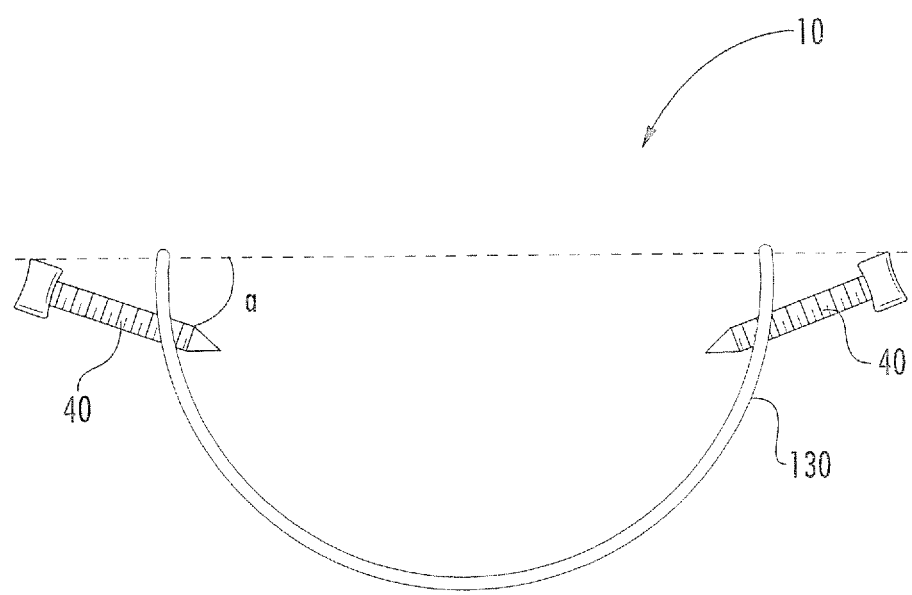
FIG. 23 is an end view of a head fixation assembly, according to some embodiments of the present invention, and illustrating an angled configuration of head engagement rods.

FIG. 23 is an end view of a head fixation assembly 10, according to some embodiments of the present invention, and illustrating that head fixation members 40 may have an angled configuration. For example, the head fixation members 40 may have an angle a relative to horizontal between about zero degrees and thirty degrees (0°-30°), and more particularly between about zero degrees and fifteen degrees (0°-15°).

Each of the illustrated head coil apparatus 30, 30', 30", 30''', 130 have an open-face and open end configuration. For example, as illustrated in FIG. 10, the head coil apparatus 30''' does not have a member extending between the two leg portions 30a, 30b or across the end portions. As such, the open-face and open end configuration of each of the illustrated head coil apparatus embodiments allows one or more targeting cannula and other interventional devices to project out of the head of a patient and into the bore of an MRI scanner magnet without being restricted. In other words head coil apparatus according to embodiments of the present invention do not interfere with interventional devices in the way that conventional head coil apparatus do.

Figure 25A:
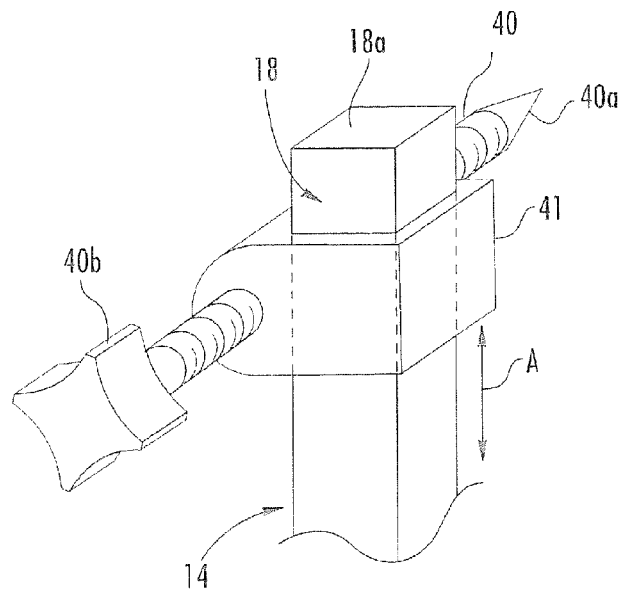
FIGS. 25A-25B are partial perspective views of head fixation frames, according to some embodiments of the present invention, illustrating variable position head engagement rods.
Figure 25B:
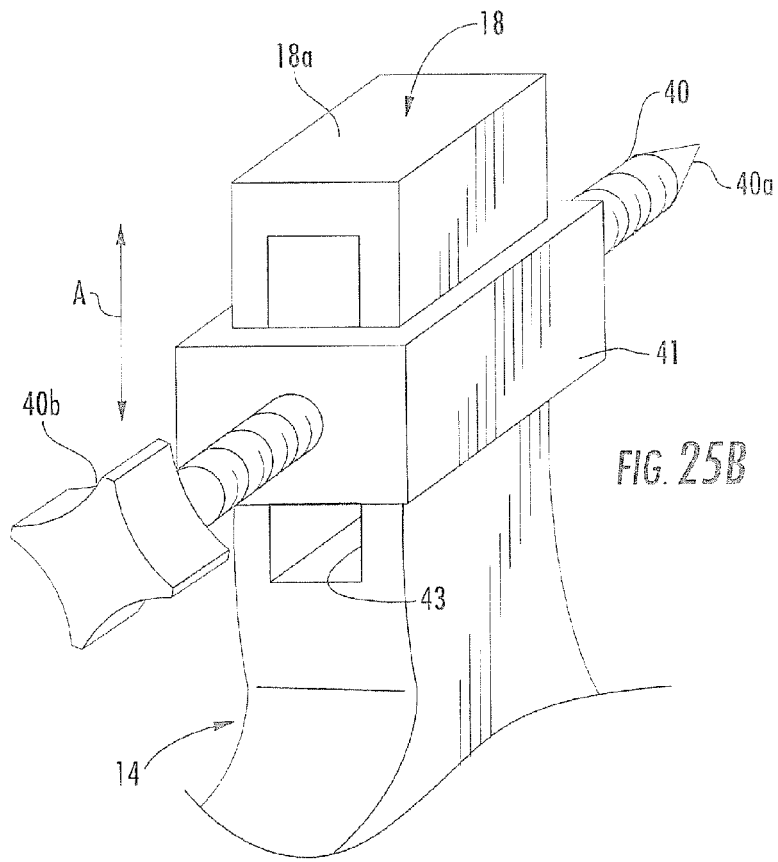

Referring to FIGS. 25A-25B, head fixation frames, according to some embodiments of the present invention, can have variable position head fixation members 40. For example, in FIG. 25A, a head fixation member 40 is movably secured to an arm 18 of a head fixation frame 14 via a collar 41. The illustrated collar 41 cooperates with the arm and is slidable along the arm as indicated by arrow A (e.g., up and down) relative to the arm free end 18a. Thus the head fixation member 40 is movable proximally and distally relative to (e.g., toward and away from) the free end 18a of the arm 18. A head fixation member 40 is threadably associated with the collar 41 and is utilized to engage the head of a patient as described above. Collar 41 can include a locking device (not illustrated), such as a set screw or bolt, for securing the collar 41 in a particular position on the arm 18. By sliding relative to the arm 18, collar 41 allows the head fixation member to have variable positions, thereby facilitating engagement with different size heads of patients. Both head fixation members 40 associated with a head fixation frame 14 can be slidable relative to a respective arm as illustrated in FIG. 25A. It is noted that the head fixation members 40 could be angled relative to horizontal between about zero degrees and thirty degrees (0°-30°), and more particularly between about zero degrees and fifteen degrees (0°-15°).

In FIG. 25B, a head fixation member 40 is movably secured to an arm 18 of a head fixation frame 14 via a collar 41. The illustrated collar 41 cooperates with the arm and is slidable along the arm as indicated by arrow A (e.g., up and down) relative to the arm free end 18a. Thus the head fixation member 40 is movable proximally and distally relative to (e.g., toward and away from) the free end 18a of the arm 18. A head fixation member 40 is threadably associated with the collar and is utilized to engage the head of a patient as described above. The arm 18 includes a slot 43 formed therethrough, as illustrated. The head fixation member 40 extends through the slot 43 as illustrated. Collar 41 can include a locking device (not illustrated), such as a set screw or bolt, for securing the collar 41 in a particular position on the arm 18. By sliding relative to the arm 18, collar 41 allows the head fixation member to have variable positions, thereby facilitating engagement with different size heads of patients. It is noted that the head fixation members 40 could be angled relative to horizontal between about zero degrees and thirty degrees (0°-30°), and more particularly between about zero degrees and fifteen degrees (0°-15°).

Figure 26:
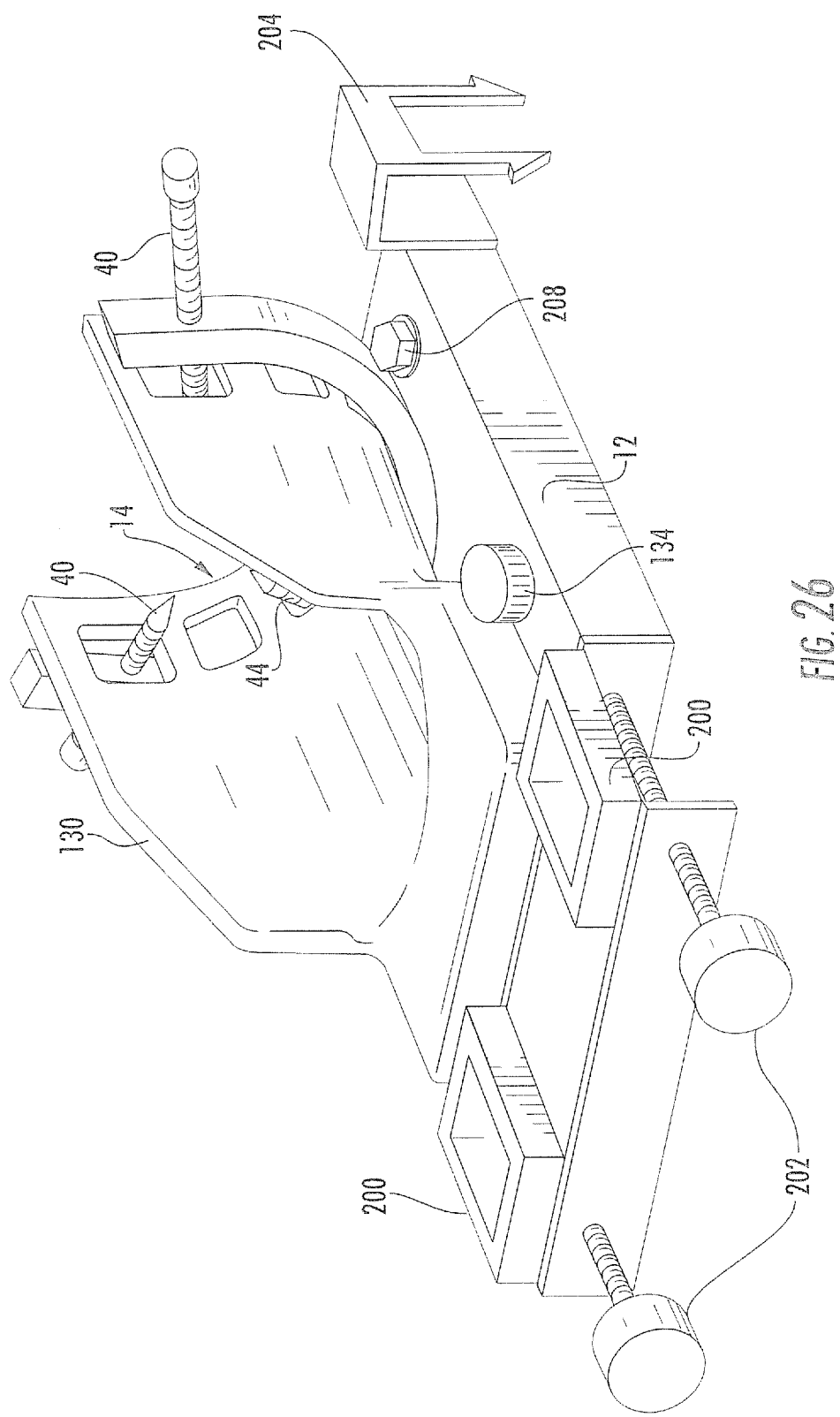
FIG. 26 is a perspective view of a base for a head fixation frame and head coil apparatus, according to some embodiments of the present invention.

FIG. 26 is a perspective view of a base 12 for a head fixation frame and head coil apparatus, according to some embodiments of the present invention. MRI scanner manufacturers use different table/gantry configurations and there are different table/gantry configurations for different models by the same MRI scanner manufacturer. The illustrated base 12 is configured to have a head fixation frame 14 and head coil apparatus 130 secured thereto. The base 12 is intended to be a "universal" base that is configured to be secured to different table/gantry configurations. In addition to the head fixation frame 14 and head coil apparatus 130, the base 12 also includes a pair of camera holders 200 for receiving MRI-compatible cameras therein. The illustrated base 12 includes a pair of mounting threaded members 202 (e.g., screws) in spaced-apart relationship. Mounting threaded members 202 are configured to lock the rear of the base 12 to an MRI scanner table/gantry. The illustrated base also includes one or more adjustable clips 204 that are configured to fasten the front of the base 12 to an MRI scanner table/gantry. For example, the clips 204 may be configured to engage slots 136 illustrated in FIG. 19. The illustrated clips 204 extend outwardly from the base 12. Adjustable straps may also be utilized in lieu of or in conjunction with the clips 204. The clips 204 may have various adjustments to facilitate securing the base to the table/gantry of different MRI scanners. The clips 204 and mounting threaded members 202 can individually or collectively be referred to as adjustable fasteners that facilitate securing the base 12 to different types of gantries (e.g., gantries of different MRI scanner models, different manufacturers, etc.).

The illustrated base 12 also includes an actuator 134 for adjusting the head coil apparatus relative to the head fixation frame 14 and/or the head of a patient. One of the bolts 208 securing the head fixation frame 14 to the base 12 is also illustrated.

Figure 27:
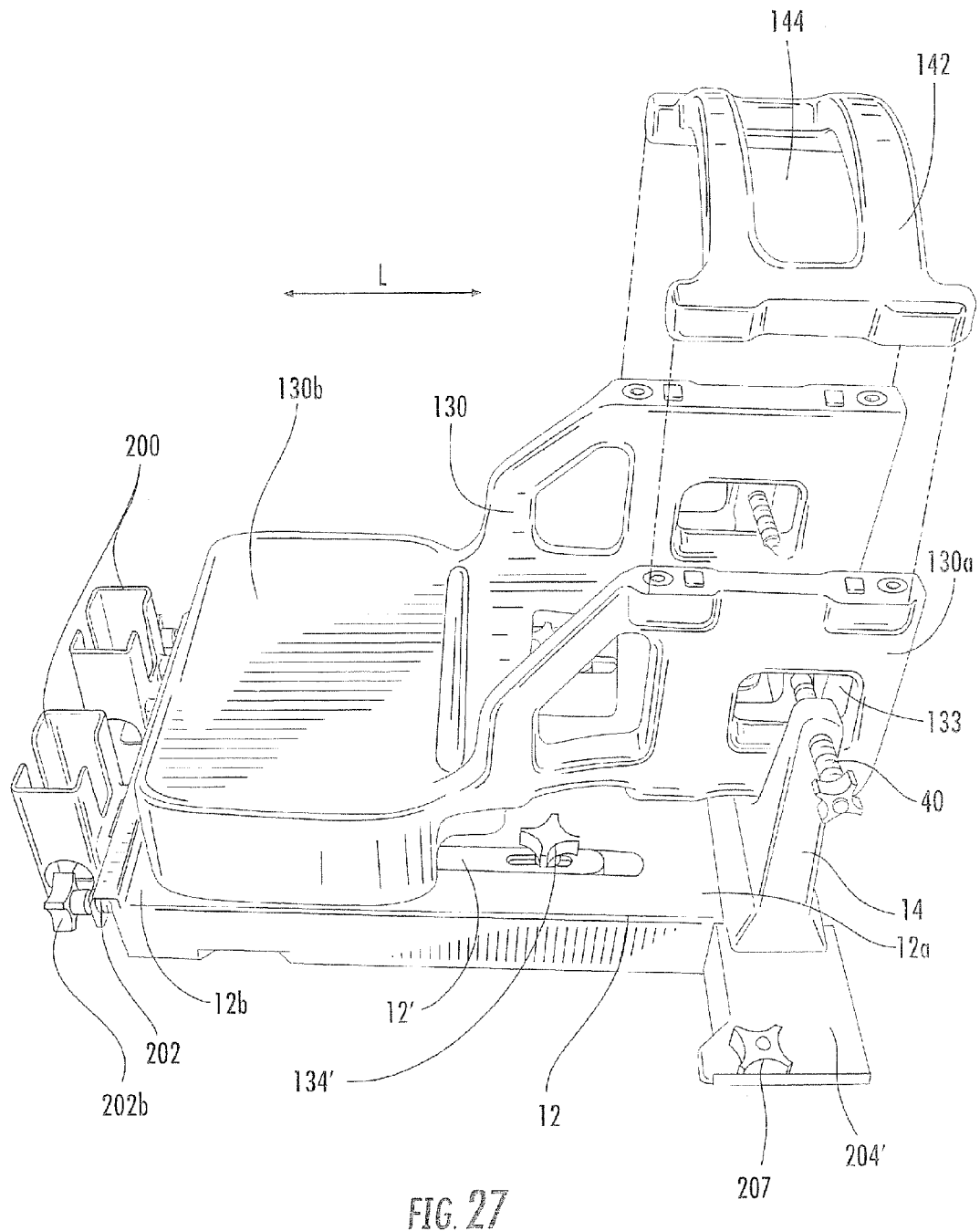
FIG. 27 is a side perspective view of a head fixation assembly including a head fixation frame attached to a base and a head coil apparatus secured to the base, according to some embodiments of the present invention.
Figure 28:
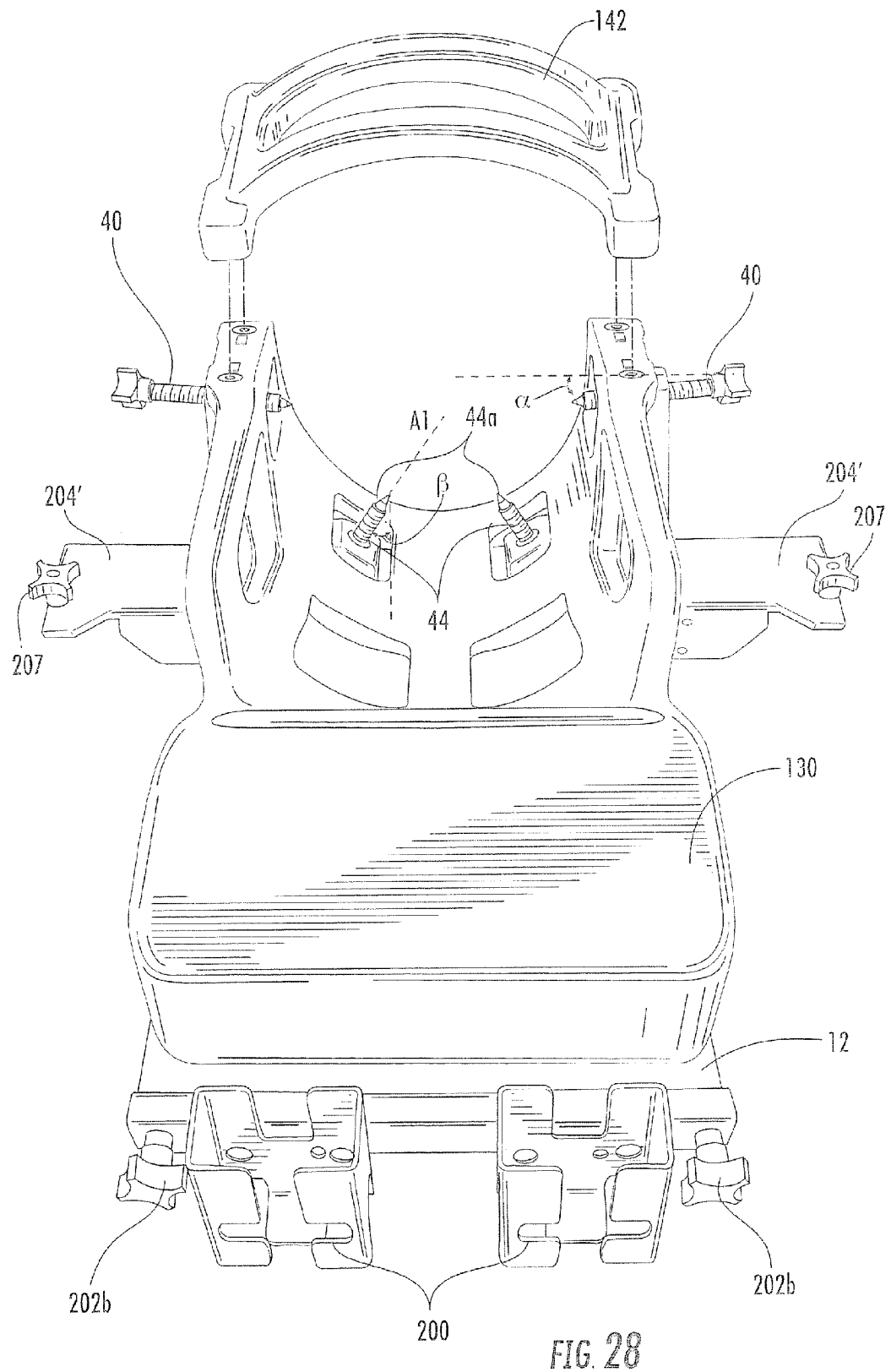
FIG. 28 is an end perspective view of the head fixation assembly of FIG. 27.
Figure 29:
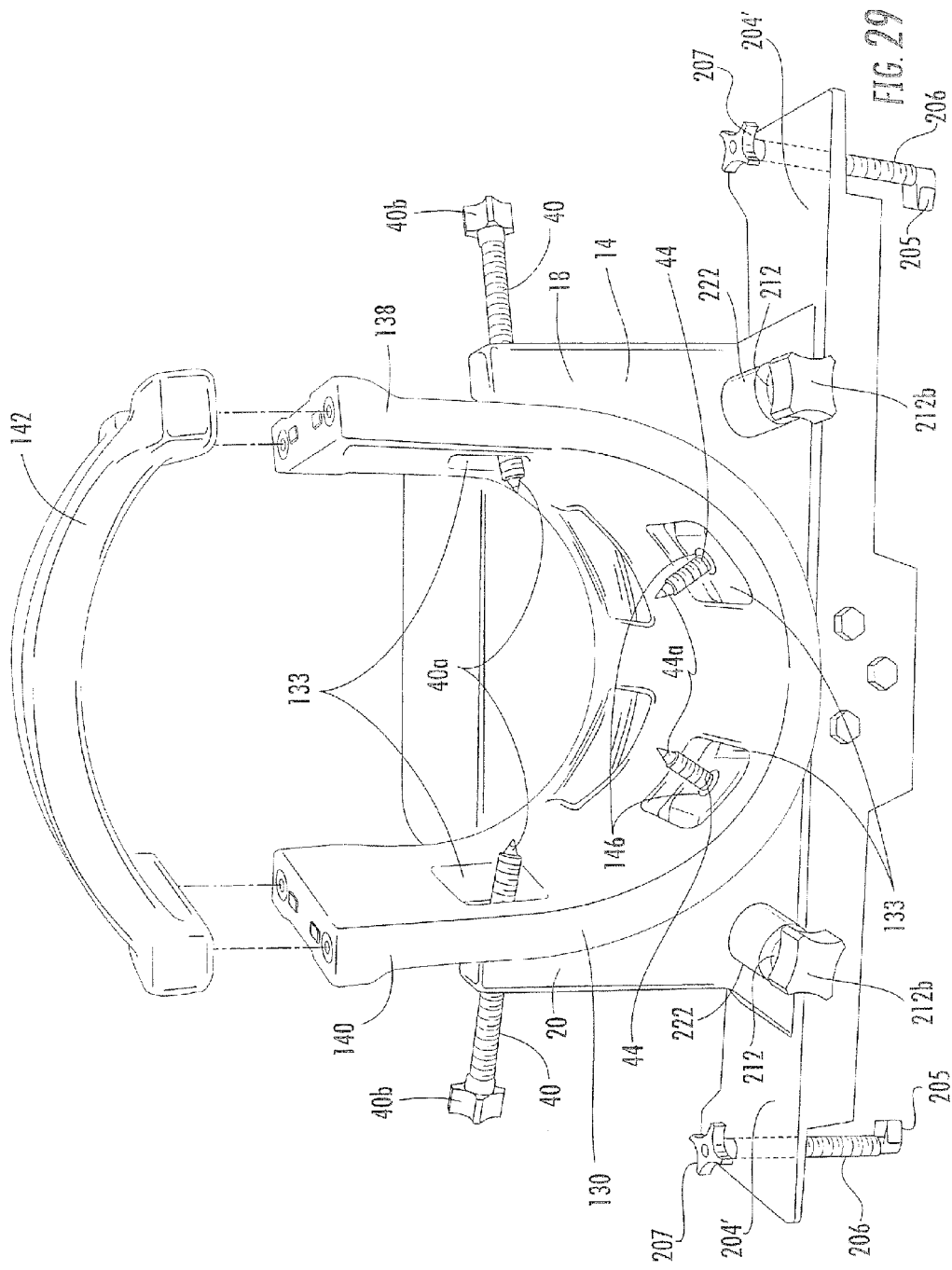
FIG. 29 is an opposite end perspective view of the head fixation assembly of FIG. 28.

FIGS. 27-34 illustrate head fixation assemblies for holding the head of a patient during medical procedures according to various embodiments of the present invention. The head fixation assemblies include a head fixation frame 14. The head fixation frame 14 includes a pair of upwardly extending spaced-apart arms 18, 20 defining a free space therebetween (FIG. 29).

Figure 31:
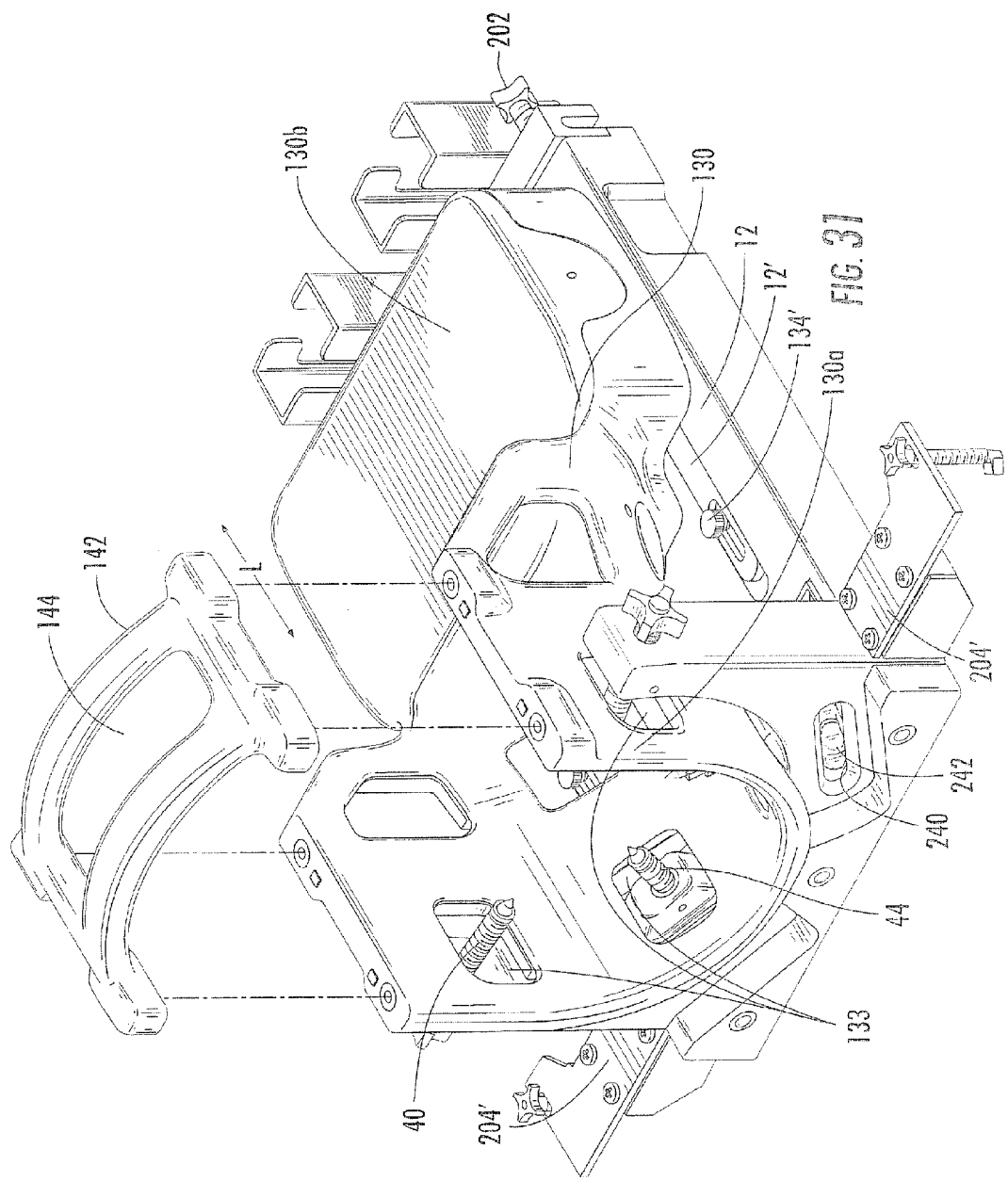
FIG. 31 is perspective view of a head fixation assembly including a head fixation frame attached to a base and a head coil apparatus secured to the base, according to some embodiments of the present invention.

In some embodiments, and as illustrated at FIGS. 27, 28, and 31, the head fixation assemblies include a base 12. The base 12 is configured to have a head fixation frame, such as the head fixation frame 14, attached thereto. In some embodiments, the head fixation frame 14 is removably or releasably attached to the base 12 such that the head fixation frame 14 may be removed for cleaning, repair, replacement, or the like. In other embodiments, the head fixation frame 14 is integrally attached to the base 12.

In some embodiments, the base 12 and/or the head fixation frame 14 includes fasteners that removably secure the base 12 and/or the head fixation frame 14 to a gantry, such as a gantry associated with an MRI scanner. The fasteners may include a plurality of rear mounting threaded members 202 in a spaced-apart relationship. As shown, a pair of rear mounting threaded members 202 are threadingly engaged with the base 12 and configured to releasably lock a rear portion 12b of the base 12 to the gantry. In some embodiments, the rear mounting threaded members 202 are screws. In some embodiments, an end portion 202b of each rear mounting threaded member 202 has an enlarged configuration (e.g., thumb wheel) that facilitates rotation of the rear mounting threaded members 202 by a clinician. The enlarged end portions 202b may have knurled circumferences to facilitate gripping and rotation by a clinician, as would be understood by those skilled in the art.

The fasteners may also include a pair of side mounting assemblies 204' on opposite sides of the base 12 at a position that is longitudinally spaced apart from the rear mounting threaded members 202. The side mounting assemblies 204' may be configured to releasably lock the base 12 to the gantry. In some embodiments, the side mounting assemblies 204' are located on opposite sides of the base 12 at a front portion 12a of the base 12. Each of the side mounting assemblies 204' typically include a downwardly extending portion adapted to engage the gantry and thereby releasably lock the sides of the base 12 and/or the sides of the head fixation assembly to the gantry. In the embodiment illustrated at FIG. 29, the side mounting assemblies 204' include a threaded member 206 (e.g., a screw) with an upwardly extending rotatable handle 207 attached to one end of the threaded member 206 and a clip 205 attached to the opposite end of the threaded member 206. In operation, the handle 207 is rotated to advance and retract (e.g., lower and raise) the clip 205. The clips 205 may be configured to engage slots in the gantry and/or fit underneath the gantry, thereby securing at least a portion of the base 12 and/or the head fixation frame 14 to the gantry.

The rear mounting threaded members 202 and/or the side mounting assemblies 204' may allow for a "universal" base that is configured to be secured to different table/gantry configurations (for example, gantries from different gantry manufacturers). In some embodiments, the head fixation assembly may be a modular head fixation assembly and side mounting assemblies, such as the side mounting assemblies 204', may be releasably attached to the head fixation frame 14, as described in more detail below. In some embodiments, the head fixation assembly may be a modular head fixation assembly and may include a base having downwardly extending portions configured to engage respective slots or grooves formed within the gantry, as described in more detail below.

The base 12 may optionally also include a removable or integral head coil apparatus, such as the head coil apparatus 130, secured thereto. As shown in FIG. 27, the head coil apparatus 130 includes opposite first and second end portions 130a, 130b, with at least a portion of the first end portion 130a extending inside the free space of the head fixation frame 14 when the head coil apparatus 130 is secured to the base 12. The head coil apparatus 130 includes a plurality of spaced-apart access windows 133 formed therein and at least one internal RF coil, as described above.

Referring to FIG. 27, in some embodiments, the head coil apparatus 130 is adjustably secured to the base such that the head coil apparatus 130 is adjustable along a longitudinal direction L relative to the head fixation frame 14. In some embodiments, the head coil apparatus 130 is adjustable between about 1 millimeter and 10 centimeters, and typically between about 1 millimeter and 3 centimeters, along the longitudinal direction L. The base 12 may include at least one movable portion 12' to facilitate longitudinal adjustment, as described in more detail above. The base 12 and/or the movable portion 12' may include at least one lock 134' configured to inhibit longitudinal movement of the head coil apparatus 130 along the longitudinal direction L. In some embodiments, each of a pair of locks 134' is positioned on an opposite side of the head coil apparatus 130 to provide access from either side of the gantry to which the base 12 is secured. In some embodiments, the lock(s) 134' are rotatable. In this regard, rotation of a lock 134' in one direction may lock the head coil apparatus 130 and prevent unwanted adjustment of the head coil apparatus 130 along the longitudinal direction L and rotation of the lock 134' in the opposite direction may release the head coil apparatus 130 and permit adjustment of the head coil apparatus 130 along the longitudinal direction L. In some embodiments, the lock(s) 134' have knurled circumferences to facilitate gripping and rotation by a clinician, as would be understood by those skilled in the art.

Referring to FIG. 29, the first end portion 130a of the head coil apparatus is substantially "U" shaped and includes spaced-apart leg portions 138, 140. In some embodiments, the head coil apparatus 130 may be configured such that a face plate 142 may be removably attached (e.g., snapped, threadingly engaged, etc.) to the head coil apparatus 130 at the leg portions 138, 140. The face plate 142 may include at least one internal RF coil and may be configured to be electrically coupled to the head coil apparatus 130 after being attached thereto. The face plate 142 typically does not extend along the entire longitudinal span (i.e., along direction L) of the head coil apparatus 130, thereby providing access to a patient's head, including in the space spanning from the second end portion 130b of the head coil apparatus 130 to the face plate 142 (FIG. 27). In addition, the face plate 142 may include an access window 144 to allow further access to a patient's head.

The head fixation assembly includes a plurality of upper head fixation members 40 and a plurality of lower head fixation members 44. In the illustrated embodiments, the head fixation assemblies include a pair of upper head fixation members 40 and a pair of lower head fixation members 44. Still referring to FIG. 29, each upper head fixation member 40 extends from a respective arm 18, 20 of the head fixation frame 14 and through a respective access window 133 of the head coil apparatus 130 (where used), as illustrated. The upper head fixation members 40 are inwardly adjustable relative to the head fixation frame 14 and configured to engage a patient's head within the free space of the head fixation frame 14. In some embodiments, each upper head fixation member 40 is threadingly engaged with a respective one of the arms 18, 20 of the head fixation frame 14. In some embodiments, each upper head fixation member 40 includes opposite first and second end portions 40a, 40b, as described in more detail above.

The lower head fixation members 44 extend from the head fixation frame 14 between the pair of arms 18, 20 and through respective access windows 133 of the head coil apparatus 130 (where used), as illustrated. The lower head fixation members 44 are also inwardly adjustable relative to the head fixation frame 14 and configured to engage an underside of a patient's head (skull) within the free space of the head fixation frame 14 and configured to hold and/or move a patient's head to a desired orientation in relation to the head coil apparatus 130 and/or the head fixation frame 14. In this regard, the lower head fixation members 44 may be configured to raise and lower a patient's head to a desired position relative to the head fixation frame 14 and/or the head coil apparatus 130. In some embodiments, the lower head fixation members 44 are threadingly engaged with the head fixation frame 14 between the arms 18, 20. In some embodiments, and as illustrated in FIG. 29, a pair of threaded bosses 146 extend from the portion of the head fixation frame 14 between the arms 18, 20 and a respective lower head fixation member 44 is threadingly engaged with each respective threaded boss 146. In some embodiments, each lower head fixation member 44 includes an end portion 44a (e.g., a disposable tip), as described in more detail above.

The lower head fixation members 44 may be configured to move (e.g., raise and/or lower) a patient's head while the patient's head resides in the free space of the head fixation frame 14. In other words, the lower head fixation members 44 may be adjusted (e.g., advanced and retracted) to move the patient's head after the patient's head has already been engaged by the tower head fixation members 44 and/or the upper head fixation members 40.

In some embodiments, a patient's head is attached to the head fixation frame 14 via engagement with the head fixation members 40, 44 and located inside the head coil apparatus 130; however, the patient's head typically resides above and does not contact the head coil apparatus 130. Likewise, in some embodiments where the face plate 142 is attached to the head coil apparatus 130, the patient's head also does not contact the face plate 142.

Referring again to FIG. 28, the upper head fixation members 40 may have an angled configuration such that each of the upper head fixation members 40 extend inwardly toward the free space defined by the head fixation frame 14 and downwardly along a respective direction that has an angle α relative to horizontal. The lower head fixation members 44 may have an angled configuration such that each of the lower head fixation members 44 extend inwardly toward the free space defined by the head fixation frame 14 and upwardly along a respective direction that has an angle β relative to vertical. By way of example, each of the upper head fixation members 40 may extend along a respective direction that has an angle α between about zero degrees and thirty degrees (0°-30°), and more particularly between about zero degrees and fifteen degrees (0°-15°), relative to horizontal. By way of further example, each of the lower head fixation members 44 may extend along a respective direction that has an angle β between about ten degrees and sixty degrees (10°-60°), and more particularly between about fifteen degrees and thirty degrees (15°-30°), relative to vertical.

As discussed above, the lower head fixation members 44 are adjustable relative to the head fixation frame 14. The lower head fixation members 44 may be directly or indirectly adjusted. More particularly, as illustrated in FIG. 28, each lower head fixation member 44 defines an axis A1. Typically, a respective lower head fixation member 44 is directly adjusted by rotating a drive about the same axis A1, as will be described in more detail below. In contrast, a respective lower head fixation member 44 is typically indirectly adjusted by rotating a drive about an axis that is different than the axis A1.

As such, the head fixation assemblies typically include at least one drive mechanism in communication with the lower head fixation members 44. The at least one drive mechanism may be externally accessible so as to allow a user to directly or indirectly advance and/or retract the lower head fixation members 44 while a patient's head resides in the free space of the head fixation frame 14.

In some embodiments, the lower head fixation members 44 can be indirectly adjusted by a drive mechanism that includes at least one drive located remote from the lower head fixation members 44. For example, the drive mechanism may be or include gears, a cam system, a linkage system, a traction drive, a pneumatic drive, a rack and pinion, or any other drive mechanism or system known to those of ordinary skill in the art. A single drive may be actuated to indirectly adjust (i.e. advance and retract) both lower head fixation members 44. Alternatively, a pair of drives may be employed, with each drive located remote from a respective lower head fixation member 44 and configured to be actuated to indirectly adjust the lower head fixation member 44. The indirect drive(s) may be configured for access by a clinician to the side or top of the head fixation frame 14 and may be manually actuated by rotation, pushing and/or pulling the drive(s), ratcheting the drive(s), or the like. Alternatively, the indirect drive(s) may be automated and thereby actuated via other control(s) away from the head fixation assembly.

Figure 30:
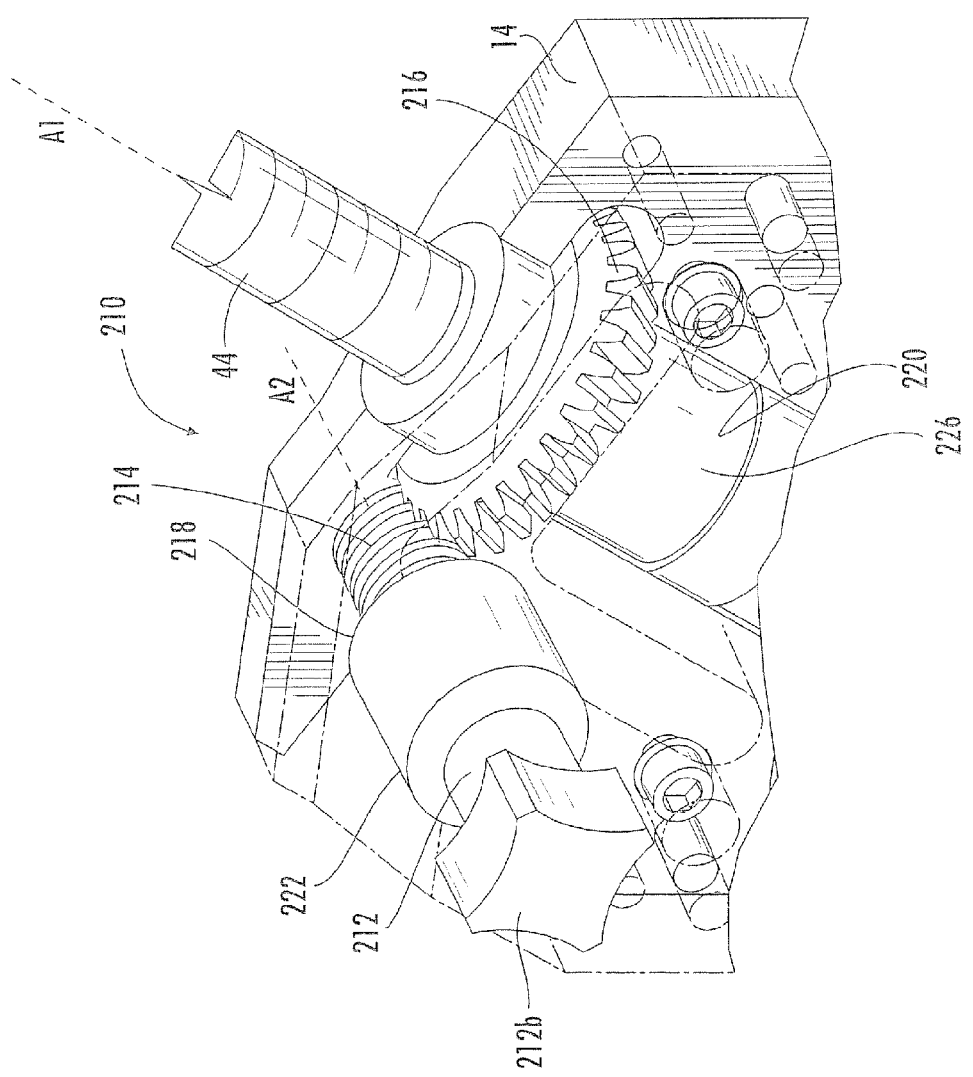
FIG. 30 is an enlarged partial perspective view of an exemplary drive mechanism for use with the head fixation assembly of FIG. 27, according to some embodiments of the present invention.

An exemplary indirect drive mechanism 210 is illustrated at FIG. 30. The drive mechanism 210 includes an external rotatable drive 212 at a location remote from a respective lower head fixation member 44. The drive mechanism 210 is configured to indirectly adjust (i.e., advance and retract) the lower head fixation member 44 along the axis A1 relative to the head fixation frame 14 responsive to rotation of the drive 212 about an axis A2 that is different than the axis A1 defined by the head fixation member 44. In some embodiments, an end portion 212b of the drive 212 has an enlarged configuration (e.g., thumb wheel) that facilitates rotation of the drive 212 by a clinician. Typically, rotation of the drive 212 in one direction will cause the lower head fixation member 44 to advance relative to the head fixation frame 14 and rotation of the drive 212 in the opposite direction will cause the lower head fixation member 44 to retract relative to the head fixation frame 14.

In some embodiments, and as illustrated at FIG. 30, the drive mechanism 210 includes a gear assembly that communicates with the lower head fixation member 44 and the remote drive 212. In the illustrated embodiment, the drive 212 has opposite proximal and distal ends. The drive is typically rotated by a clinician at its proximal end: in this regard, the enlarged end portion 212b may be located at the proximal end of the drive 212. The drive 212 extends through an aperture 218 in the head fixation frame. In some embodiments, the drive 212 is contained within a sleeve bearing 222; the sleeve bearing 222 may extend through the aperture 218 or may be flush with the head fixation frame 14. A worm 214 is located at the distal end of the drive 212. The worm 214 engages with a worm gear 216 associated with the lower head fixation member 44 such that axial rotation of the drive 212 causes axial rotation of the lower head fixation member 44. Axial rotation of the lower head fixation member 44 causes the lower fixation member 44 to advance or retract relative to the head fixation frame 14.

A portion of the lower head fixation member 44 may reside in a chamber 220 within the head fixation frame 14 and/or within a housing 226 within the chamber 220 (e.g., when the lower head fixation member 44 is retracted or not fully extended).

Referring to FIG. 29, a pair of drives 212 may be located on the "rear" side of the head fixation frame 14 at a location remote from the lower head fixation members 44 (i.e., on the right side of the head fixation frame 14 as seen in FIG. 27). Each of the drives 212 is configured to indirectly adjust a respective lower head fixation member 44 via a drive mechanism, such as the drive mechanism 210 illustrated in FIG. 30. Therefore, although not shown in FIG. 29, the head fixation assembly can include a pair of drive mechanisms (one for each lower head fixation member 44), such as the drive mechanism 210 illustrated in FIG. 30. In some embodiments, the drives 212 may be located on the opposite side of the head fixation frame 14. In other words, the drives may be located on the "front" side of the head fixation frame 14 (i.e., on the left side of the head fixation frame 14 as seen in FIG. 27).

The drive mechanisms described above permit indirect adjustment of the lower head fixation members and can offer several advantages. In the illustrated embodiment of FIG. 29, for example, the remote drives are conveniently located such that a clinician or the like can indirectly adjust the lower head fixation members from a variety of angles and positions. Furthermore, a patient's head can be adjusted (e.g., raised and/or lowered) even after the patient's head already resides in the head fixation frame. Therefore, the patient's head can be conveniently adjusted relative to the head coil apparatus, for example, to account for the size of the patient's head and/or the original position of the patient's head within the head fixation frame. Moreover, the lower head fixation members can be adjusted even after the patient's head has already been engaged by the lower head fixation members and/or the upper head fixation members. For example, the lower head fixation members may engage the underside of the patient's head and then the lower head fixation members may be adjusted to position the patient's head. The upper head fixation members may then be adjusted to secure the patient's head in the free space defined by the head fixation frame. Thereafter, the lower head fixation members may be further adjusted to further secure the patient's head (e.g., to embed the end portions or tips in the patient's soft tissue or skull).

As discussed above, the lower head fixation members 44 may also be directly adjusted. In some embodiments, the lower head fixation members 44 may be directly adjusted via at least one drive mechanism including an object that at least partially receives or at least partially surrounds the lower head fixation members 44.

Figure 32:
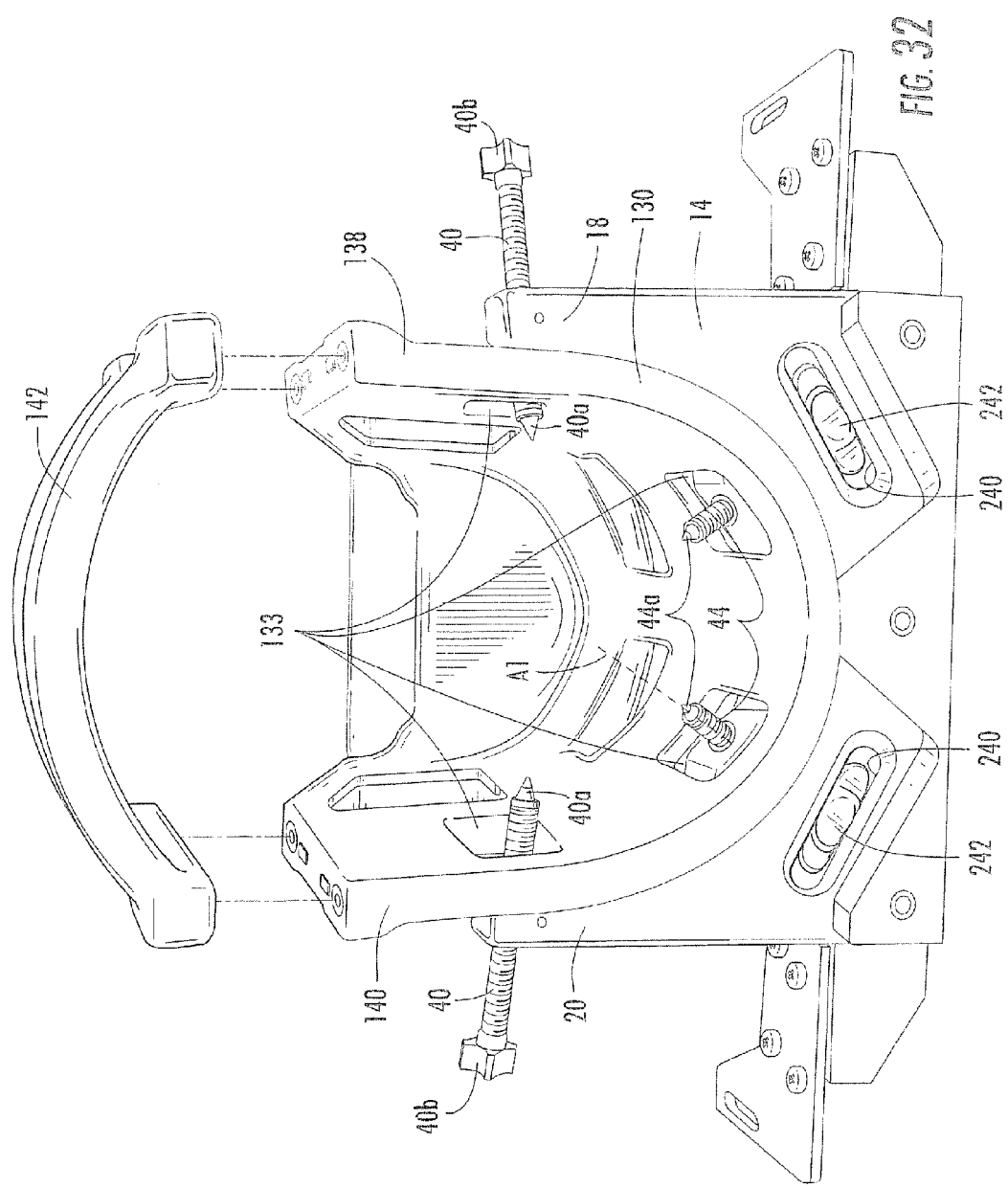
FIG. 32 is a perspective end view of the head fixation assembly of FIG. 31.

For example, the lower head fixation members 44 can be directly adjusted in the head fixation assemblies exemplified at FIGS. 31-34. In the illustrated embodiments, the at least one drive mechanism includes a pair of drive mechanisms. Each drive mechanism includes a substantially disk-shaped rotatable drive 242. The head fixation frame 14 includes a pair of spaced-apart slots or windows 240 extending therethrough and residing between the pair of arms 18, 20 above a bottom surface or an underside of the head fixation frame 14. Each drive 242 is positioned in a respective slot or window 240 of the head fixation frame 14. Each drive 242 includes a substantially centered aperture 244 configured to receive a respective lower head fixation member 44 (FIGS. 33-34), as described in more detail below. Each drive 242 is configured to directly adjust (i.e., advance and retract) the respective lower head fixation member 44 along the axis A1 responsive to rotation of the drive 242 about the same axis A1 (FIG. 32). In some embodiments, each drive 242 is in the form or shape of a thumb wheel to facilitate gripping and rotation by a clinician, as would be understood by those skilled in the art.

Figure 33:
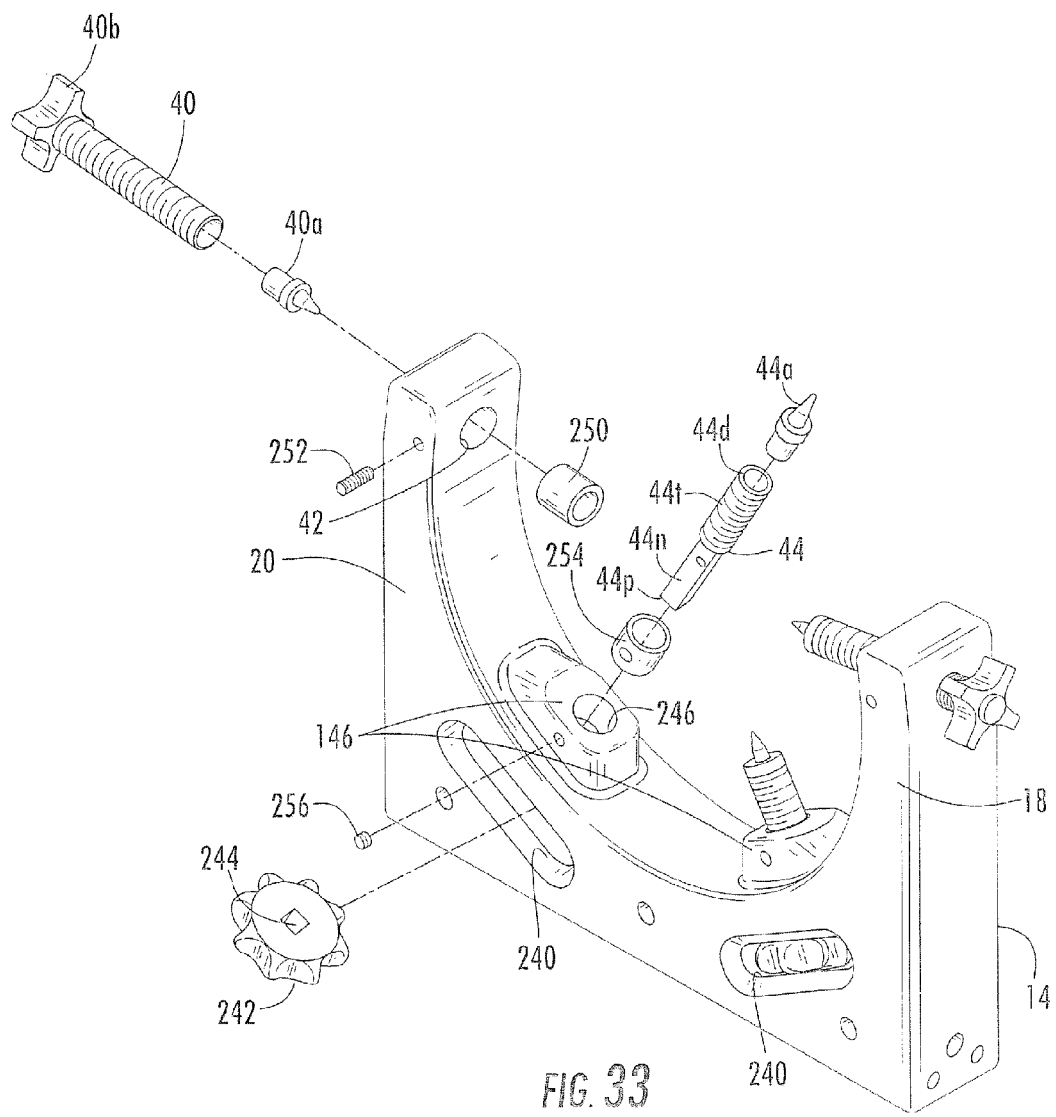
FIG. 33 is an exploded view of a head fixation frame, according to some embodiments of the present invention.

In some embodiments, and as illustrated at FIG. 33, the head fixation frame 14 includes an upper passageway 42 in each arm 18, 20, with the upper head fixation members 40 extending through the upper passageways 42. The head fixation frame 14 also includes a pair of lower passageways 246 residing in the head fixation frame 14 between the pair of arms 18, 20, with the lower head fixation members 44 extending through the lower passageways 246. Each lower passageway 246 intersects with a respective slot 240 in the head fixation frame 14. In some embodiments, the lower passageways 246 and the slots 240 intersect at substantially right angles. In some embodiments, bosses 146 extend from the portion of the head fixation frame 14 between the arms 18, 20 and the lower passageways 246 extend through the bosses 146.

In some embodiments, each upper head fixation member 40 is a threaded member and is threadingly engaged with a respective one of the arms 18, 20 of the head fixation frame 14. In this regard, the upper passageways 42 can be threaded such that the upper head fixation members 40 are threadingly engaged with the head fixation frame 14. Alternatively, in some embodiments, and as illustrated at FIG. 33, the head fixation frame 14 includes an insert or bushing 250 located in each upper passageway 42. The inserts 250 may be internally threaded (not shown) such that the upper head fixation members 40 are threadingly engaged with the inserts 250. The inserts 250 can be press fit within the upper passageways 42 and thereby snugly reside within the upper passageways 42. In some embodiments, the inserts 250 can be retained in the head fixation frame 14 by set screws 252, for example.

Likewise, in some embodiments, each lower head fixation member 44 is a threaded member and is threadingly engaged with the head fixation frame 14 between the pair of arms 18, 20. In this regard, the lower passageways 246 and/or the bosses 146 can be threaded such that the lower head fixation members 44 are threadingly engaged with the head fixation frame 14. Alternatively, in some embodiments, and as illustrated at FIG. 33, the head fixation frame 14 includes an insert or bushing 254 located in each lower passageway 246. The inserts 254 may be internally threaded (not shown) such that the lower head fixation members 44 are threadingly engaged with the inserts 254. The inserts 254 can be press fit within the lower passageways 246 and thereby snugly reside within the lower passageways 246. In some embodiments, the inserts 254 may be retained in the head fixation frame by set screws 256, for example.

Figure 34:
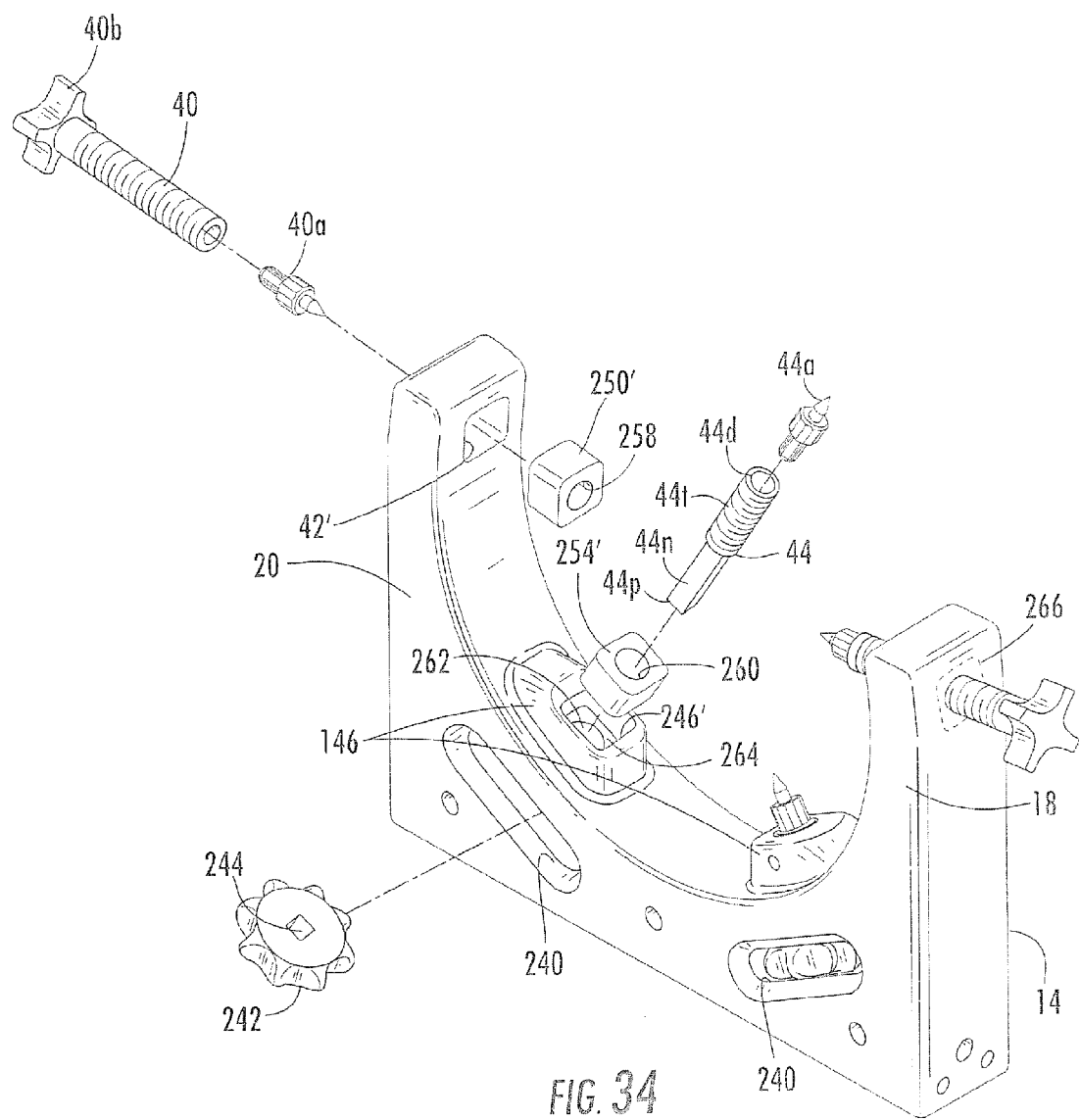
FIG. 34 is an exploded view of a head fixation frame, according to some alternative embodiments of the present invention.

In some embodiments, and as illustrated at FIG. 34, the head fixation frame 14 includes an upper passageway 42' in each arm 18, 20. The head fixation frame 14 also includes a pair of first lower passageways 246' residing in the head fixation frame 14 between the pair of arms 18, 20. In some embodiments, bosses 146 extend from the portion of the head fixation frame 14 between the arms 18, 20 and the first lower passageways 246' extend through the bosses 146. The upper and first lower passageways 42', 246' may have a rectangular cross-section, and may have a substantially square cross-section.

An upper anti-rotation block 250' is configured to fit within each upper passageway 42'. The upper anti-rotation blocks 250' can have substantially the same cross-sectional shape and size as the upper passageways 42'. For example, where the upper passageways 42' have a square cross-section, the upper anti-rotation blocks 250' can have substantially the same square cross-section. The upper anti-rotation blocks 250' may be sized to be press fit within the upper passageways 42' or may be adhered or otherwise secured to the upper passageways 42'. In some embodiments, each upper passageway 42' includes a lip 266, as shown by the dashed lines in FIG. 34. The lips 266 are located at the outer portion the arms 18, 20 of the head fixation frame 14. The lips 266 are configured to receive the upper anti-rotation blocks 250', and therefore the lips 266 may assist the user in positioning the upper anti-rotation blocks 250' in the upper passageways 42'. Furthermore, in some embodiments, the upper anti-rotation blocks 250' are configured to snugly reside within the upper passageways 42', and the lips 266 can serve a self-tightening function. In this regard, as the upper head fixation members 40 are adjusted (e.g., tightened, advanced, etc.), the upper anti-rotation blocks 250' may be tightened in the upper passageways 42' as well, such as by continued pushing against the lips 266, and the entire head fixation frame 14 and/or head fixation assembly may become more secure and/or more stable as a result.

Each upper anti-rotation block 250' defines a channel 258. The channels 258 may be substantially centered in the upper anti-rotation blocks 250'. Thus, each channel 258 may be substantially centered in a respective upper passageway 42'.

The upper head fixation members 40 extend through the channels 258; therefore, the channels 258 typically have a circular cross-section. The channels 258 may be threaded such that the upper head fixation members 40 may be threadingly engaged with the second upper passageways 257.

As shown, a lower anti-rotation block 254' is configured to fit within each first lower passageway 246'. The lower anti-rotation blocks 254' can have substantially the same cross-sectional size and shape as the first lower passageways 246'. For example, where the first lower passageways 246' have a square cross-section, the lower anti-rotation blocks 254' can have substantially the same square cross-section. The lower anti-rotation blocks 254' may be sized to be press fit within the first lower passageways 246' or may be adhered or otherwise secured to the first lower passageways 246'. In some embodiments, each first lower passageway 246' includes a lip 264, as shown in FIG. 34. The lips 264 are located at lowermost portion of the first lower passageways 246'. The lips 264 are configured to receive the lower anti-rotation blocks 254', and therefore the lips 264 may assist the user in positioning the lower anti-rotation blocks 254' in the first lower passageways 246'. Furthermore, in some embodiments, the lower anti-rotation blocks 254' are configured to snugly reside within the first lower passageways 246', and the lips 264 can serve a self-tightening function. In this regard, as the lower head fixation members 44 are adjusted (e.g., tightened, advanced, etc.), the lower anti-rotation blocks 254' may be tightened in the first lower passageways 246' as well, such as by continued pushing against the lips 264, and the entire head fixation frame 14 and/or head fixation assembly may become more secure and/or more stable as a result.

Each lower anti-rotation block 254' defines a channel 260. The channels 260 may be substantially centered in the lower anti-rotation blocks 254'. Thus, each channel 260 may be substantially centered in a respective first lower passageway 246'. The lower head fixation members 44 extend through the channels 260; therefore, the channels 260 typically have a circular cross-section. The channels 260 may be threaded such that the lower head fixation members 44 may be threadingly engaged with the channels 260.

The head fixation frame 14 may include a pair of second lower passageways 262. The lower head fixation members 44 extend through the second lower passageways 262. Each second lower passageway 262 intersects with a respective slot 240; in some embodiments, each second lower passageway 262 intersects with a respective slot 240 at a substantially right angle. The channels 260 mate with the second lower passageways 262 once the lower anti-rotation blocks 254' are positioned in the first lower passageway 246'. In this regard, each lower head fixation member 44 may extend through a common passageway comprising a respective channel 260 and a respective second lower passageway 262. The common passageway 260, 262 intersects with a respective slot 240 in the head fixation frame 14. In some embodiments, the common passageway 260, 262 and the slot 240 intersects at a substantially right angle. The second lower passageway 262 may have a similar shape or the same shape as the channel 260. The second lower passageway 262 may be threaded such that at least a portion of the lower head fixation member 44 is threadingly engaged with the second lower passageway 262. In some embodiments, the second lower passageway 262 need not be threaded where a portion of the lower head fixation member 44 is non-threaded, as described in more detail below.

In various embodiments, only the upper anti-rotation blocks 250' may be employed, only the lower anti-rotation blocks 254' may be employed, or both the upper anti-rotation blocks 250' and the lower anti-rotation blocks 254' may be employed. In some embodiments, both the upper anti-rotation blocks 250' and the lower anti-rotation blocks 254' are employed and are substantially identical in size and shape.

The anti-rotation blocks 250', 254' may be advantageous in that no locking mechanism may be required to hold the anti-rotation blocks 250', 254' in place. For example, the anti-rotation blocks 250', 254' may have a substantially square cross-section, and may be press fit (e.g., snugly reside) in the upper and first lower passageways 42', 246', respectively. The anti-rotation blocks 250', 254' may be any shape such that rotation of the anti-rotation blocks 250', 254' is inhibited as the head fixation members 40, 44 are adjusted. For example, the anti-rotation blocks may have a cross-section of any polygon or may be star-shaped or spline-shaped. When the upper and lower head fixation members 40, 44 are adjusted (i.e., advanced or retracted), the anti-rotation blocks 250', 254' can remain in place due to their shape and their fit within the passageways in the head fixation frame 14. Furthermore, as described in more detail above, the anti-rotation blocks 250', 254' may contact lips 264, 266 such that tightening of the head fixation members 40, 44 encourages further tightening of the anti-rotation blocks 250', 254' and/or increased stability of the head fixation frame 14 and/or the head fixation assembly.

Moreover, the anti-rotation blocks 250', 254' (as well as the inserts 250, 254) may be replaced over time, without having to replace the entire head fixation frame 14. For example, the anti-rotation blocks 250', 254' may be replaced when their associated threading becomes worn or may be replaced as needed for any other reasons (e.g., to maintain sterility). In addition, the anti-rotation blocks 250', 254' may be a different material than the head fixation frame 14. The material of the anti-rotation blocks 250', 254' may be more wear resistant and/or easier to machine (e.g., to form the proper shape and/or threading). In some embodiments, the head fixation frame 14 and the anti-rotation blocks 250', 254' are constructed of different MRI-compatible materials. For example, the head fixation frame 14 may be fiberglass, carbon fiber, or some other high-strength nonmagnetic material and the anti-rotation blocks 250', 254' may be a polymer such as Polyether ether ketone (PEEK).

The upper head fixation members 40 may have an angled configuration such that each of the upper head fixation members 40 extend inwardly toward the free space defined by the head fixation frame 14 and downwardly along a respective direction that has an angle relative to horizontal (e.g., the angle α seen in FIG. 28). In this regard, the upper passageways 42 may be angled downward from horizontal as they approach the free space defined by the spaced-apart arms 18, 20 of the head fixation frame 14 (FIG. 33). Likewise, the upper passageways and/or channels 42', 258 may be angled downward from horizontal as they approach the free space defined by the spaced-apart arms 18, 20 of the head fixation frame 14 (FIG. 34). Each of the upper head fixation members 40 may extend along a respective direction that has an angle between about zero degrees and thirty degrees (0°-30°), and more particularly between about zero degrees and fifteen degrees (0°-15°), relative to horizontal.

The lower head fixation members 44 may have an angled configuration such that each of the lower head fixation members 44 extend inwardly toward the free space defined by the head fixation frame 14 and upwardly along a respective direction that has an angle relative to vertical (e.g., the angle β seen in FIG. 28). In this regard, the lower passageways 246 may be angled toward the center of the free space defined by the arms 18, 20 of the head fixation frame 14 as the passageways 246 approach the free space (FIG. 33). Likewise, the first lower passageways, the channels, and/or the second lower passageways 246', 260, 262 may be angled toward the center of the free space defined by the arms 18, 20 of the head fixation frame 14 as the passageways/channels approach the free space (FIG. 34). Each of the lower head fixation members 44 may extend along a respective direction that has an angle between about ten degrees and sixty degrees (10°-60°), and more particularly between about fifteen degrees and thirty degrees (15°-30°), relative to vertical.

As illustrated in FIGS. 33 and 34, the first end portions 40a may be removable from the remainder of the upper head fixation members 40 and the end portions 44a may be removable from the remainder of the lower head fixation members 44. In some embodiments, the first end portions 40a are threadingly engaged with the remainder of the upper head fixation members 40 and/or the end portions 44a are threadingly engaged with the remainder of the lower head fixation members 44. In some other embodiments, the first end portions 40a are press fit within the remainder of the upper head fixation members 40 and/or the end portions 44a are press fit within the remainder of the lower head fixation members 44. In some other embodiments, the first end portions 40a and/or the end portions 44a are adhered to the remainder of the upper and lower head fixation members 40, 44, respectively.

In the embodiments illustrated in FIGS. 33 and 34, each lower head fixation member 44 has opposite proximal and distal ends 44p, 44d. Each lower head fixation member 44 is threaded and has a substantially circular cross section along a segment 44t extending inward from the distal end 44d. Each lower head fixation member 44 is non-threaded and has a substantially square-shaped cross section along a segment 44n extending outward from the proximal end 44p. The apertures 244 in the drives 242 have the same substantially square shape and are therefore configured to receive the proximal ends 44p (and possibly at least a portion of the non-threaded segments 44n) of the lower head fixation members 44. The apertures 244 in the drives 242 may be sized such that the proximal ends 44p and/or the non-threaded segments 44n of the lower head fixation members 44 fit snugly therein such that rotation of the drives 242 allows for efficient advancement and retraction of the lower head fixation members 44. Although the cross section of the proximal ends/non-threaded segments and the shape of the drive apertures have been described as being substantially square, other shapes are contemplated. By way of example, the proximal ends 44p and the non-threaded segments 44n may have a cross sectional shape of any polygon or may be star-shaped or spline-shaped, with the drive apertures 244 having a corresponding polygon shape or star shape or spline shape. These shapes can inhibit rotation of the lower head fixation members 44 relative to the drives 242 (e.g., the shapes can prevent slipping and allow for more efficient adjustment).

In some embodiments, portions of the non-threaded segments 44n, including the proximal ends 44p, may extend through the drive apertures 244 and thereby reside "beneath" the drives 242 (e.g., when the lower head fixation member 44 is not fully advanced relative to the head fixation frame 14). In this regard, these portions of the non-threaded segments 44n may reside in chambers and/or housings such as the chambers 220 and housings 226 described above and illustrated in FIG. 30.

The drives described immediately above permit direct adjustment of the lower head fixation members and can offer several advantages. For example, the slots in the head fixation frame and associated drives can be sized and/or shaped such that a clinician or the like can easily and conveniently rotate the drives and thereby directly adjust the lower head fixation members. Furthermore, a patient's head can be adjusted (e.g., raised and/or lowered) even after the patient's head already resides in the head fixation frame. Therefore, the patient's head can be conveniently adjusted relative to the head coil apparatus, for example, to account for the size of the patient's head and/or the original position of the patient's head within the head fixation frame. Moreover, the lower head fixation members can be adjusted even after the patient's head has already been engaged by the lower head fixation members and/or the upper head fixation members. For example, the lower head fixation members may engage the underside of the patient's head and then the lower head fixation members may be adjusted to position the patient's head. The upper head fixation members may then be adjusted to secure the patient's head in the free space defined by the head fixation frame. Thereafter, the lower head fixation members may be further adjusted to further secure the patient's head (e.g., to embed the end portions or tips in the patient's soft tissue or skull).

As discussed above, in some embodiments, the head fixation frame 14 and/or the anti-rotation blocks 250', 254' comprise material(s) that is suitable for use with MRI scanners. Where the head fixation frame 14 and/or the anti-rotation blocks 250', 254' are used in this environment, the material(s) preferably do not produce distortion or "flashing" in MRI images. Exemplary materials for the head fixation frame 14 include fiberglass, carbon fiber, or other high-strength non-magnetic materials. Exemplary materials for the anti-rotation blocks 250', 254' include various polymers, including Polyether ether ketone (PEEK).

The main difference between the embodiments illustrated at FIGS. 27-30 and those illustrated at FIGS. 31-34 is that the former employ drive mechanism(s) that allow for indirect adjustment of the lower head fixation members 44 whereas the latter employ drive mechanism(s) that allow for direct adjustment of the head fixation members 44. It is understood that the various features of the head fixation assemblies illustrated at FIGS. 27-34 can be combined. By way of example, although not shown in the Figures, the anti-rotation blocks 250', 254' may be employed with the embodiments illustrated at FIGS. 27-30.

Figure 35A:
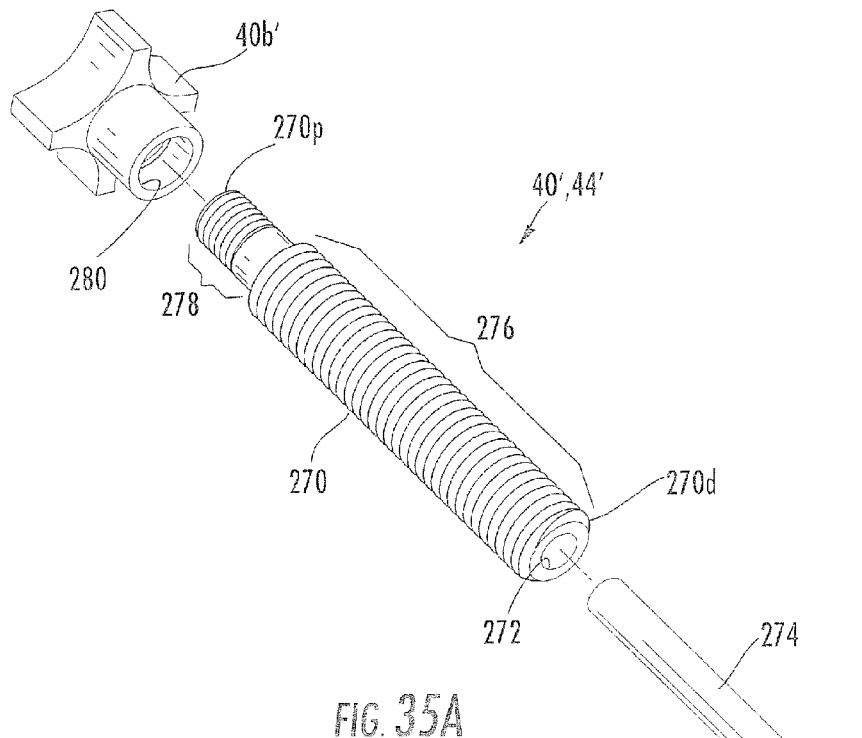
FIG. 35A is an exploded view of a head fixation member for use in head fixation frames, according to some embodiments of the present invention.
Figure 35B:
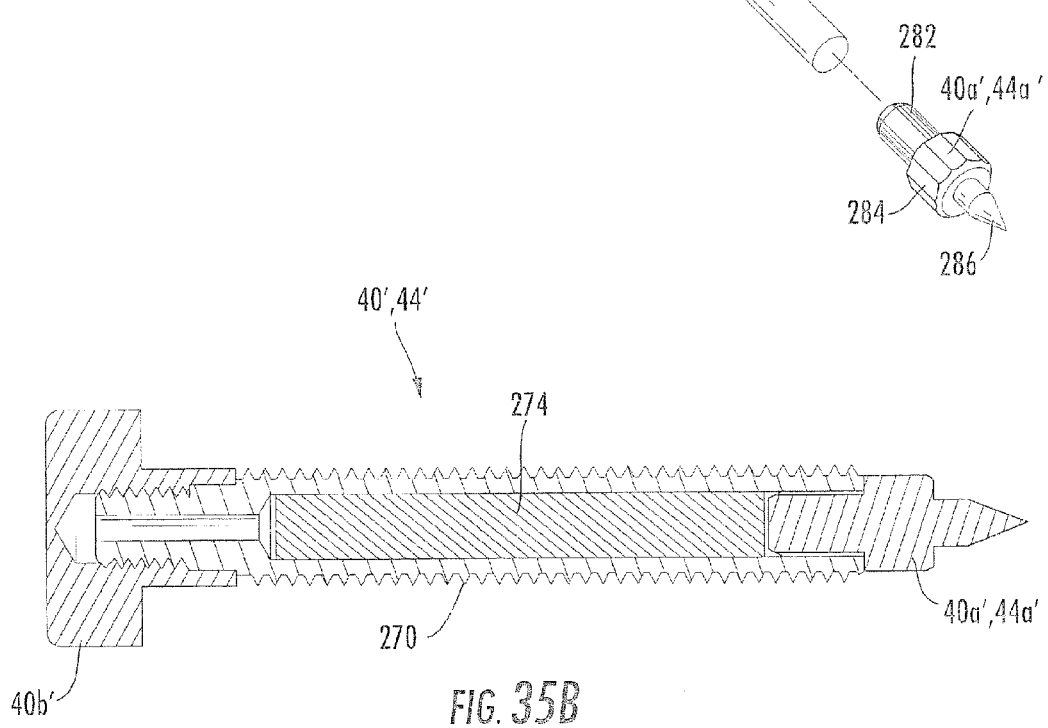
FIG. 35B is a side cross-section assembled view of the head fixation member of FIG. 35A.

Turning now to FIGS. 35A and 35B, another embodiment of upper and/or lower head fixation members 40', 44' for use with the head fixation assemblies/frames 14 described herein are illustrated. The head fixation members 40', 44' include an elongated outer member 270 having opposite proximal and distal ends 270p, 270c1. The elongated member 270 is at least partially hollow; in this regard, the elongated member 270 includes an open channel 272 extending from the distal end 270d inward along at least part of the of the elongated member's 270 length. Typically, the open channel 272 will extend along more than half the length of the elongated member 270. A rod 274 is configured to reside within the open channel 272. In some embodiments, the open channel 272 and the rod 274 are configured such that the rod 274 can be tightly contained within the open channel 272; for example, the rod 274 may be press fit within the open channel 272. In some embodiments, the elongated member 270 is constructed of a non-ferromagnetic material and the rod 274 is constructed of a non-ferromagnetic material with greater rigidity than the material of the elongated member 270. The rod 274 can improve the strength of the elongated member 270, and can therefore improve the strength of the head fixation member 40', 44' generally. In some embodiments, the elongated member 270 may polymeric, and may be Polyether ether ketone (PEEK), for example. In some embodiments, the rod 274 may be ceramic, and may be alumina, for example.

A first end portion or tip member 40a', 44a' is configured to be inserted within the open channel 272 of the elongated outer member 270. In the illustrated embodiment, the first end portion 40a', 44a' includes a center segment 284 separating an elongated segment 282 and a tip 286 (e.g., a sharp tip or point). The first end portion or tip member 40a', 44a' may be inserted within the open channel 272 after the rod 274 is inserted, for example. In this regard, the tip member 40a', 44a' resides within the open channel 272 at the distal end 270c1 of the elongated outer member 270 and extends outwardly therefrom. In the illustrated embodiment, the elongated segment 282 is inserted within the open channel 272 after the rod 274 is inserted. The elongated segment 282 may have a smaller cross-section than the center segment 284 such that the two segments have the appearance of a stepped shaft. This configuration may permit a clinician to grip the first end portion or tip member 40a', 44a' at the center segment 284 and/or the stepped shaft appearance may ensure than the first end portion or tip member 40a', 44a' (and possibly the rod 274) has been fully inserted within the open channel 272. The first end portion or tip member 40a', 44a' may be press fit within the open channel 272 or may be adhered to the interior of the open channel 272 in various embodiments. Alternatively, the elongated segment 282 and at least a portion of the open channel 272 may be threaded such that the first end portion or tip member 40a', 44a' is threadingly engaged with the open channel 272.

In some embodiments, the first end portion or tip member 40a', 44a' is disposable. The tip 286 of the first end portion or tip member 40a', 44a' is configured to engage the head or skull of a patient, as described in more detail above, and can be constructed of titanium, stainless steel, or other MRI compatible material. In some embodiments, the elongated and center segments 282, 284 are polymeric. In some embodiments, the center segment 284 and/or the elongated segment 282 are molded over the tip 286.

The elongated outer member 270 is threaded along at least part of its length. In the illustrated embodiment, the elongated member is threaded along a segment 276 extending from the distal end 270d inward. The threaded segment 276 is configured to be threadingly engaged with the head fixation frame 14 (FIG. 27), with the threaded insert 250 (FIG. 33), and/or with the channel 258 associated with the upper anti-rotation block 250' (FIG. 34).

In some embodiments, the elongated outer member 270 can also include a segment 278 extending from the proximal end 270p outward. With regard to the upper head fixation members 40', in some embodiments, at least a portion of the segment 278 is configured to fit within an open channel 280 of a second end portion 40b'. In some embodiments, the segment 278 is at least partially threaded along its length and the open channel 280 is at least partially threaded such that the segment 278 is threadingly engaged with the open channel 280. In some embodiments, the segment 278 is press fit so as to snugly reside within the open channel 280. In some other embodiments, the segment 278 is adhered within the open channel 280. In still other embodiments, the second end portion 40b' is integrated with or molded over the elongated outer member 270. In these embodiments, the segment 278 may be substantially the same diameter as the segment 276 or the segment 278 may be excluded. The second end portion 40b' may be the same material as the elongated outer member 270; for example, the components may be a one-piece polymeric molding, and the polymer may be Polyether ether ketone (PEEK), for example. The second end portion 40b' is typically configured to be rotated by a clinician to adjust (i.e., advance or retract) the head fixation member 40'. Therefore, in some embodiments, the second end portion 40b' is enlarged relative to the elongated member 260 and may take the form of a thumb wheel, for example.

With regard to the lower head fixation members 44', the second end portion 40b' may be omitted and the remainder of the assembly can be used as a lower head fixation member 44'. In some embodiments, the segment 278 is included and has cross-sectional shape to match the shape of the apertures 244 of the drives 242 (FIGS. 33 and 34). In some embodiments, the segment 268 is non-threaded, as described in more detail above.

Any of the head fixation assemblies/frames and methods described herein may employ upper head fixation members 40' and/or lower head fixation members 44'.

Figure 36A:
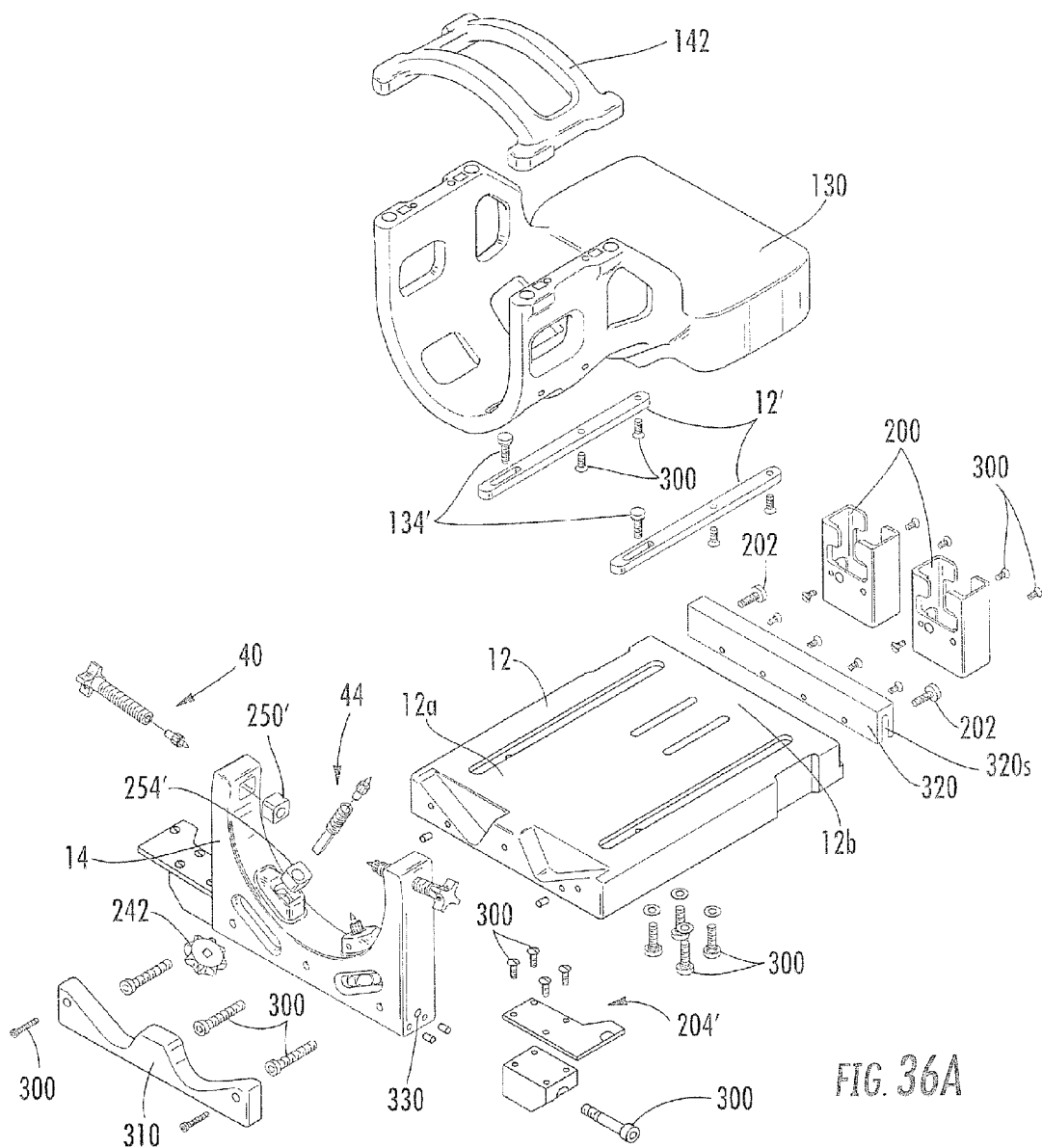
FIG. 36A is an exploded view of a modular head fixation assembly, according to some embodiments of the present invention.
Figure 36B:
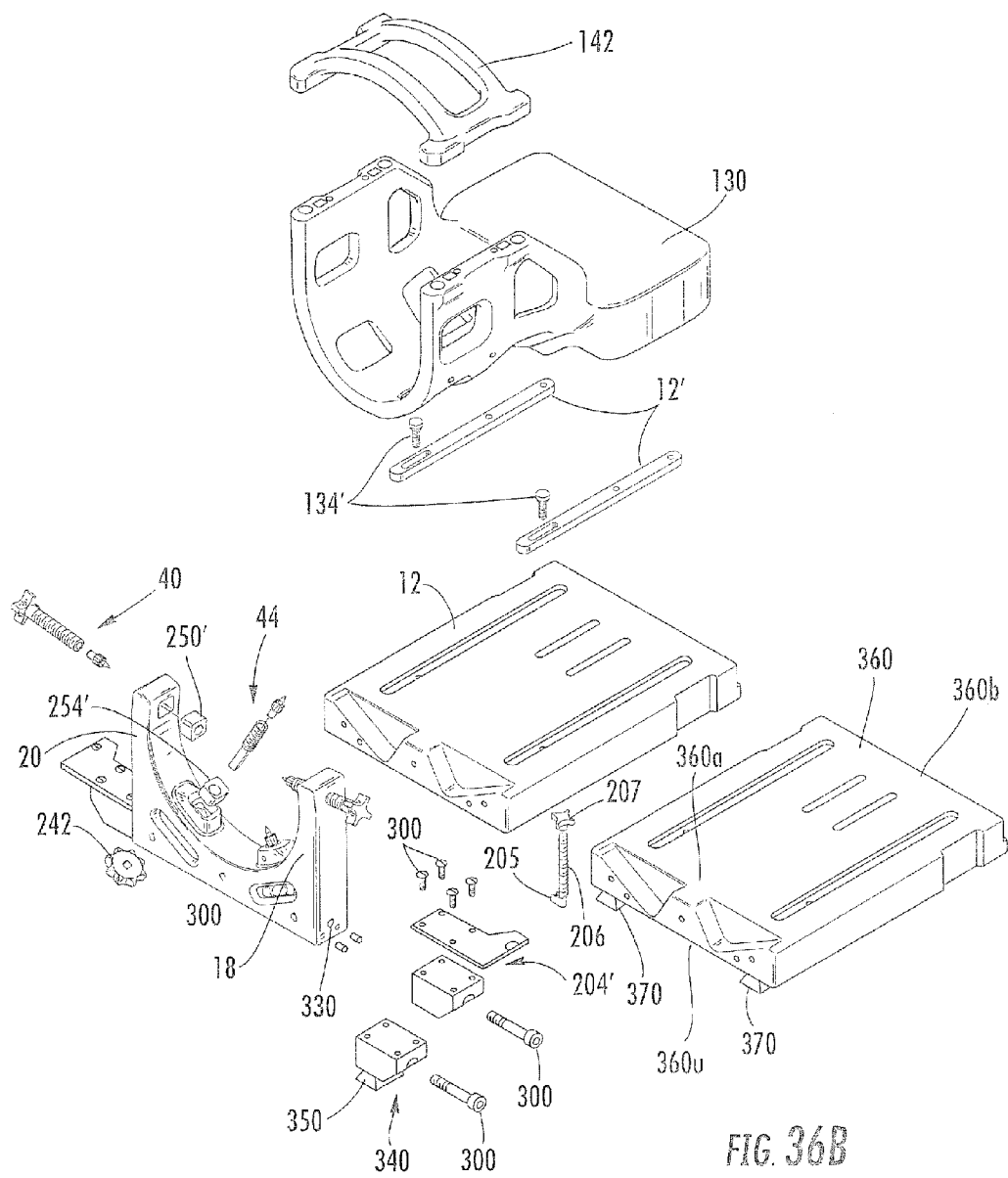
FIG. 36B is an exploded view of a modular head fixation assembly, according to various alternative embodiments of the present invention.

Turning now to FIGS. 36A and 36B, modular head fixation assemblies according to various embodiments of the present invention are presented. As used herein, a "modular head fixation assembly" is defined as an assembly in which various components can be attached and/or secured together to adapt the assembly to a particular surgical environment. For example, the modular head fixation assembly may be MRI-compatible, and may be adapted to be secured or locked to a gantry associated with an MRI scanner. The modular head fixation assemblies described herein may be advantageous because there are a variety of MRI scanner and/or gantry manufacturers and therefore a variety of gantry configurations, and a modular head fixation assembly may be "built up" or "customized" such that it can be secured to or locked to a particular gantry.

A modular head fixation assembly typically includes at least the head fixation frame 14. In some embodiments, the head fixation frame 14 remains the same for all gantry configurations, and other components are added to "customize" the head fixation assembly to a particular gantry configuration. The modular head fixation assembly may also "start" with various components associated with the head fixation frame 14, including, but not limited to, upper head fixation members 40, lower head fixation members 44, rotatable drives 242, and anti-rotation blocks 250', 254', for example.

Other components can then be added as needed or as specified by a customer. For example, the head fixation frame 14 may be releasably attached to the base 12 at its first end portion 12a using at least one fastener 300, for example. A plate 310 may be fastened to the head fixation frame 14 using at least one fastener 300, for example, to further stabilize the head fixation frame 14 and/or the base 12. Other components may then be attached to or secured to the base 12. For example, the head coil apparatus 130 may be secured to the base 12, or may be secured to moveable portions 12' of the base 12. At least one lock 134' may be included to inhibit longitudinal movement of the head coil apparatus 130 and/or to release the head coil apparatus 130 to permit longitudinal adjustment along the base 12. The face plate 142 may be removably attached to the head coil apparatus 130. Camera holders 200 may be releasably attached to the base 12. These components are described in more detail above.

Turning to FIG. 36B, the modular head fixation assemblies may include a variety of locking mechanisms to releasably lock the head fixation assembly to a variety of gantries. More particularly, at least one particular locking mechanism may be selected to releasably lock the modular head fixation assembly to a particular gantry configuration. For example, a side mounting assembly 204' may be releasably attached to each arm 18, 20 of the head fixation frame 14. Each arm 18, 20 may include at least one aperture 330 configured to receive a fastener 300 to releasably attach a side mounting assembly 204' to the respective arm 18, 20. Each side mounting assembly 204' includes a downwardly extending portion adapted to engage the gantry and thereby releasably lock the sides of the modular head fixation assembly to the gantry. In the illustrated embodiment, each side mounting assembly 204' includes a threaded member 206 (e.g., a screw) with an upwardly extending rotatable handle 207 attached to one end of the threaded member 206 and a clip 205 attached to the opposite end of the threaded member 206. In operation, the handle 207 can be rotated to advance and retract (e.g., lower and raise) the clip 205. The clips 205 may be configured to engage slots in the gantry and/or fit underneath the gantry, thereby locking the sides of the head fixation assembly to the gantry.

Still referring to FIG. 36B, an alternative side mounting assembly 340 may be releasably attached to the head fixation frame 14. The same at least one aperture 330 may be configured to receive a fastener 300 to releasably attach the side mounting assembly 340 to a respective arm 18, 20 of the head fixation frame 14. In the illustrated embodiment, the alternative side mounting assembly 340 includes a downward projection 350, which may have a dovetail configuration. The downward projection 350 is configured to be received by a slot or groove formed within a gantry.

Therefore, the head fixation frame 14 may be adapted to receive a variety of different side mounting assemblies such that the same head fixation frame 14 can be releasably locked to a variety of different gantries. Although the side mounting assemblies 204', 340 have been described in detail, other side mounting assembly configurations are contemplated. For example, side mounting assemblies including downwardly projecting clips similar to the clips 204 illustrated in FIG. 26 may be releasably attached to the head fixation frame 14.

FIG. 36B also illustrates an alternative base 360 which may be employed. The head fixation frame 14 releasably attaches to the base 360 at a first portion 360a. An underside 360u of the base 360 includes at least one downward projection 370 adjacent each transversely spaced-apart side of the base 360. The downward projections 370 are configured to engage respective slots or grooves formed within a gantry, thereby releasably locking the sides of the head fixation assembly to the gantry.

Any of the side mounting assemblies described herein may be used with any of the bases described herein to create a modular head fixation assembly configured to releasably lock to a particular gantry configuration.

In some embodiments, and as illustrated in FIG. 36A, the modular head fixation assembly may include further locking mechanisms, such as the rear mounting threaded members 202, described in more detail above. In the illustrated embodiment, a plate 320 has an inverse "U" shape and defines a slot 320s. The plate 320 may be releasably attached to the rear portion 12b of the base 12. The slot 320s defined by the plate 320 may be configured to receive an upward projection or flange associated with a gantry, for example. The rear mounting threaded members 202 may then be tightened to lock a rear portion of the head fixation assembly to the gantry. Other locking mechanisms adapted to lock a rear portion of the head fixation assembly to a particular gantry configuration are contemplated.

Figure 37:
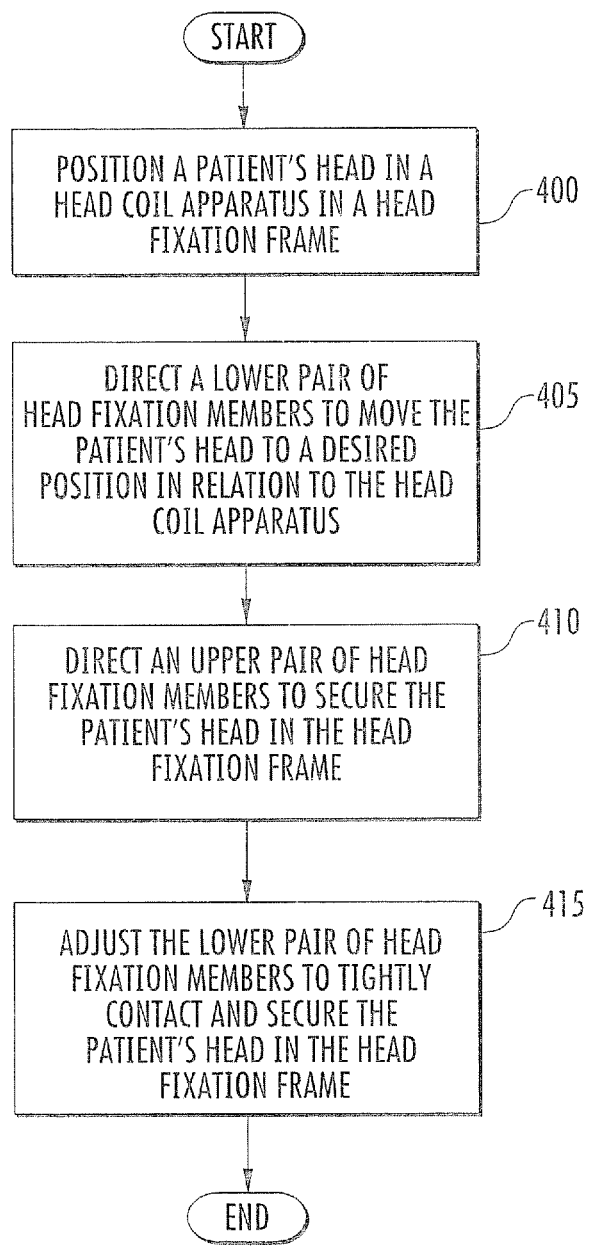
FIG. 37 is a flowchart illustrating exemplary operations, according to some embodiments of the present invention.

FIG. 37 illustrates an exemplary method for positioning a patient using embodiments of the head fixation assemblies described above. In some embodiments, a patient is first placed on a gantry (not shown). The patient's head is positioned in the head coil apparatus 130 held in the head fixation frame 14. (Block 400). The head fixation frame 14 includes a pair of upwardly extending spaced-apart arms 18, 20, an upper pair of head fixation members 40 extending from respective arms 18, 20, and a lower pair of head fixation members 44 extending from the head fixation frame 14 between the pair arms 18, 20. The lower pair of head fixation members 44 are then directed relative to the head fixation frame 14 to move the patient's head upward or downward to a desired position in relation to the head coil apparatus 130 (Block 405). In some embodiments, each of the lower pair of head fixation members 44 is directed by rotating a respective drive 242, as described in more detail above. In some other embodiments, each of the lower head fixation members is directed by rotating a respective drive 212 remote from the lower head fixation members 44, as described in more detail above.

The upper pair of head fixation members 40 is then directed inward and downward relative to the head fixation frame 14 to secure the patient's head in the head fixation frame 14 (Block 410). This may be performed by adjusting or tightening the upper pair of head fixation members 40 sequentially. The lower head fixation members 44 are then adjusted relative to the head fixation frame 14 to tightly contact and secure the patient's head in the head fixation frame 14 (Block 415). In some embodiments, each of the lower pair of head fixation members 44 is adjusted by rotating a respective drive 242, as described in more detail above. In some other embodiments, each of the lower head fixation members is adjusted by rotating a respective drive 212 remote from the lower head fixation members 44, as described in more detail above. The adjusting step may include piercing the patient's soft tissue or skull and/or further securing the patient's head in the head fixation frame.

In some embodiments, the head coil apparatus 130 is then adjusted to a desired longitudinal position in relation to the patient's head. This step may be performed after the adjusting or tightening steps (i.e., after the patient's head is secured in position).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A head fixation assembly for holding the head of a patient during a medical procedure, comprising:
 a base;
 a head fixation frame attached to the base, the head fixation frame comprising a pair of upwardly extending spaced-apart arms defining a free space therebetween;
 a head coil apparatus secured to the base, at least a portion of the head coil apparatus extending inside the free space of the head fixation frame, the head coil apparatus comprising at least one RF coil and configured to surround at least a portion of a patient's head, the head coil apparatus further comprising a plurality of spaced-apart access windows;
 a plurality of upper head fixation members, at least one extending from each of the respective arms of the head fixation frame and through a respective access window of the head coil apparatus, wherein the upper head fixation members are adjustable relative to the head fixation frame and adapted to engage a patient's head within the free space of the head fixation frame;

a plurality of lower head fixation members extending from the head fixation frame between the pair of arms, wherein each lower head fixation member is adjustable relative to the head fixation frame and adapted to engage an underside of the patient's head within the free space of the head fixation frame; and at least one drive mechanism in communication with the lower head fixation members, wherein the at least one drive mechanism is externally accessible so as to allow a user to be able to directly or indirectly (i) advance or retract or (ii) advance and retract the lower head fixation members while the patient's head resides in the free space of the head fixation frame.

2. The head fixation assembly of claim 1, wherein the head fixation assembly is a modular head fixation assembly adapted to be releasably locked to a gantry, wherein the base has a bottom surface, first and second opposite end portions, and transversely spaced-apart sides, wherein the head fixation frame is releasably attached to the base at the first end portion, the modular head fixation assembly further comprising:

either a first locking mechanism having a first configuration or a second locking mechanism having a second, different configuration, wherein the first and second locking mechanisms are each adapted to releasably lock the head fixation assembly to the gantry.

3. The head fixation assembly of claim 2, wherein the head fixation assembly comprises the first locking mechanism, the first locking mechanism comprising a pair of side mounting assemblies, each one releasably attached to a respective arm of the head fixation frame and including a downwardly extending portion adapted to engage the gantry and thereby releasably lock the sides of the head fixation assembly to the gantry.

4. The head fixation assembly of claim 2, wherein the head fixation assembly comprises the second locking mechanism, the second mechanism comprising at least one downwardly extending portion on the bottom surface of the base adjacent each of the sides of the base, the downwardly extending portions adapted to engage the gantry and thereby releasably lock the sides of the head fixation assembly to the gantry.

5. The head fixation assembly of claim 2, wherein the modular head fixation assembly is an MRI-compatible assembly, and wherein the gantry is associated with an MRI scanner.

6. The head fixation assembly of claim 5, wherein the head coil apparatus is adjustably secured to the base along a longitudinal direction relative to the head fixation frame.

7. The head fixation assembly of claim 6, wherein the base includes at least one lock configured to inhibit longitudinal movement of the head coil apparatus.

8. The head fixation assembly of claim 5, further comprising at least one camera holder attached to the base, wherein the camera holder is configured to hold an MRI-compatible camera therewithin.

9. The head fixation assembly of claim 5, wherein the head coil apparatus comprises a pair of upwardly-extending leg portions that reside at least partially within the head fixation frame, the head fixation assembly further comprising a face plate removably attached to the head coil apparatus at the leg portions.

10. The head fixation assembly of claim 1, wherein each upper head fixation member extends inwardly and downwardly at an angle of between about zero and fifteen degrees (0°-15°) relative to horizontal.

11. The head fixation assembly of claim 1, wherein each lower head fixation member extends upwardly at an angle of between about ten and sixty degrees (10°-60°) relative to vertical.

12. The head fixation assembly of claim 1, wherein the head fixation frame comprises:

an upper passageway in each arm;

a plurality of upper anti-rotation blocks, one each configured to snugly reside within a respective upper arm passageway, wherein each upper anti-rotation block includes a channel, and wherein one upper head fixation member extends through a respective one of the upper anti-rotation block channels;

a pair of lower passageways residing in the head fixation frame between the pair of arms; and a plurality of lower anti-rotation blocks, one each configured to snugly reside within a respective lower passageway, wherein each lower anti-rotation block includes a channel, and wherein one lower head fixation member extends through a respective one of the lower anti-rotation block channels.

13. The head fixation assembly of claim 12, wherein the head fixation members are threaded, and wherein the upper head fixation members threadingly engage the upper anti-rotation block channels and the lower head fixation members threadingly engage the lower anti-rotation block channels.

14. The head fixation assembly of claim 1, wherein each upper head fixation member comprises:

an elongated outer member having opposite proximal and distal ends, the elongated member having a channel open at the distal end;

a rod residing within the channel; and a tip member residing within the channel at the distal end of the elongated member and extending outwardly therefrom, the tip member having a sharp point.

15. The head fixation assembly of claim 14, wherein the elongated outer member is polymeric and the rod is ceramic.

16. The head fixation assembly of claim 1, wherein each lower head fixation member comprises:

an elongated outer member having opposite proximal and distal ends, the elongated member having a channel open at the distal end;

a rod residing within the channel; and a tip member residing within the channel at the distal end of the elongated member and extending outwardly therefrom, the tip member having a sharp point;

wherein the at least one drive mechanism is configured to receive the proximal end of the elongated member.

17. The head fixation assembly of claim 16, wherein the elongated outer member is polymeric and the rod is ceramic.

18. The head fixation assembly of claim 1, wherein the head fixation frame further comprises a pair of spaced-apart slots extending therethrough and residing between the pair of arms above a bottom surface of the head fixation frame, wherein the at least one drive mechanism comprises a pair drive mechanisms, wherein each drive mechanism comprises a substantially disk-shaped rotatable drive positioned in a respective slot of the head fixation frame, wherein each drive includes a substantially centered aperture configured to receive a portion of a respective lower head fixation member, and wherein each drive mechanism is configured to directly (i) advance or retract or (ii) advance and retract the respective lower head fixation member relative to the head fixation frame responsive to rotation of the rotatable drive.

19. The head fixation assembly of claim 18, wherein a respective lower head fixation member defines an axis, and wherein a respective drive mechanism is configured to directly (i) advance or retract or (ii) advance and retract the lower head fixation member responsive to rotation of the drive about the lower head fixation member axis.

20. The head fixation assembly of claim 18, wherein each lower head fixation member has opposite proximal and distal ends, with each lower head fixation member being threaded and having a substantially circular cross section along a segment extending inward from the distal end and each lower head fixation member being non-threaded and having a substantially square cross section along a segment extending outward from the proximal end, wherein the drive apertures are substantially square-shaped and configured to receive the proximal ends of the lower fixation members.

21. The head fixation assembly of claim 1, wherein the at least one drive mechanism comprises a pair of drive mechanisms, wherein each drive mechanism comprises a rotatable drive that is accessible by a user at a location remote from a respective lower head fixation member, the drive mechanism further comprising a gear assembly that communicates with the lower head fixation member and the remote drive, and wherein each drive mechanism is configured to indirectly (i) advance or retract or (ii) advance and retract the respective lower head fixation member relative to the head fixation frame responsive to rotation of the drive.

22. The head fixation assembly of claim 21, wherein a respective lower head fixation member defines an axis, and wherein a respective drive mechanism is configured to indirectly (i) advance or retract or (ii) advance and retract the lower head fixation member responsive to rotation of the drive about an axis that is different than the axis defined by the lower head fixation member.

23. The head fixation assembly of claim 21, wherein each rotatable drive has opposite proximal and distal ends with a worm located at the distal end, wherein the rotatable drive is configured to be rotated at the proximal end, and wherein the worm engages with a worm gear associated with the lower head fixation member such that axial rotation of the rotatable drive causes axial rotation of the lower head fixation member.

24. The head fixation assembly of claim 21, wherein the rotatable drives are positioned on a rear side of the head fixation frame.

25. A method for positioning a patient in a head fixation assembly, comprising:
    positioning a patient's head in a head coil apparatus held in a head fixation frame, wherein the head fixation frame comprises a pair of upwardly extending spaced-apart arms, an upper pair of head fixation members extending from respective arms of the head fixation frame, and a lower pair of head fixation members extending from the head fixation frame between the arms;
    directing the lower pair of head fixation members relative to the head fixation frame to move the patient's head upward or downward to a desired position in relation to the head coil apparatus; then
    directing the upper pair of head fixation members inward and downward relative to the head fixation frame to secure the patient's head in the head fixation frame; and then
    adjusting the lower pair of head fixation members relative to the head fixation frame to tightly contact and secure the patient's head in the head fixation frame.

26. The method of claim 25, wherein each lower head fixation member defines a respective axis, wherein the head fixation frame includes a pair of rotatable drives, each one at a location remote from a respective lower head fixation member and configured to advance and retract the lower head fixation member responsive to rotation of the drive about an axis that is different than the axis defined by the lower head fixation member, and wherein the steps of directing and adjusting the lower pair of head fixation members comprise rotating the pair of rotatable drives.

27. The method of claim 25, wherein each lower head fixation member defines a respective axis, wherein the head fixation frame includes a pair of substantially disk-shaped rotatable drives, each one configured to receive at least a portion of a respective lower head fixation member and configured to advance and retract the lower head fixation member responsive to rotation of the drive about the same axis defined by the lower head fixation member, and wherein the steps of directing and adjusting the lower pair of head fixation members comprise rotating the pair of substantially disk-shaped drives.

28. The method of claim 25, wherein the head coil apparatus is adjustably secured to a base, the method further comprising slidably translating the head coil apparatus to a desired longitudinal position in relation to the patient's head after the step of adjusting the lower pair of head fixation members.

29. A head fixation assembly for holding the head of a patient during a medical procedure, comprising:
    a head fixation frame comprising a pair of upwardly extending spaced-apart arms defining a free space therebetween;
    a plurality of upper head fixation members, at least one extending from each of the respective arms of the head fixation frame, wherein the upper head fixation members are adjustable relative to the head fixation frame and adapted to engage a patient's head within the free space of the head fixation frame;
    a plurality of lower head fixation members extending from the head fixation frame between the pair of arms, wherein each lower head fixation member is adjustable relative to the head fixation frame and adapted to engage an underside of the patient's head within the free space of the head fixation frame; and
    a pair of drive mechanisms, wherein each drive mechanism comprises a rotatable drive that is accessible by a user at a location remote from a respective lower head fixation member, wherein each drive mechanism is configured to indirectly (i) advance or retract or (ii) advance and retract the respective lower head fixation member relative to the head fixation frame responsive to rotation of the drive while the patient's head resides in the free space of the head fixation frame;
    wherein a respective lower head fixation member defines an axis, and wherein a respective drive mechanism is configured to indirectly advance or retract the lower head fixation member responsive to rotation of the drive about an axis that is different than the axis defined by the lower head fixation member.

30. A head fixation assembly for holding the head of a patient during a medical procedure, comprising:
    a head fixation frame comprising a pair of upwardly extending spaced-apart arms defining a free space therebetween;
    a plurality of upper head fixation members, at least one extending from each of the respective arms of the head fixation frame, wherein the upper head fixation members are adjustable relative to the head fixation frame and adapted to engage a patient's head within the free space of the head fixation frame;
    a plurality of lower head fixation members extending from the head fixation frame between the pair of arms, wherein each lower head fixation member is adjustable relative to the head fixation frame and adapted to engage an underside of the patient's head within the free space of the head fixation frame; and at least one drive mechanism in communication with the lower head fixation members, wherein the at least one drive mechanism is externally accessible so as to allow a user to be able to directly or indirectly (i) advance or retract or (ii) advance and retract the lower head fixation members while the patient's head resides in the free space of the head fixation frame;

wherein the head fixation frame comprises:

an upper passageway in each arm;

a plurality of upper anti-rotation blocks, one each configured to snugly reside within a respective upper arm passageway, wherein each upper anti-rotation block includes a channel, and wherein one upper head fixation member extends through a respective one of the upper anti-rotation block channels;

a pair of lower passageways residing in the head fixation frame between the pair of arms; and a plurality of lower anti-rotation blocks, one each configured to snugly reside within a respective lower passageway, wherein each lower anti-rotation block includes a channel, and wherein one lower head fixation member extends through a respective one of the lower anti-rotation block channels.

31. A head fixation assembly for holding the head of a patient during a medical procedure, comprising:

a head fixation frame comprising a pair of upwardly extending spaced-apart arms defining a free space therebetween;

a plurality of upper head fixation members, at least one extending from each of the respective arms of the head fixation frame, wherein the upper head fixation members are adjustable relative to the head fixation frame and adapted to engage a patient's head within the free space of the head fixation frame;

a plurality of lower head fixation members extending from the head fixation frame between the pair of arms, wherein each lower head fixation member is adjustable relative to the head fixation frame and adapted to engage an underside of the patient's head within the free space of the head fixation frame; and at least one drive mechanism in communication with the lower head fixation members, wherein the at least one drive mechanism is externally accessible so as to allow a user to be able to directly (i) advance or retract or (ii) advance and retract the lower head fixation members while the patient's head resides in the free space of the head fixation frame;

wherein the head fixation frame further comprises a pair of spaced-apart slots extending therethrough and residing between the pair of arms above a bottom surface of the head fixation frame, wherein the at least one drive mechanism comprises a pair drive mechanisms, wherein each drive mechanism comprises a substantially disk-shaped rotatable drive positioned in a respective slot of the head fixation frame, wherein each drive includes a substantially centered aperture configured to receive a portion of a respective lower head fixation member, and wherein each drive mechanism is configured to directly (i) advance or retract or (ii) advance and retract the respective lower head fixation member relative to the head fixation frame responsive to rotation of the rotatable drive.

* * * * *